(12) United States Patent
Kahne et al.

(10) Patent No.: US 6,699,836 B2
(45) Date of Patent: *Mar. 2, 2004

(54) VANCOMYCIN ANALOGS

(75) Inventors: Daniel Kahne, Princeton, NJ (US); Suzanne Walker, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/818,787

(22) Filed: Mar. 28, 2001

(65) Prior Publication Data

US 2002/0042365 A1 Apr. 11, 2002

Related U.S. Application Data

(60) Provisional application No. 60/199,382, filed on Apr. 25, 2000, and provisional application No. 60/127,516, filed on Apr. 2, 1999.

(51) Int. Cl.$^7$ ............................................... C07G 11/00
(52) U.S. Cl. ................ 514/7; 514/1; 514/8; 514/23; 530/322; 536/16.8
(58) Field of Search ............................. 530/322; 514/1, 514/8, 23; 536/16.8

(56) References Cited

U.S. PATENT DOCUMENTS

| | | | |
|---|---|---|---|
| 4,643,987 A | 2/1987 | Nagarajan et al. .............. | 514/8 |
| 4,791,100 A | 12/1988 | Kramer et al. ................. | 514/12 |
| 5,194,424 A | 3/1993 | Malabarba et al. ............ | 514/8 |
| 5,840,684 A | 11/1998 | Cooper et al. ................. | 514/11 |
| 5,919,756 A | 7/1999 | Cooper et al. ................. | 514/8 |
| 5,977,063 A | 11/1999 | Thompson et al. ............ | 514/8 |
| 6,498,238 B1 * | 12/2002 | Kim ........................... | 536/16.8 |

FOREIGN PATENT DOCUMENTS

| | | |
|---|---|---|
| EP | 0 301 785 | 2/1989 |
| WO | WO97/02288 | 1/1997 |
| WO | WO99/56760 | 11/1999 |
| WO | WO/0004044 | 1/2000 |
| WO | WO 00 04044 A | 1/2000 |
| WO | WO/0039156 | 7/2000 |
| WO | WO 00 39156 A | 7/2000 |
| WO | WO 00 42052 A | 7/2000 |
| WO | WO/0069892 | 11/2000 |
| WO | WO/0069893 | 11/2000 |
| WO | WO/0157071 | 8/2001 |

OTHER PUBLICATIONS

Sundram Uma N et al: *General and Efficient Method for the Solution—and Solid–Phase Synthesis of Vancomycin Carboxamide Derivatives*, Journal of Organic Chemistry, American Chemical Societ6y, Easton, US, Mar. 10, 1995, pp. 1102–1103, XP002183429.

M.F. Cristofaro et al., "Cooperativity between non–polar and ionic forces in the binding of cell wall analogues by vancomycin in aqueous solutions", J. of Antibiotics, vol. 48, No. 8, Aug. 1995 Tokyo, JP.

P. Booth and D. Williams "Preparation and conformational analysis of vancomycin hexapeptide and aglucovancomycin hexapeptide" J. of the Chemical Society Perkin Transactions, vol. 1, No. 12, Dec. 1989 Letchworth, GB.

A. Malabarda, et al., "Structural modifications of glycopeptide antibiotics", Medical Research Reviews, vol. 17, No. 1, 1997 New York, NY, US.

* cited by examiner

*Primary Examiner*—Christopher R. Tate
*Assistant Examiner*—Roy Teller
(74) *Attorney, Agent, or Firm*—Kenyon & Kenyon

(57) ABSTRACT

Compounds that are vancomycin analogs bearing terminal carboxyl group modifications as well as modifications to the vancosamine nitrogen and, optionally, modifications to the C6 position of the glucose residue attached to the amino acid four of the vancomycin heptapeptide chain are disclosed. Methods of making the compounds and methods of using the compounds to treat a bacterial infection in a host are also disclosed.

19 Claims, No Drawings

US 6,699,836 B2

VANCOMYCIN ANALOGS

This application claims the benefit of provisional application Serial No. 60/199,382 filed Apr. 25, 2000.

Incorporated herein in their entireties are the disclosures of pending U.S. patent application Ser. No. 09/353,368, filed Jul. 14, 1999 entitled "GLYCOPEPTIDE ANTIBIOTICS, COMBINATORIAL LIBRARIES OF GLYCOPEPTIDE ANTIBIOTICS AND METHODS OF PRODUCING SAME" and pending U.S. patent application Ser. No. 09/540,761 filed Mar. 31, 2000, entitled "DESLEUCYL GLYCOPEPTIDE ANTIBIOTICS AND METHODS OF MAKING SAME" which claims the benefit of Provisional Application Ser. No. 60/127,516, filed Apr. 2, 1999.

FIELD OF THE INVENTION

The present invention relates to vancomycin analogs having antibacterial activity; methods of making vancomycin analogs having antibacterial activity; and, methods of treating a bacterial infection in a host with a vancomycin analog having antibacterial activity.

BACKGROUND OF THE INVENTION

Vancomycin is a very important drug for the treatment of gram positive infections. It has been proposed that vancomycin works by binding to the D-ala-D-ala termini of Lipid II molecules and/or to nascent peptidoglycan, preventing maturation of the cell wall. Vancomycin is used to treat infections that are resistant to antibiotics. Hence, vancomycin has been called the "drug of last resort" because it is often the last remaining option for the treatment of gram positive infections caused by strains that have become resistant to all other antibiotics.

Resistance to vancomycin first appeared about fifteen years ago and the frequency of resistance is increasing. There have been numerous efforts to develop vancomycin analogs that overcome this resistance. For example, it has been reported that certain derivatives of vancomycin containing hydrophobic substituents at the vancosamine nitrogen are active against vancomycin resistant enterococcal strains. The inventors of the present application have also reported activity against resistant and sensitive strains of vancomycin analogs in which the C6 position of the glucose residue directly attached to amino acid four of the heptapeptide chain of vancomycin is modified to bear a substituent other than a naturally occuring hydroxyl and the vancosamine nitrogen is optionally modified. In some cases, compounds in which both the C6 position of the glucose residue and the vancosamine nitrogen are modified are more active than the singly substituted parent compounds, and even have good activity against staphylococcal strains.

Attempts have been made to modify the terminal carboxyl group of the peptide chain in certain glycopeptide antibiotics. For example, terminal carboxyl group modifications to vancomycin, chloroeremomycin and teicoplanin derivatives have been reported. U.S. Pat. No. 5,919,756, incorporated herein in its entirety, discloses amide modifications of the terminal carboxyl group in chloroeremomycin in combination with modifications to the vancosamine nitrogen. U.S. Pat. No. 5,194,424, incorporated herein in its entirety, discloses amide modifications of the terminal carboxyl group in certain teicoplanin derivatives. The present inventors are unaware of any reported vancomycin analogs in which both the terminal carboxyl group of the heptapeptide chain and the vancosamine nitrogen of vancomycin are modified, and in which the C6 position of the glucose residue directly attached to amino acid four of the heptapeptide chain is optionally modified to bear a substituent other than a naturally occurring hydroxyl group.

It is believed that substitution of the vancosamine nitrogen, especially with a hydrophobic substituent, generally reduces solubility of the compound relative to the unsubstituted vancomycin parent compound. Delivery of these vancosamino-substituted compounds is complicated by the decreased solubility of these compounds, particularly through intravenous delivery routes. While not wishing to be bound by theory, the present inventors believe that this decreased solubility may be mitigated by modification of the terminal carboxyl group in vancomycin also bearing a vancosamine nitrogen substituent. Additional modifications may also be made, particularly to the C6 position of the glucose residue directly attached to amino acid four in the heptapeptide chain of vancomycin. These additional modifications may also improve the physical properties (i.e. solubility) and or activity of the compounds of the present invention relative to known vancomycin analogs.

DEFINITIONS

A "glycoconjugate" comprises any molecule linked to at least one carbohydrate of any size. The molecule can be a peptide or protein, a nucleic acid, a small molecule, a lipid, or another carbohydrate; it may be of natural or non-natural origin.

A "glycopeptide" is a glycoconjugate comprising a peptide linked to at least one carbohydrate.

A "glycopeptide antibiotic" is a glycopeptide having antibacterial activity, including, e.g., vancomycin, eremomycin, chloroeremomycin and β-avoparcin as well as any synthetic and semi-synthetic derivatives thereof. The term "glycopeptide antibiotic" is meant to encompass any naturally occurring antibiotic as well semi-synthetic derivatives thereof.

An "aglycone" is the result of removing the carbohydrate residues from a glycopeptide, leaving only a peptide core.

A "pseudoaglycone" is the result of removing only one of two sugar residues from a disaccharide residue linked to amino acid residue four of the peptide chain of glycopeptide. Thus, a pseudoaglycone comprises an aglycone in which amino acid four of the peptide chain is linked to a monosaccharide residue.

A "dalbaheptide" is a glycopeptide containing a heptapeptide moiety which is held in a rigid conformation by cross-links between the aromatic substituent groups of at least five of the seven α-amino acid residues, including a cross-link comprising a direct carbon—carbon bond between the aryl substituents of amino acid residues 5 and 7, and aryl ether cross-links between the substituents of amino acid residues 2 and 4, and 4 and 6. Amino acid residues 2 and 4–7 in different dalbaheptides are those found in the naturally occurring glycopeptide antibiotics. These amino acid residues differ only in that residues 2 and 6 do not always have a chlorine substituent on their aromatic rings, and in that substitution on free hydroxyl or amino groups may be present. Amino acids residues 1 and 3 may differ substantially in different dalbaheptides; if both bear aryl substituents, these may be cross-linked. Molecules having a dalbaheptide structure include, e.g., the glycopeptide antibiotics mentioned above.

The term "alkyl" refers to a linear or branched acyclic or non-aromatic cyclic group having from one to twenty carbon atoms connected by single or multiple bonds. Thus, the term "alkyl" is meant to encompass linear or branched acyclic or non-aromatic groups having one or more carbon—carbon double or triple bonds, i.e., alkenyl and alkynyl groups. An alkyl group may be substituted by one or more of halo, hydroxyl, protected hydroxyl, amino, protected amino, nitro, cyano, alkoxy, aryloxy, aralkyloxy, COOH, aroyloxy, alkylamino, dialkylamino, trialkylammonium, alkylthio, arylthio, alkanoyl, alkanoyloxy, alkanoylamido, alkylsulfonyl, arylsulfonyl, aroyl, aralkanoyl, heterocyclic, $CONH_2$, CONH-alkyl, $CON(alkyl)_2$, COO-aralkyl, COO-aryl or COO-alkyl.

The term "cycloalkyl" embraces substituents having from four to ten carbon atoms, such as cyclobutyl, cyclopentyl, cyclohexyl, and cycloheptyl which may be unsubstituted or substituted with any of the groups with which alkyl may be substituted. This term also embraces $C_5$ to $C_{10}$ cycloalkenyl groups such as cyclopentenyl and cyclohexenyl. The term "cycloalkyl" also embraces bicyclic and tricyclic cycloalkyls such as bicyclopentyl, bicylohexyl, bicycloheptyl, and adamantyl.

The term "aryl" refers to a group derived from a non-heterocyclic aromatic compound having from six to twenty carbon atoms and from one to four rings which may be fused or connected by single bonds. An aryl group may be substituted by one or more of alkyl, aralkyl, heterocyclic, heterocyclic-alkyl, heterocyclic-carbonyl, halo, hydroxyl, protected hydroxyl, amino, protected amino, hydrazino, alkylhydrazino, nitro, cyano, alkoxy, aryloxy, aralkyloxy, aroyloxy, alkylamino, dialkylamino, trialkylammonium, alkylthio, arylthio, alkanoyl, alkanoyloxy, alkanoylamido, alkylsulfonyl, arylsulfonyl, aroyl, aralkanoyl, COO-alkyl, COO-aralkyl, COO-aryl, $CONH_2$, CONH-alkyl or $CON(alkyl)_2$. Examples of fused aryl groups include, e.g., fluorenyl, naphthyl, anthranyl, phenanthranyl, biphenylene and pyrenyl.

The term "aralkyl" refers to an alkyl group substituted by an aryl group. Aralkyl may optionally be substituted with one or more of the groups with which alkyl or aryl may be substituted.

The term "heterocyclic" refers to a group derived from a heterocyclic compound having from one to four rings, which may be fused or connected by single bonds; said compound having from three to twenty ring atoms which may be carbon, nitrogen, oxygen, sulfur or phosphorus. A heterocyclic group may be substituted by one or more alkyl, aryl, aralkyl, halo, hydroxyl, protected hydroxyl, amino, hydrazino, alkylhydrazino, arylhydrazino, nitro, cyano, alkoxy, aryloxy, aralkyloxy, aroyloxy, alkylamino, dialkylamino, trialkylamino, alkylthio, arylthio, alkanoyl, alkanoyloxy, alkanoylamido, alkylsulfonyl, arylsulfonyl, aroyl, aralkanoyl, COO-alkyl, COO-aralkyl, COO-aryl, $CONH_2$, CONH-alkyl or $CON(alkyl)_2$.

The term "heteroaryl", represents a stable, saturated or unsaturated, substituted or unsubstituted, 4 to 7 membered organic monocyclic ring having a hetero atom selected from S, O, and N; a stable, saturated or unsaturated, substituted or unsubstituted, 9 to 10 membered organic fused bicyclic ring having 1 to 2 hetero atoms selected from S, O, and N; or a stable, saturated or unsaturated, substituted or unsubstituted, 12 to 14 membered organic fused tricyclic ring having a hetero atom selected from S, O, and N. The nitrogen and sulfur atoms of these rings are optionally oxidized, and the nitrogen hetero atoms are optionally quarternized. The monocyclic ring may have 0 to 5 substituents. The bicyclic ring may have 0 to 7 substituents, and the tricyclic ring may have 0 to 9 substituents. Typical heteroaryls include quinolyl, piperidyl, thienyl, piperonyl, oxafluorenyl, pyridyl and benzothienyl and the like. Heteroaryl may be substituted with any of the groups with which aryl may be substituted.

The terms "alkoxy," "aryloxy," and "aralkyloxy," refer to groups derived from bonding an oxygen atom to an alkyl, aryl or aralkyl group, respectively. Any alkoxy, aryloxy or aralkyloxy group may optionally be substituted with one or more of the groups with which alkyl, aryl or aralkyl may be substituted. The terms "alkanoyl," "aroyl," and "aralkanoyl" refer to groups derived from bonding a carbonyl to an alkyl, aryl or aralkyl group, respectively. Any alkanoyl, aroyl or aralkanoyl group may optionally be substituted with one or more of the groups with which alkyl, aryl or aralkyl may be substituted. The terms "heterocyclic-alkyl" and "heterocyclic-carbonyl" refer to groups derived from bonding a heterocyclic group to an alkyl or a carbonyl group, respectively. An heterocyclic-alkyl or heterocyclic-carbonyl group may optionally be substituted with one or more of the groups with which heterocyclic or alkyl may be substituted. The term "heterocyclic-alkyl-carbonyl" refers to a group derived from bonding a heterocyclic-alkyl group to a carbonyl group. Any heterocyclic-alkyl-carbonyl may optionally be substituted with one or more of the groups with which heterocyclic or alkyl may be substituted. The term "alkylsulfonyl" refers to a group derived from bonding an alkyl group to a sulfonyl group. An alkylsulfonyl group may optionally be substituted with one or more groups with which alkyl may be substituted. The term "arylsulfonyl" refers to a group derived from bonding an aryl group to a sulfonyl group. An arylsulfonyl group may optionally be substituted with one or more groups with which aryl may be substituted. The term "protected hydroxyl" refers to a hydroxyl group bonded to a group which is easily removed to generate the free hydroxyl group by treatment with acid or base, by reduction or by exposure to light, or by any other conventional means for removing a protecting group from a hydroxyl group. The term "protected amino" refers to an amino group bonded to a group which is easily removed to generate the free amino group by treatment with acid or base, by reduction or exposure to light, or by any other conventional means for removing a protecting group from an amino group.

A "chemical library" is a synthesized set of compounds having different structures. The chemical library may be screened for biological activity to identify individual active compounds of interest.

The term "DMF" refers to N,N-dimethylformamide; "THF" refers to tetrahydrofuran; "TFA" refers to trifluoroacetic acid; "EtOAc" refers to ethyl acetate; "MeOH" refers to methanol, "MeCN" refers to acetonitrile; "Tf" refers to the trifluoroacetyl group; "DMSO" refers to dimethyl sulfoxide; "DIPEA" refers to diisopropylethylamine; "All" in structural formulas refers to the allyl group; "Fmoc" refers to 9-fluorenylmethyloxycarbonyl; "HOBt" refers to 1-hydroxybenzotriazole and "Obt" to the 1-oxybenzotriazolyl group; "PyBOP" refers to benzotriazol-1-yl-oxyatripyrrolidine-phosphonium hexafluorophosphate; "Su" refers to the succinimidyl group; "HBTU" refers to O-benzoatriazol-1-yl-N2N3N',N'-tetramethyluronium hexafluorophosphate; "alloc" refers to allyloxycarbonyl; and "CBZ" refers to benzyloxycarbonyloxy.

The term "hydrophobic" as used herein to describe a compound of the present invention or a substituent thereon, refers to the tendency of the compound or substituent thereon to lack an affinity for, to repel or to fail to absorb water, or to be immiscible in water. The term "hydrophobic" is not meant to exclude compounds or substituents thereon that are not completely immiscible in water.

The term "polar" as used herein to describe a compound of the present invention or a substituent thereon, refers to the tendency of the compound or substituent thereon to have an affinity for, to attract or to absorb water, or to be miscible in water. The term "polar" is not meant to exclude compounds or substituents thereon that are not completely miscible in water.

The term "pharmaceutically acceptable salt" as used herein, refers to salts of the compounds of the present invention which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, g-hydroxybutyrate, glycollate, tartrate, methanesulfonate, propanesulfonate, naphthalene-1-sulfonate, naphthalene-2-sulfonate, mandelate and the like. Preferred pharmaceutically acceptable acid addition salts are those formed with mineral acids such as hydrochloric acid and hydrobromic acid, and those formed with organic acids such as maleic acid, acetic acid, and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

SUMMARY OF THE INVENTION

The present invention is directed vancomycin analogs of the formula:

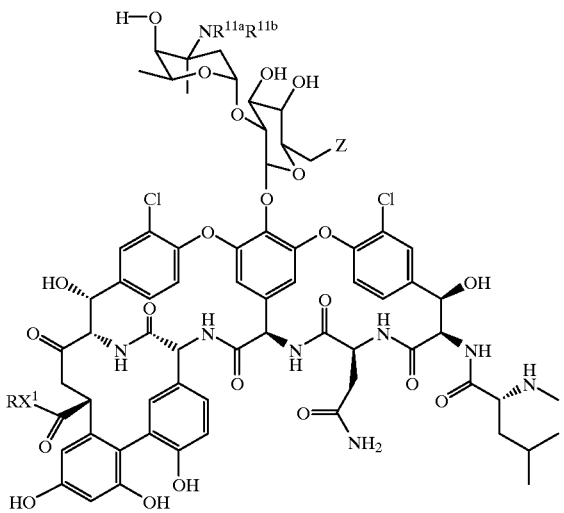

wherein $X^{-1}$ is O, S, NR, $NR^1$, $NR^2$, with the proviso that $RX^1$ is not OH;

wherein R is hydrogen, substituted or unsubstituted alkyl, aryl, aralkyl, alkanoyl, aroyl, aralkanoyl, heterocyclic, heterocyclic-carbonyl, heterocyclic-alkyl-carbonyl, alkylsulfonyl or arylsulfonyl, $R^1$ or $R^2$;

wherein $R^1$ is a radical of the formula $—[(CH_2)_m NR^3]_n—Q—[(CH)_k NR^4]_h—(CH_2)_p—NR^5 R^6$ wherein: any of $R^3$, $R^4$, $R^5$ and $R^6$ is hydrogen or linear or branched $(C_1-C_8)$ alkyl that may optionally be substituted with one or more substituents each of which is independently selected from the group consisting of halo, nitro, cyano, loweralkoxy of $C_1-C_4$, haloloweralkyl of $C_1-C_4$, haloloweralkoxy of $C_1-C_4$, $NH_2$, OH or SH; or $R^5$ and $R^6$ taken together with the adjacent nitrogen atom, form a 5 to 7 membered saturated heterocyclic ring which may contain a further heteroatom selected from —S—, —O—, and $NR^7$ wherein $R^7$ is hydrogen, $(C_1-C_4)$alkyl, phenyl, or phenyl-$(C_1-C_4)$alkyl; m, k and p, each independently represent and integer from 2 to 8; n and h, each independently, represent an integer from 0 to 4; Q represents a single bond, or when n is 1, taken together with the adjacent group $NR^3$, it may represent a bifunctional radical of the formula:

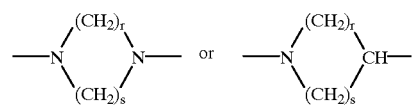

wherein r and s each independently represent an integer from 1 to 6 with the proviso that their sum is an integer from 3 to 8; and their addition salts with acids;

wherein $R^2$ is $—CH_2 R^8$ or $C(O)R^8$; wherein $R^8$ is hydrogen, alkyl of $C_1-C_{15}$, alkenyl of $C_2-C_{15}$, alkynyl of $C_2-C_{10}$, haloalkyl of $C_1-C_{10}$, $R^9$, alkyl of $C_1-C_{15}$-$R^9$, alkenyl of $C_2-C_{15}$-$R^9$, alkynyl of $C_2-C_{15}$-$R^9$, or alkyl of $C_1-C_{15}$-O-$R^9$; wherein $R^9$ is aryl, heteroaryl, cycloalkyl, or heterocyclic any of which may be substituted or unsubstituted, or a radical of the formula $—R^{10}—[linker_{(0\ or\ 1)}—R^{10}]_{(0\ or\ 1)}$ wherein each $R^{10}$ independently represents phenyl, heteroaryl, cycloalkyl or heterocyclic, each of which is unsubstituted or optionally substituted with one or two substituents, each of which is independently alkyl of $C_1$–$C_{10}$, haloalkyl of $C_1$–$C_{10}$, haloalkoxy of $C_1$–$C_{10}$, alkoxy of $C_1$–$C_{10}$, halo, cyano, or nitro; and "linker" is: -alkylene of $C_1$–$C_3$-, -alkylene of $C_1$–$C_6$, -alkylene of $C_1$–$C_6$-O—, —O—, —N(H or lower alkyl of $C_1$–$C_6$)—, —S—, —SO—, —SO$_2$—, —O—SO$_2$—O—, —SO$_2$—O—, —NHC(O)—, —C(O)—, —C(O)NH—, —CH=CH—, —C≡C—, —N=N—, —OC(O), or —C(O)O—;

wherein $R^{11a}$ and $R^{11b}$ are independently selected from R, $R^1$ and $R^2$ with the proviso that $R^{11a}$ and $R^{11b}$ cannot both be hydrogen;

wherein Z is a substituent of the formula $YX^2R^{12}$, $N_3$, $N^+(R^{13})=CR^{14}R_{15}$, $N=PR^{13}R^{14}R^{15}$, $N^+R^{13}R^{14}R^{15}$ or $P^+R^{13}R^{14}R^{15}$ in which the group Y is a single bond, O, $NR^{12}$ or S; the group $X^2$ is O, $NR^{12}$, S, $SO_2$, C(O)O, C(O)S, C(S)O, C(S)S, $C(NR^{12})$, $C(O)NR^{12}$, or halo (in which case and $R_{12}$ are absent); $R_{12}$, $R_{13}$, $R_{14}$ and $R^{15}$ are independently R, $R^1$ or $R^2$ as defined above, provided that X and Y are not both O; X and Y are not S and O, or O and S, respectively;

or a pharmaceutically acceptable salt or ester of said compound.

In preferred compounds of the present invention, at least one of $R^{11a}$ or $R^{11b}$ is selected from the group consisting of 4-phenylbenzyl, 4-phenoxybenzyl, 4-benzyloxybenzyl, 4-(4-chlorophenyl)benzyl, 4-(4-chlorophenoxy)benzyl, 4-(4-chlorobenzyloxy)benzyl, 4-(3,4-dichlorophenyl)benzyl, 4-(3,4-dichlorophenoxy)benzyl and 4-(3,4-dichlorobenzyloxy)benzyl; and $R^1$ is —$(CH_2)_{1-9}NH_2$ and R is hydrogen. In particularly preferred compounds of the present invention, $R^1$ is —$(CH_2)_4NH_2$ or —$(CH_2)_2NH_2$. In other preferred compounds of the present invention, Z is one of hydroxyl, amino, azido, halo and hydrazino.

The present invention also directed to methods of making compounds of the formula above by reacting a compound of the formula

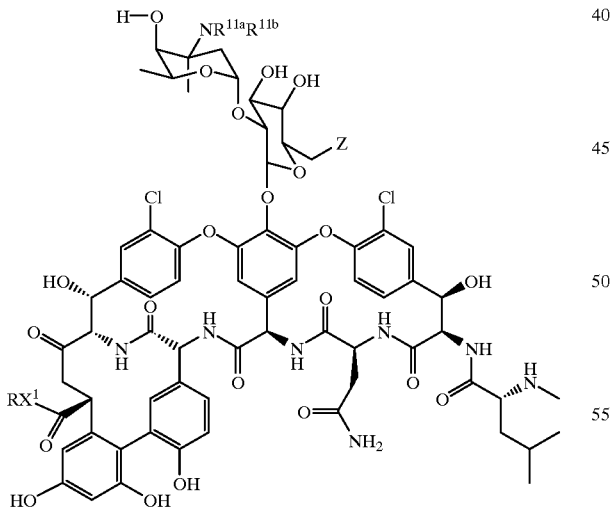

with a compound of the formula NHR—$[(CH_2)_mNR^3]_n$—Q—$[(CH)_kNR^4]_h$—$(CH_2)_p$—$NR^5R^6$ and optionally forming a salt or an ester thereof. The present invention is also directed to compositions comprising a compound of the present invention in combination with a pharmaceutically acceptable carrier or diluent, and optionally, one or more additional therapeutic agents. The present invention is also directed to a method of treating a bacterial infection in a host with a therapeutically effective amount of a compound of the present invention, or a composition of the present invention in combination with a pharmaceutically acceptable carrier or diluent, and optionally, one or more additional therapeutic agents.

DETAILED DESCRIPTION OF THE INVENTION

Functionalization of the Terminal Carboxyl Group

The preferred compounds of the present invention which are amide modifications of the terminal carboxyl group of vancomycin are prepared by reacting a vancomycin analog having a terminal carboxyl group and bearing a substituent —$NR^{11a}R^{11b}$ at the vancosamine nitrogen with an amine of the formula $HNRR^1$ wherein $R^1$ is a radical of the formula —$[(CH_2)_mNR^3]_n$—Q—$[(CH)_kNR^4]_h$—$(CH_2)_p$—$NR^5R^6$ wherein: any of $R^3$, $R^4$, $R^5$ and $R^6$ is hydrogen or linear or branched $(C_1$–$C_8)$alkyl that may optionally be substituted with one or more substituents each of which is independently selected from the group consisting of halo, nitro, cyano, loweralkoxy of $C_1$–$C_4$, halolower-alkyl of $C_1$–$C_4$, haloloweralkoxy of $C_1$–$C_4$, $NH_2$, OH or SH; or $R^5$ and $R^6$ taken together with the adjacent nitrogen atom, form a 5 to 7 membered saturated heterocyclic ring which may contain a further heteroatom selected from —S—, —O—, and $NR_7$ wherein $R^7$ is hydrogen, $(C_1$–$C_4)$alkyl, phenyl, or phenyl-$(C_1$–$C_4)$ alkyl; m, k and p, each independently represent and integer from 2 to 8; n and h, each independently, represent an integer from 0 to 4; Q represents a single bond, or when n is 1, taken together with the adjacent group $NR^3$, it may represent a bifunctional radical of the formula:

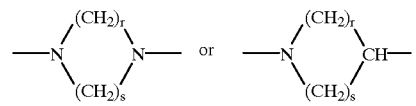

wherein r and s each independently represent an integer from 1 to 6 with the proviso that their sum is an integer from 3 to 8; and their addition salts with acids, and $R^{11a}$ and $R^{11b}$ are independently selected from R, $R^1$ and $R^2$ with the proviso that $R^{11a}$ and $R_{11b}$ cannot both be hydrogen. In this process, R is hydrogen, substituted or unsubstituted alkyl, aryl, aralkyl, alkanoyl, aroyl, aralkanoyl, heterocyclic, heterocyclic-carbonyl, heterocyclic-alkyl-carbonyl, alkylsulfonyl or arylsulfonyl, $R^1$ or $R^2$; and $R^2$ is —$CH_2R^8$ or $C(O)R^8$; wherein $R^8$ is hydrogen, alkyl of $C_1$–$C_{15}$, alkenyl of $C_2$–$C_{15}$, alkynyl of $C_2$–$C_{15}$, haloalkyl of $C_1$–$C_{10}$, $R^9$, alkyl of $C_1$–$C_{15}$-$R^9$, alkenyl of $C_2$–$C_{15}$-$R^9$, alkynyl of $C_2$–$C_{15}$-$R^9$, or alkyl of $C_1$–$C_{15}$-O—$R^9$; wherein $R^9$ is aryl, heteroaryl, cycloalkyl, or heterocyclic any of which may be substituted or unsubstituted, or a radical of the formula —$R_{10}$—[linker$_{(0\ or\ 1)}$—$R^{10}]_{(0\ or\ 1)}$ wherein each $R^{10}$ independently represents phenyl, heteroaryl, cycloalkyl or heterocyclic, each of which is unsubstituted or optionally substituted with one or two substituents, each of which is independently alkyl of $C_1$–$C_{10}$, haloalkyl of $C_1$–$C_{10}$, haloalkoxy of $C_1$–$C_{10}$, alkoxy of $C_1$–$C_{10}$, halo, cyano, or nitro; and "linker" is: -alkylene of $C_1$–$C_3$-, -alkylene of $C_1$–$C_6$, -alkylene of $C_1$–$C_6$-O-, —O—, —N(H or lower alkyl of $C_1$–$C_6$)—, —S—, —SO—, —SO$_2$—, —O—SO$_2$—O—, —SO$_2$—O—, —NHC(O)—, —C(O)—, —C(O)NH—, —CH=CH—, —C≡C—, —N=N—, —OC(O)—, or —C(O)O—;

The reaction is preferably conducted in the absence of water. Water can be removed from a mixture of the amine and the vancosamino-substituted compound by azeotropic distillation with toluene, for example. The terminal carboxyl group is first activated with, for example, HOBT, HBTU. The reaction of the activated terminal carboxyl group with the amine is carried out in a solvent such as DMF, DMSO, or a mixture of DMF and DMSO at a reaction temperature of from 0 to 100° C., although the reaction is conveniently carried out at room temperature. Generally, the reaction is conducted with equimolar proportions of the reactants or an excess of the amine. The resultant product can be isolated by precipitation or by lyophilization of the reaction mixture, and purified if desired in a conventional manner, such as by HPLC. The preferred amide derivatives will preferably bear at least one additional amino group. Amide derivatives bearing an additional amino group can be prepared by reacting, e.g. a diamino compound such as 1,4-diaminobutane (putrescine) or 1,2-diaminoethane (ethylene diamine) with the activated carboxyl group.

While the foregoing description is a preferred method of forming an amide at the terminal carboxyl group, i.e. by forming an activated ester intermediate followed by reaction with the amine, other methods of forming peptide bonds, i.e., amide linkages, are known to the ordinarily skilled chemist and may be employed as well, subject of course, to suitable protection of other groups in the molecule which might be reactive under the conditions employed to form the peptide linkage at the terminal carboxyl group. Thus, for example, the carboxyl group may be activated by reaction with, e.g., 1-ethyl-3-(3-dimethylaminopropyl)carbodiimide hydrochloride (EDC) to form an amine-reactive O-acylisourea intermediate, followed by reaction with an amine of the formula $HNRR^1$ to yield a compound of the present invention which is an amide modification of the terminal carboxyl group. The reaction of the carboxyl group with EDC and the subsequent reaction with the amine is conducted in a suitable solvent which may be aqueous, organic or a combination of aqueous/organic solvents. Exemplary solvents include, but are not limited to DMF, (dimethylformamide), methylene chloride, hexanes, methanol and mixtures thereof. Other compounds which activate the terminal carboxyl group in a manner similar to EDC include, for example, dicyclohexylcarbodiimide (DCC). Other protocols for activating a carboxyl group to render it more amenable to reaction with an amine to form a peptide linkage are known to the ordinarily skilled chemist and may be employed to form the amide modification of the terminal carboxyl group.

Among amines of the formula $HNRR^1$ that can be reacted with the terminal activated carboxyl of vancomycin substituted at the vancosamine nitrogen include, but are not limited to, the following:

$NH_2(CH_2)_2NH_2$;
$NH_2(CH_2)_3N(CH_3)_2$;
$NHCH_3(CH_2)_3\ N(CH_3)_2$;
$NHC_2H_5(CH_2)_3\ N(n-C_4H_9)_2$
$NH_2(CH_2)_3NH(n-C_8H_{17})$;
$NHCH_3(CH_2)_3NHCH_3$;
$NH_2(CH_2)_3NH(CH_2)_2OH$;
$NH_2(CH_2)_2NH(CH_2)_4SH$;
$NHCH_3(CH_2)_4\text{—}NC_2H_5(CH_2)_2NHC_2H_5$;
$NH_2(CH_2)_4NH_2$;
$NHCH_3(CH_2)_6N(CH_3)_2$;
$NHC_2H_5(CH_2)_5NH_2$;
$NH_2(CH_2)_2NH(CH_2)_2NH_2$;
$NH_2(CH_2)_3NH(CH_2)_3NH_2$
$NH_2(CH_2)_3N[(CH_2)_3NH_2]_2$;
$NH_2(CH_2)_3N[(CH_2)_3OH]_2$;
$NH_2(CH_2)_3NH(CH_2)_4NH_2$;
$NH_2(CH_2)_4NH(CH)_3NH_2$;
$NH_2(CH_2)_3NH(CH_2)_2NH(CH_2)_3NH_2$;
$NH_2(CH_2)_3NH(CH_2)_3NH(CH_2)_3NH_2$;
$NH_2(CH_2)_3NH(CH_2)_4NH(CH_2)_3NH_2$;
$NH_2(CH_2CH_2NH)_2CH_2CH_2NH_2$;
$NH_2(CH_2CH_2CH_2NH)_3CH_2CH_2CH_2NH_2$;
$NHCH_3(CH_2)_2NH(CH_2)_3N(CH_3)_2$;
$NHCH_3(CH_2)_3NCH_3(CH_2)_3N(CH_3)_2$;
$NHCH_3(CH_2)_3NH(CH_2)_4N(n-C_4H_9)_2$;
$NH_2(CH_2)_3NH(CH_2)_4NH(n-C_8H_{17})$;
$NH_2(CH_2)_3NH(CH_2)_4NH(CH_2)_3N(n-C_4H_9)_2$;
$NH_2(CH_2)_3NH(CH_2)_4NH(CH_2)_3N(n-C_8H_{17})_2$;
$NHCH_3(CH_2)_3NCH_3(CH_2)_3NCH_3(CH_2)_3NHCH_3$;
$NHCH_3(CH_2)_3NCH_3(CH_2)_3NCH_3(CH_2)_3N(n-C_4H_9)_2$;
$NH_2(CH_2)_3NN(CH_2)_3N(CH_2)_3N(CH_3)_2$;
$NH_2(CH_2)_3NN(CH_2)_3NH(n-C_8H_{17})$;
$NH_2(CH_2)_3NN(CH_2)_3N(n-C_4H_9)_2$
$NH_2(CH_2)_2\text{-}NN(CH_2)_2NHCH_3$ It is to be understood that while amide modifications of the terminal carboxyl group are the preferred compounds of the present invention, the invention is not to be construed as being limited to amide modifications of the terminal carboxyl group. Thus, within the scope of the present invention are included terminal esters, thioesters, and other carboxylic acid derivatives. Indeed, any conventional modification of an activated carboxyl group can yield compounds of the present invention. For example, a compound bearing a reactive —SH or —OH group may be reacted with the activated terminal carboxyl group, in a manner known to the ordinarily skilled organic chemist, to yield a wide variety of terminal esters and thioesters within the scope of the present invention.

Vancosamine Nitrogen Modification

The vancomycin analog bearing a vancosamine substituent of the formula $-NR^{11a}R^{11b}$ can be prepared by reductive alkylation of vancosamine nitrogen of vancomycin with an aldehyde of the formula $HC(O)R^{11a}$ or $HC(O)R^{11b}$ in a suitable organic solvent, followed by reduction of the aldehyde carbonyl group with a suitable reducing agent followed by conventional separation and purification, which may involve recrystallization and/or reverse phase chromatographic techniques as are well known to the ordinarily skilled chemist. Reductive alkylation is a technique well known to the ordinarily skilled organic chemist. Thus, the vancosamine nitrogen of vancomycin can be reacted with an aldehyde of the formula $HC(O)R_{11a}$ or $HC(O)R^{11b}$ to form an intermediate Schiff's base, which is subsequently reduced with a metal borohydride, e.g. $NaBH_3CN$ (sodium cyanoborohydride) to give the desired vancosamine substituent. For example, the reaction for the formation of the Schiff's base is carried out under an inert atmosphere, such as nitrogen or argon, in a polar solvent, such as dimethylformamide (DMF) or methanol (MeOH), or a mixture of polar solvents, such as a mixture of dimethylformamide and methanol, at a temperature of about 25° C. to about 100° C. The reaction is preferably carried out at a temperature from about 60° C. to about 70° C. for 30 minutes to 2 hours in a mixture of dimethylformamide and methanol, or in methanol. The intermediate Schiff's base is then reduced, preferably without isolation, to produce the corresponding N-alkyl derivative(s). The reduction of the Schiff's base can be effected using a chemical reducing agent such as a metal borohydride, for example, sodium borohydride or sodium cyanoborohydride. The reduction reaction can be carried out in a polar organic solvent, such as dimethylformamide, methanol, or a mixture of polar solvents, such as a mixture of dimethylformamide and methanol. The reduction reation is preferably carried out using an excess of sodium cyanoborohydride in a mixture of dimethylformamide and methanol or in methanol at about 60° C. to about 70° C. for 1 to 2 hours. Methods of reductive alkylation to modify the vancosamine nitrogen are disclosed in U.S. Pat. No. 5,840,684, which is incorporated herein in its entirety.

In some cases when conducting the reductive alkylation, it may be desirable to protect other reactive amino groups in the vancomycin parent compound, such as the amino group in the terminal N-methyl leucine residue thereof. Any amino protecting group may be employed and conventional methods of removing the amino protecting group may be employed to remove the protective group after performing the reductive alkylation at the vacosamine nitrogen. Representative examples of N-protecting groups which may be advantageously used in the process of the invention for suitably protecting desired amino groups from involvement in the reaction include compounds having oxycarbonyl groups such as, e.g., 1,1-dimethylpropynyloxycarbonyl, t-butyloxycarbonyl, vinyloxycarbonyl, aryloxycarbonyl, cinnamyloxycarbonyl, benzyloxycarbonyl, p-nitrobenzyloxycarbonyl, 3,4-dimethoxy-6-nitrobenzyloxycarbonyl, 2,4-dichlorobenzyloxycarbonyl, 5-benzisoxazolylmethyloxycarbonyl, 9-anthranylmethyloxy-carbonyl, diphenylmethyloxycarbonyl, isonicotinyloxycarbonyl, diphenylmethyloxycarbonyl, isonicotinyl-oxycarbonyl, S-benzyloxycarbonyl, 2,2,2-trichloro-ethoxycarbonyl, 2,2,2-trichloro-t-butoxycarbonyl, and the like.

While reductive alkylation is a preferred method of functionalizing the vancosamine nitrogen, other methods known to the ordinarily skilled artisan of coupling free amino groups to organic substituents can also be employed to functionalize the vancosamine nitrogen to form a substituent of the formula —NR$^{11a}$R$^{11b}$. Thus, the preferred methods of the present invention are not to be construed as being limited to reductive alkylation.

If a compound of the present invention is modified to bear a group other than a naturally occurring hydroxyl at the C6 position of the glucose residue directly attached to amino acid four of the heptapeptide chain, the C6 position is preferably modified prior to the reductive alkylation of the vancosamine nitrogen. Thus, by suitable protection of other reactive hydroxyl and amino groups, the vancomycin parent compound may initially be modified to selectively bear a mesitylene sulfonylgroup at the C6 glucose position. The mesitylene sulfonyl group may later be displaced with a nucleophile, e.g. a halo or azido group to form an initial displacement product that may be further functionalized by, e.g., reduction of the azido group to an amino group at the C6 position.

Reductive alkylation of the vancosamine nitrogen is preferably conducted prior to functionalization of the terminal carboxyl group of the heptapeptide chain to form a compound of the present invention. In a preferred sequence where the C6 position of the glucose reside is to be modified to bear a substituent other than a naturally occurring hydroxyl (such as an amino group), the C6 position of the glucose residue is preferably modified initially to bear a mesitylene sulfonyl group, reductive alkylation is then performed at the vancosamine nitrogen, the mesitylene sulfonyl group is then displaced, e.g., with an azido group, the terminal carboxyl group is functionalized and, finally, the azido group is reduced to an amino group at the C6 position of the glucose residue.

Among preferred substituents R$^{11a}$, R$^{11b}$ on the group of the formula —NR$^{11a}$R$^{11b}$ include, but are not limited to, the following:

2-naphthylmethyl
4-phenylbenzyl
1-naphthylmethyl
4-phenoxybenzyl;
4-benzyloxybenzyl
4-trifluoromethoxybenzyl
4-allyloxybenzyl
4-nonyloxybenzyl;
2-methoxy-1-naphthylmethyl
4-dodecyloxybenzyl
9-phenanthranylmethyl
4-decyloxybenzyl
9-anthranylmethyl
4-[phenylethynyl]4-phenylbenzyl
4-methoxy-1-naphthylmethyl
1-pyrenylmethyl
9-[10-methyl]anthranylmethyl
9-[10-chloro]anthranylmethyl
2-benzthienylmethyl
4-[4-hydroxyphenyl]benzyl
4-[4-octylphenyl]benzyl
4-[4-pentylphenyl]benzyl
4-[4-octyloxyphenyl]benzyl
3-pyridylmethyl
5-nitro-1-naphthylmethyl
4-pyridylmethyl
4-quinolylmethyl
3-quinolylmethyl
4-stilbenzyl
2-quinolylmethyl
2-pyridylmethyl
2-fluorenylmethyl
4-phenoxyphenethyl
4-[4-pentylcyclohexyl]benzyl
4-benzylphenethyl
4-[4-biphenyl]benzyl
4-trifluoromethylbenzyl
trans-cinnamyl
4-[1-oxa]fluorenylmethyl
4-[4-pentoxyphenyl]benzyl
4-thiomethylbenzyl
2,3-[2-methyl-3-[4-t-butylphenyl]]propenyl
9-(1-methyl)-acridinylmethyl
2-hydroxy-1-naphthylmethyl
4-[2-phenyl-6-methoxy]quinoylmethyl
4-diphenylmethylbenzyl
3,4 cyclohexenylmethyl
3,4-methylenedioxylbenzyl 3-phenoxybenzyl
4-benzylbenzyl
3-benzyloxy-6-methoxy benzyl
4-benzyloxy-3-methoxybenzyl
3,4-dibenzyloxybenzyl
4-[4-methoxyphenyl]benzyl
4-[3-cyanopropoxy]benzyl
3,4-ethylenedioxybenzyl
4-[4-nitrophenoxy]benzyl
2,3-methylenedioxybenzyl
2-benzyloxyphenethyl
2-ethoxy-1-naphthylmethyl
2-benzylfurylmethyl
3-phenoxyphenethyl
4-phenoxyphenethyl
4-[4-nitrophenyl]benzyl
6-methoxy-2-naphthylmethyl
3-methyl-5-thienylmethyl
5-phenyl-2-thienylmethyl
4-benzyloxyphenethyl
3-benzyloxyphenethyl
4-[2-nitrophenoxy]benzyl
5-[4-methoxyphenyl]-2-thienylinethyl
4-difluormethoxybenzyl
2,3,4,5,6-pentamethylbenzyl
5-iodo-2-thienylmethyl
4-[2-[2-chloroethoxy]ethoxy]benzyl
3,4-dimethylbenzyl
3-acetoxybenzyl
4-nitrobenzyl
4-phenylethynylbenzyl
4-[2-chloro-6-fluorobenzyloxy]benzyl
4-[3,4-dichlorophenoxy]benzyl
4-[3,4-dichlorobenzyloxy]benzyl
S-[2,3-dihydrobenzfiyl]methyl
4-[2-[N,N-diethylamino]ethoxy]benzyl
2-bicyclo[2.1.2]heptylmethyl
2-hydroxy-5-phenylbenzyl
3-[4-chlorophenoxy]benzyl
4-[3-chlorophenoxy]-3-nitrobenzyl
4-[2-chlorophenoxy]-3-nitrobenzyl
3,5-dimethylbenzyl
4-[4-ethylphenyl]benzyl
3-phenylbenzyl
4-[3-fluorophenyl]benzyl
4-[4-chlorobenzyloxy]benzyl
4-[4-chlorophenoxy]-3-nitrobenzyl
4-[4-methylphenoxy]benzyl
4-[4-t-butylphenoxy]benzyl
4-[4-methylphenyl]benzyl
4-[4-methoxyphenoxy]benzyl
4-acetoxy-3-methoxybenzyl
4-[(2-phenyl)ethyl]benzyl
3-[5-phenyl]pyridinylmethyl
4-[2-nitrophenyl]benzyl
2-[1-hydroxy] fluorenylmethyl
4-benzyl-3-methoxybenzyl
4-[cyclohexylmethoxy]-3-ethoxybenzyl
3-[3,3'-dichlorophenoxy]benzyl
4-[4-propylphenyl]benzyl
4-thiophenylbenzyl
4-[alpha-hydroxybenzyl]benzyl
2,2-dinitro-4-thiophenebenzyl
3-[3-trifluoromethylphenoxy]benzyl
4-[t-butylethynyl]benzyl
4-phenoxy-3-methoxy-benzyl
4-[3-trifluoromethylphenoxy]-3-nitrobenzyl
2-phenylthiobenzyl
2-[4-chlorophenyl]-6-benzoxazolemethyl
4-[alpha-methoxybenzyl]benzyl
4-cyclohexylbenzyl
3-[3,4-dichlorophenoxy]benzyl
acenaphthlenylmethyl
4-[1,1,2,2-tetrafluoroethoxy]benzyl
4-benzoyloxy-3,3-dimethoxybenzyl
3-[cyclohexylmethoxy]benzyl
4-cyclohexyloxybenzyl
3-[2-quinoylmethoxy]benzyl
4-[alpha-ethoxybenzyl]benzyl
4-[cyclohexylethoxy]benzyl
4-[alpha-propoxybenzyl]benzyl
4-[4-methyl-1-piperidino]benzyl
2-thiophene-1,2-cyclohexenylmethyl
4-[4-nitrobenzyloxy]benzyl
3-[4-trifluoromethylphenoxy]benzyl
3-benzoyl-2,4-dichlorobenzyl
4-[2-[2-thiopropyl]ethoxy]benzyl
4-[2-methyl-1-piperidino]benzyl
4-hydroxybenzyl
4-[2-pyridyl]benzyl
4-acetoxybenzyl
5,6-benzonorbornylmethyl
3-phenylcyclopentylmethyl
1-adamantylmethyl
3-[cyclohexylmethoxy]-4-methoxybenzyl
2-[2-glucosyl]benzyl
4-[4-pentoxybiphenyl]benzyl
3,4-dihydroxybenzyl
4-[4-methylpiperazino]benzyl
4-morpholinobenzyl
4-[4-chlorophenylsulfonyl]benzyl
4-methylsulfonyloxybenzyl
4-benzoyloxybenzyl
5-phenyl-3-pyridinylmethyl
4-[N,N-bis(2-chloroethyl)amino]benzyl
3-cyclohexyloxybenzyl
4-[2-t-butoxyethoxy]benzyl
3,3-dichloro-4-hydroxy-benzyl
1,2,3,4,-tetrahydro-9-anthranylmethyl
4-cyclohexanoyloxybenzyl
4-nonanoyloxybenzyl
4-[phenylsulfinyl]benzyl 4-anilinobenzyl
cyclohexylmethyl
3-benzoyloxybenzyl
3-nonanoyloxybenzyl
4-[cyclohexyl]cyclohexylmethyl
3-cyclohexanoyloxybenzyl
4-[cyclohexanoyloxy]-3,3-[dimethoxy]benzyl
4-[nonanoyloxy]-3,3-[dimethoxy]benzyl
1,2,3,4-tetrahydro-6-naphthylmethyl
2-hydroxybenzyl
[2-[6,6-dimethyl-bicyclo[3.1.1]hept-2-enyl]methyl
1-cyclohexenyl-4-isopropylmethyl
4-[4-methoxyphenyl]butyl
4-[[2,3,4,5,6-pentamethyl]phenylsulfonyloxy]benzyl
4-[1-pyrrolidinosulfonyl]benzyl
3-[4-methoxyphenyl]propyl
8-phenyloctyl
4-[2,3-dihydroxypropoxy]benzyl
4-[N-methylanilino]benzyl
2-[2-napthyl]ethyl
6-methyl-2-naphthylmethyl
cis-bicyclo[3.3.0]octane-2-methyl
2-tridecynyl
4-butyl-2-cyclohexylmethyl
4-[(4-fluorobenzoyl)amino]benzyl
4-[(3-fluorobenzoyl)amino]benzyl
8-phenoxyoctyl
6-phenylhexyl
10-phenyldecyl
8-bromooctyl
11-tridecynyl
8-[4-methoxyphenoxy]octyl
8-[4-phenylphenoxy]octyl
8-[4-phenoxyphenoxy]octyl
3-[3-trifluoromethylphenoxy]benzyl
10-undecenyl
4-cyclohexylbutyl
4-phenyl-2-fluorobenzyl
7-hexadecynyl
3-[cyclopentyl]propyl
4-[2-methylphenyl]benzyl
4-[phenylazo]benzyl
4-[4-flurophenyl]benzyl
3-nitro-4-[4-nitrophenyl]benzyl
3-nitro-4-[2-nitrophenyl]benzyl
9-decenyl
4-[3,4-dimethoxyphenyl]benzyl
4-[4-trifluromethylphenyl]benzyl
5-hexenyl
4-[2-thienyl]benzyl
4-[6-phenylhexyloxy]benzyl
9,10-dihydro-2-phenantrene methyl
4-[3,4-dimethylphenyl]benzyl
4-[4-methylphenyl]-2-methylbenzyl
4-[3-phenylpropyloxy]benzyl
4-[3-methylphenyl]benzyl
4-[4-methylphenyl]-3-methylbenzyl
4-[4-pentenyloxy]benzyl
4-[1-heptynyl]benzyl
3-[4-t-butyl-phenylthio]benzyl
4-[4-chlorophenyl]benzyl
4-[4-bromophenyl]benzyl
4-[4-cyanophenyl]benzyl
4-[1-nonynyl]benzyl
4-[1-tridecynyloxy]benzyl
12-phenyldodecyl
6-phenyl-5-hexynyl
11-phenyl-10-undecynyl
4-[2-methylphenyl]-3-methylbenzyl
3-[2-thienyl]-2-thienylmethyl
4-[benzyloxymethyl]cyclohexylmethyl
4-[4-chlorophenoxy]benzyl
4-[benzyl]cyclohexylmethyl
4-benzoylbenzyl
4-[phenoxymethyl]benzyl
4-[4-chlorobenzyl]benzyl Functionalization of the C6 Position of the Glucose Residue The compounds of the present invention may also bear a substituent Z at the C6 position of the glucose residue directly attached to amino acid four in the heptapeptide chain of vancomycin wherein Z is a substituent of the formula $YX^2R^{12}$, $N_3$, $N_+(R^{13})=CR^{14}R^{15}$, $N=PR^{13}R^{14}R^{15}$, $N^+R^{13}R^{14}R^{15}$ or $P^+R^{13}R^{14}R^{15}$ in which the group Y is a single bond, O, $NR^{12}$ or S; the group $X^2$ is O, $NR^{12}$, S, $SO_2$, C(O)O, C(O)S, C(S)O, C(S)S, C($NR^{12}$), C(O)$NR^{12}$, or halo (in which case and $R^{12}$ are absent); $R^{12}$, $R^{13}$, $R^{14}$ and $R^{15}$ are independently R, $R^1$ or $R^2$ as defined above, provided that X and Y are not both O; X and Y are not S and O, or O and S, respectively. The C6 position is preferably modified prior to modification of the vancosamine residue to bear a substituent of the —$NR^{11a}R^{11b}$ by reductive alkylation as described hereinabove, but may also be modified subsequent to the modification of the vancosamine nitrogen.

In preferred methods of the present invention, the C6 position is initially modified to bear a group such as mesitylenesulfonyl which may then be displaced by, e.g., nucleophilic substitution with a nucleophile such as an azido group, and the displacement group may be further functionalized by, e.g., reduction of the azido group. The reduction of the azido group is preferably conducted after the reductive alkylation at the vancosamine nitrogen and amidation or other functionalization of the terminal carboxyl group. Thus, for example, where the vancosamine bears a substituent of the formula —$NR^{11a}R^{11b}$ and the terminal carboxyl group has been amidated to form an amide of the formula —C(O)$NRR^1$, the C6 position of the glucose residue may bear an azido group, which is then reduced to form the corresponding amino group. The amino group at C6 may then, of course, be further functionalized by means of reductive alkylation in a manner similar to that as described in connection with the vancosamine nitrogen, by nucleophilic substitution or other amino-group reactions well known to those skilled in the art.

Where the C6 position of the glucose directly attached to amino acid four of the heptapeptide chain is to be modified to bear the mesitylensulfonyl group, which may be later displaced, the amine nitrogen of the terminal N-methyl leucine residue and the vancosamine nitrogen are suitably protected with, e.g., aloc groups by reaction of vancomycin HCl with N-(allyloxycarbonyloxy)succinimide or other suitable protecting group in the presence of NaHCO$_3$. The amino protecting groups, e.g., may be any of those as disclosed herein with respect to the functionalization of the vancosamine nitrogen, as well as any covnentional amino protecting groups known to the ordinarily skilled artisan. The reaction is preferably carried out in an organic solvent or solvent mixture with water for 1 to 48 hours at a temperature of from 0C to 100° C. Separation and purification yields the protected intermediate N,N'-diallyloxycarbonyl vancomycin. To protect the terminal carboxyl group, the N,N'-diallyloxycarbonyl vancomycin is then reacted with allyl bromide or other suitable protecting group in the presence of NaHCO$_3$ in DMSO under an argon atmosphere. The reaction is preferably carried out at a temperature of from 0° C. to 100° C. for 1 to 48 hours. Separation and purification yields the protected intermediate N,N'-diallyloxycarbonyl vancomycin allyl ester. The protected intermediate N,N'-diallyloxycarbonyl vancomycin allyl ester is then reacted with mesitylensulfonyl chloride in pyridine at a temperature of about 4° C. for about 24 hours to yield the compound N,N'-diallyloxycarbonyl C6-mesitylenesulfonyl vancomycin allylester which is separated and purified.

The mesitylenesulfonyl group of N,N'-diallyloxycarbonyl C6-mesitylenesulfonyl vancomycin allylester can then be displaced by a wide variety of nucleophilic groups. Thus, e.g., the mesitylenesulfonyl group can be displaced with an azido group by reacting with NaN$_3$ in DMF at, e.g. 80° C. to 85° C. for about 5 hrs. The resultant compound is then separated and purified. The azido group can then be reduced to an amino group by reduction with triphenylphospine in THF/water at, e.g., about 60° C. for about 14 hours. The resultant vancomycin analog bearing an amino group at the C6 position of the glucose residue directly attached to amino acid four of the heptapeptide chain is then separated and purified, and the amino group (aloc) and carboxyl (allyl) protecting groups are removed by conventional methods such as by exposure to acidic or basic conditions, catalytic hydrogenation or light. The preferred method of removing protecting groups is as follows: aloc groups on amines and allyl esters or allyl ethers are removed by using Pd(0) mediated reactions, e.g., [Ph$_3$P]$_2$Pd(II)Cl$_2$ and Bu$_3$SnH in 1:1 acetic acid:DMF. Acetate protecting groups are removed using hydrazine in THF/methanol.

The mesitylenesulfonyl group of N,N'-diallyloxycarbonyl C6-mesitylenesulfonyl vancomycin allylester can also be displaced by numerous other nucleophiles to yield preferred C6 substituents on the compounds of the present invention. Thus, e.g, N,N'-diallyloxycarbonyl C6-mesitylenesulfonyl vancomycin allylester can be reacted with hydrazine to form a hydrazino subsituent at the C6 position; with potassium iodide (or other halide) to form a halo substituent at the C6 position, etc. Included among the preferred substituents at the C6 position of the glucose residue directly attached to amino acid four of the heptapeptide chain are, e.g., amino, azido, hydrazino, iodo, mesitylenesulfonyl. It is to be understood that the compounds of the present invention do not need to be functionalized at the C6 position of the glucose residue. Thus, the compounds of the present invention include those compounds in which the C6 position of the glucose residue is hydroxyl. Hydroxyl is the naturally occurring group at the C6 position of the glucose residue directly attached to amino acid four in the heptapeptide chain of vancomycin.

An amino group at the C6 position can be functionalized by reductive alkylation, nucleophilic substitution or other amino group reactions known to the person having ordinary skill in the art.

Pharmaceutical formulations of the compounds of the present invention are also a part of the present invention, as well as the use of the compounds and formulations thereof to treat infectious diseases in mammals, preferably humans, comprising administering an amount of the compound of the present invention or a pharmaceutically acceptable salt or ester thereof to a mammal, the amount being effective to treat the infectious disease.

Thus, the compounds of the present invention, or pharmaceutically acceptable salts or esters thereof can be formulated for any conventional means of delivery, including oral or parenteral delivery for the therapeutical or prophylactic treatment of infectious diseases, preferably bacterial diseases. The bacterial diseases which may be therapeutically or prophylactically treated with the compounds and/or formulations of the present invention include those caused by Gram-positive and/or Gram-negative microorganisms.

The compounds of the present invention may be administered separately or in combination with any other drug or therapeutic agent. Examples of other therapeutic agents and/or drugs that can be administered with the compounds and/or formulations of the present invention include, but are not limited to, beta lactam antibiotics, such as penems, penams, cephems, carbapenems, oxacephems, carbacephems, and monobactams, or other antibiotics such as cycloserine and fosfomycin. The other therapeutic agent need not be an antibiotic.

The compounds and/or formulations are administered to the mammal in a therapeutically effective amount, which amount is effective to treat, prevent, mitigate and/or alleviate the infectious disease. Thus, the compound of the present invention can be administered to the mammal, preferably a human, in an amount ranging from about 0.5 to about 2 grams per day. The compounds and/or formulations of the present invention can be administered in a single daily dosage or in multiple doses per day. Other periodic treatment protocols may also be adopted. Thus, the treatment protocol may require administration over extended periods of time, e.g., for several days or for from about one to six weeks. The therapeutically effective amounts of the compound of the invention discussed above are merely exemplary. Thus, the amount per administered dose or the total amount administered will depend on such factors as the nature and severity of the infection, the age and general health of the patient, the tolerance of the patient to the compounds and/or formulations of the present invention and the microorganism or microorganisms involved in the infection.

In the pharmaceutical formulations of the present invention, the compound can be admixed with any conventional pharmaceutical carriers and/or excipients and can be formulated for immediate or sustained release. Other time-release profiles, such as combinations of immediate and sustained release are also possible. Thus, the compound of the present invention can be admixed with conventional pharmaceutical carriers and excipients and used in the form of tablets, capsules, caplets, elixirs, suspensions, syrups, wafers and the like. The compounds of the present invention can also be formulated for topical administration. Typical excipients and/or carriers include, but are not limited to corn starch, gelatin, lactose, sucrose, microcrystalline cellulose, kaolin, mannitol, dicalcium phosphate, sodium chloride, and alginic acid. Disintegrators commonly used in the formulations of this invention include croscarmellose sodium, microcrystalline cellulose, corn starch, sodium starch glycolate and alginic acid. Tablet binders that can be included are acacia, methylcellulose, polyvinylpyrrolidone, hydroxypropyl methylcellulose, sucrose, starch and ethylcellulose. Lubricants that can be used include magnesium stearate or other metallic stearates, stearic acid, silicone fluid, talc, waxes, oils and colloidal silica. Flavoring agents such as peppermint, oil of wintergreen, cherry flavoring or the like can also be used. It may also be desirable to add a coloring agent to make the dosage form more esthetic in appearance or to help identify the product. Tablets may be coated to facilitate swallowing or to modify release of the active compound, or some combination of these.

The compounds and/or formulations can also be administered intravenously or intramuscularly. For intravenous (IV) use, a water-soluble form of the compound is preferably dissolved in one of the commonly used intravenous fluids, and administered by infusion. Such fluids as, for example, physiological saline, Ringer's solution or 5% dextrose can be used. For intramuscular preparations, a sterile formulation of a suitable salt or ester form of the compound of the present invention, for example the hydrochloride salt form can be dissolved and administered in a pharmaceutical diluent such as water-for-injection, physiological saline or 5% glucose solution. A suitable insoluble form of the compound may be prepared and administered as a suspension in an aqueous base or a pharmaceutically acceptable oil base, such as an ester of a long chain fatty acid such as ethyl oleate.

For oral use, a sterile formulation of a suitable salt or ester form of the compound, for example, the hydrochloric acid salt, formulated in a diluent such as distilled or deionized water is particularly useful. Alternatively, the unit dosage form of the compound can be a solution of the compound, preferably in its salt or ester from, in a suitable diluent in sterile, hermetically sealed ampoules.

The following diagrams illustrate preferred reaction steps used in methods of making compounds of the present invention.

6-Amino-N-4-(3,4-dichlorobenzyloxyl)benzyl vancosamino vancomycin putrescine amide:

A. Protection of Vancosamine Nitrogen, N-methyl leucine Nitrogen and Terminal Carboxyl Groups

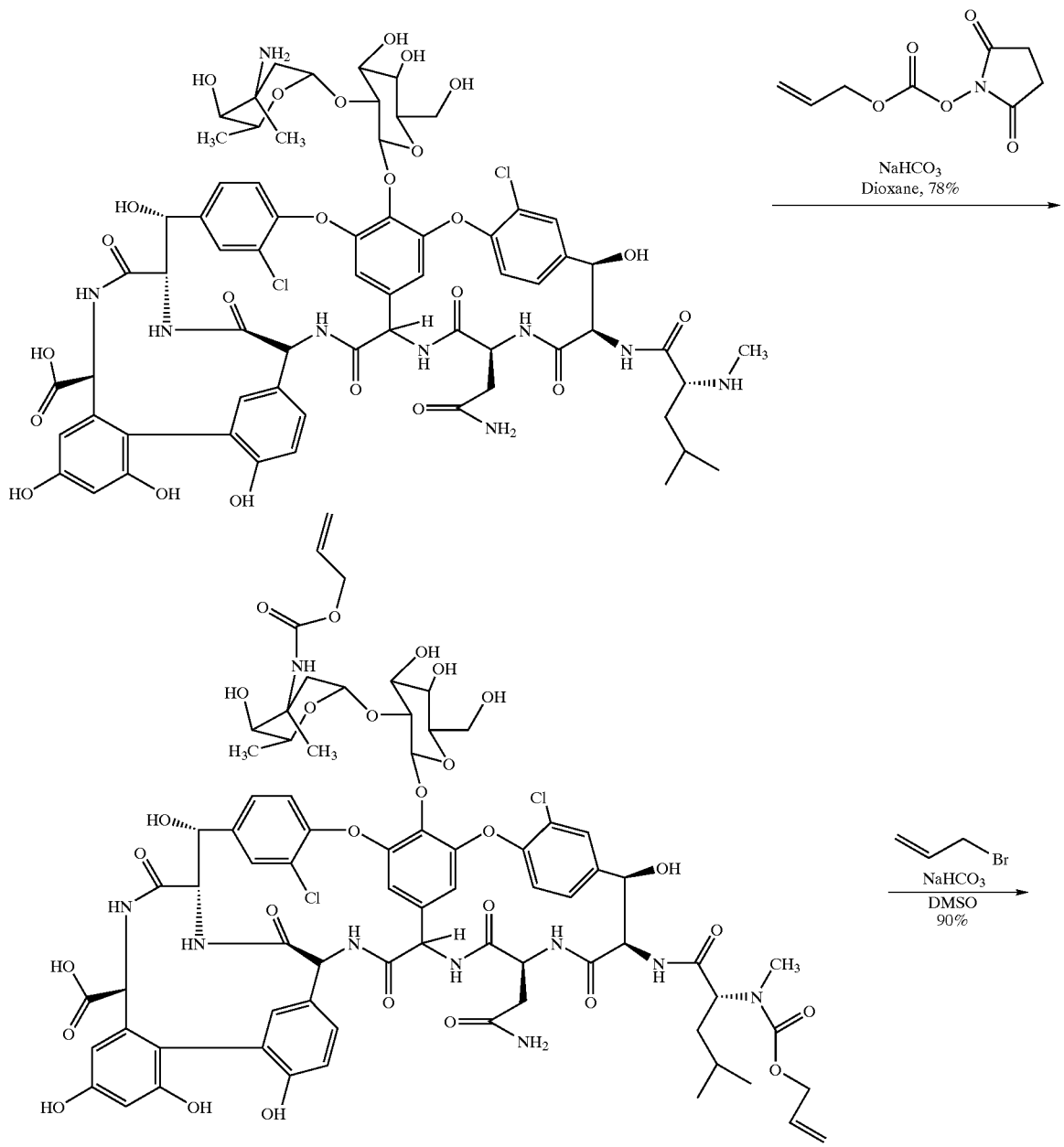

-continued
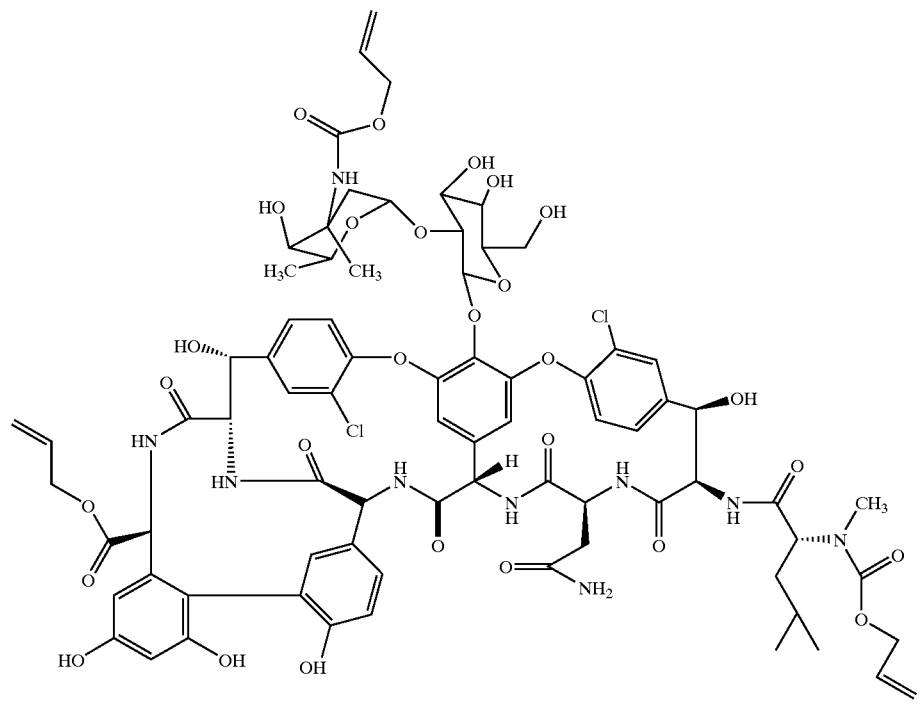
B. Functionalization of the C6 Position of the Glucose Residue with Mesitylene
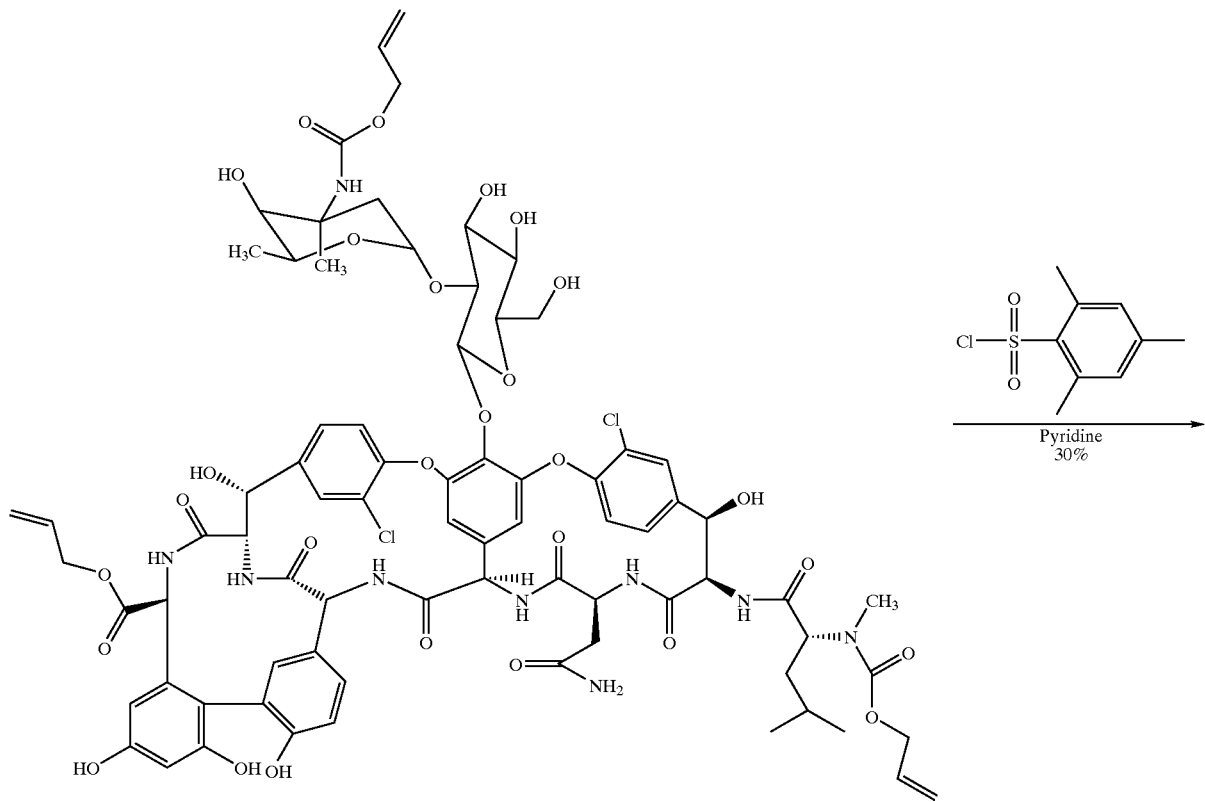

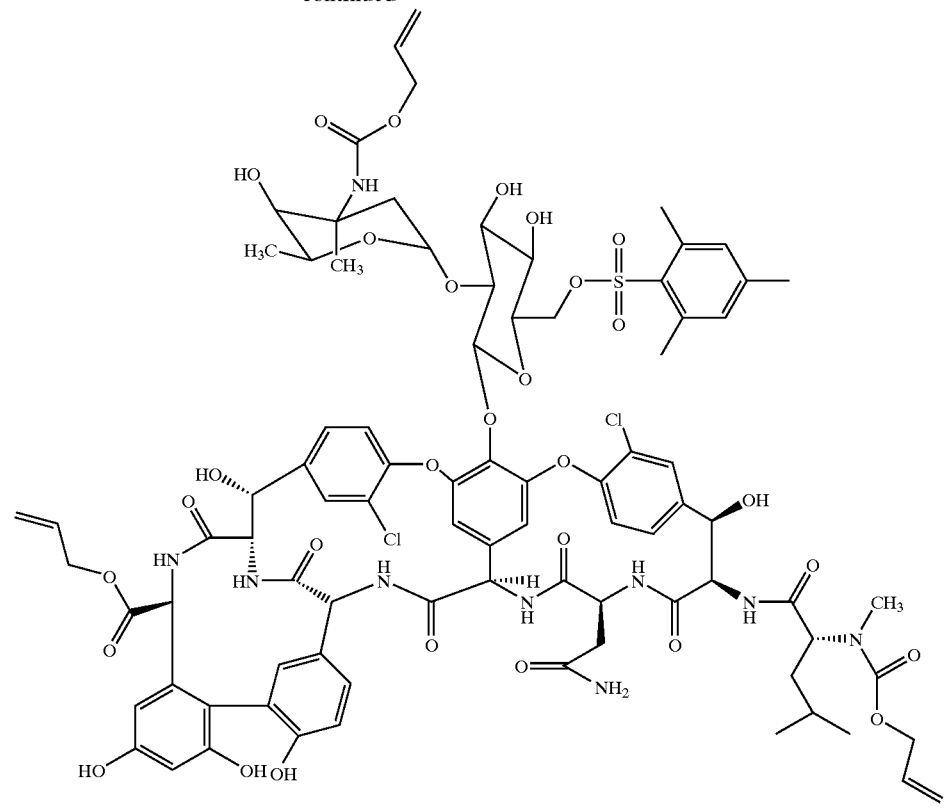
-continued
C. Deprotection of Vancosamine Nitrogen, N-methyl leucine Nitrogen and Terminal Carboxyl Group
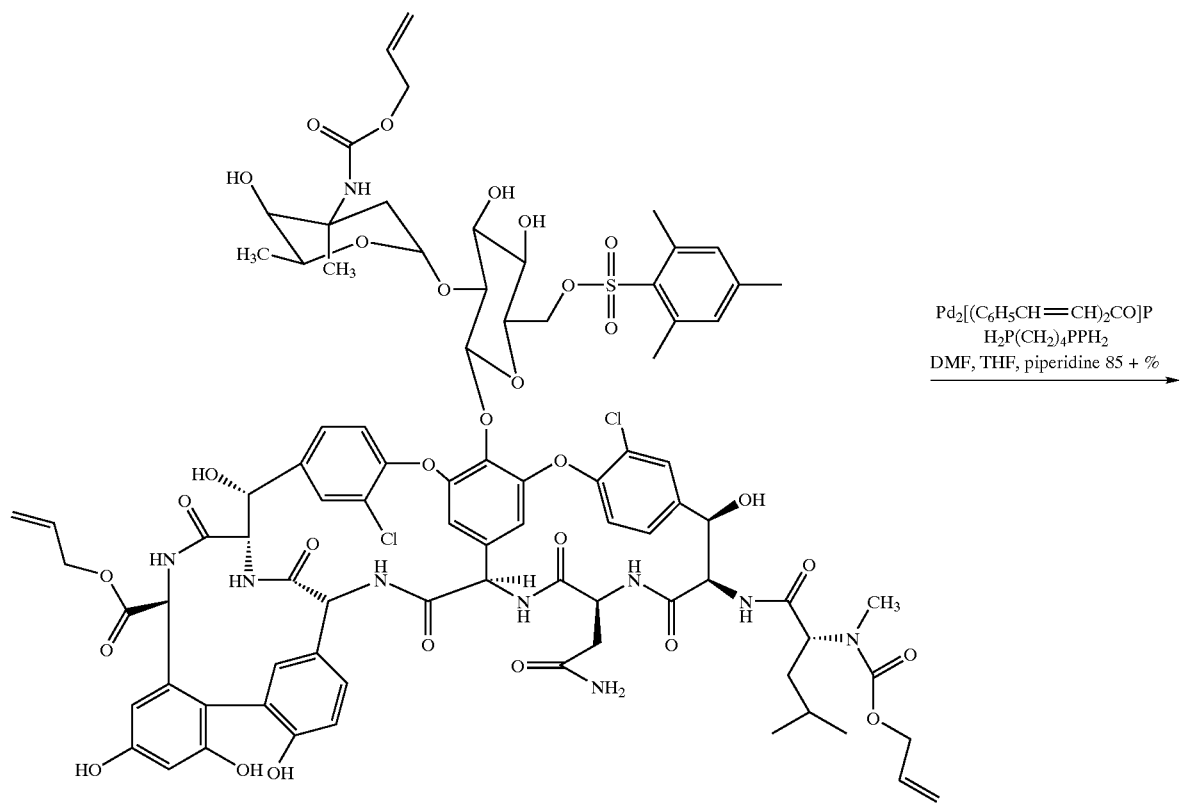
$Pd_2[(C_6H_5CH=CH)_2CO]P$
$H_2P(CH_2)_4PPH_2$
DMF, THF, piperidine 85 + %

-continued
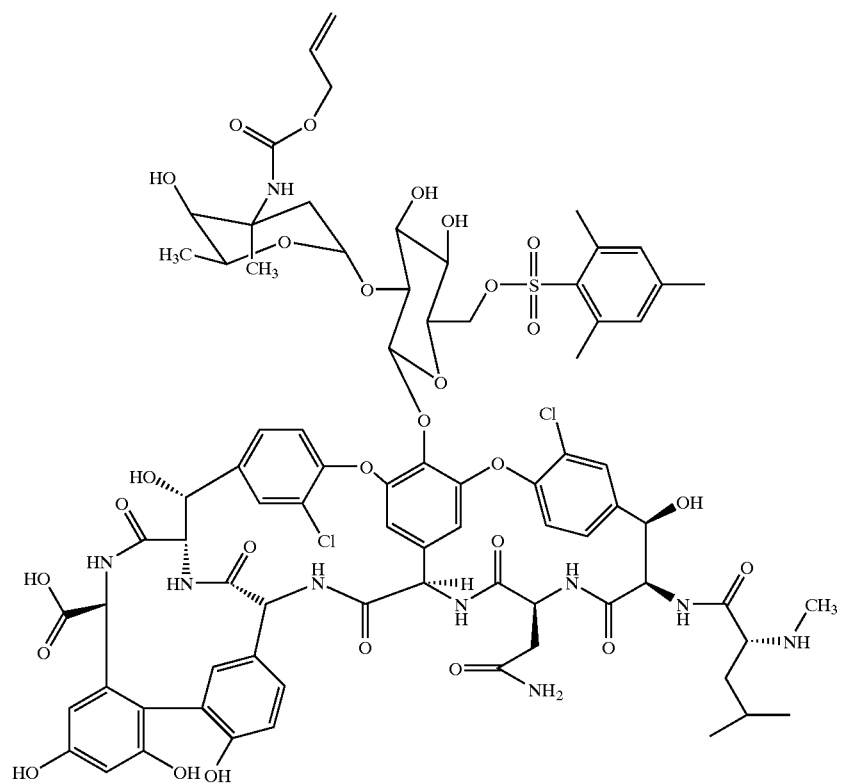
D. Reductive Alkylation of Vancosamine Nitrogen
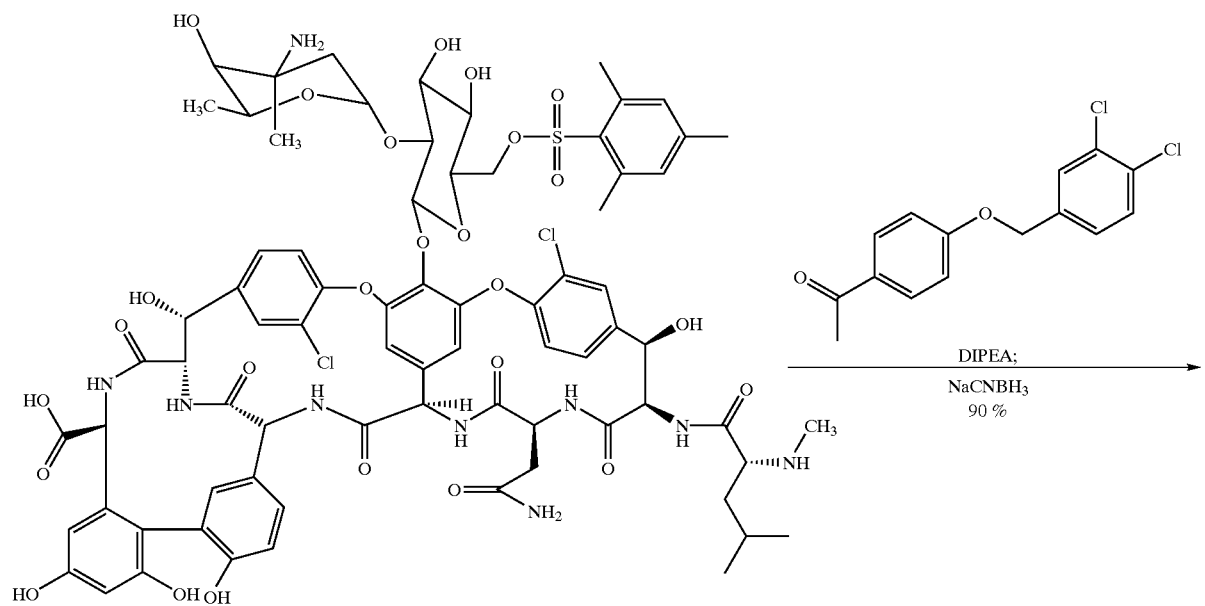

-continued
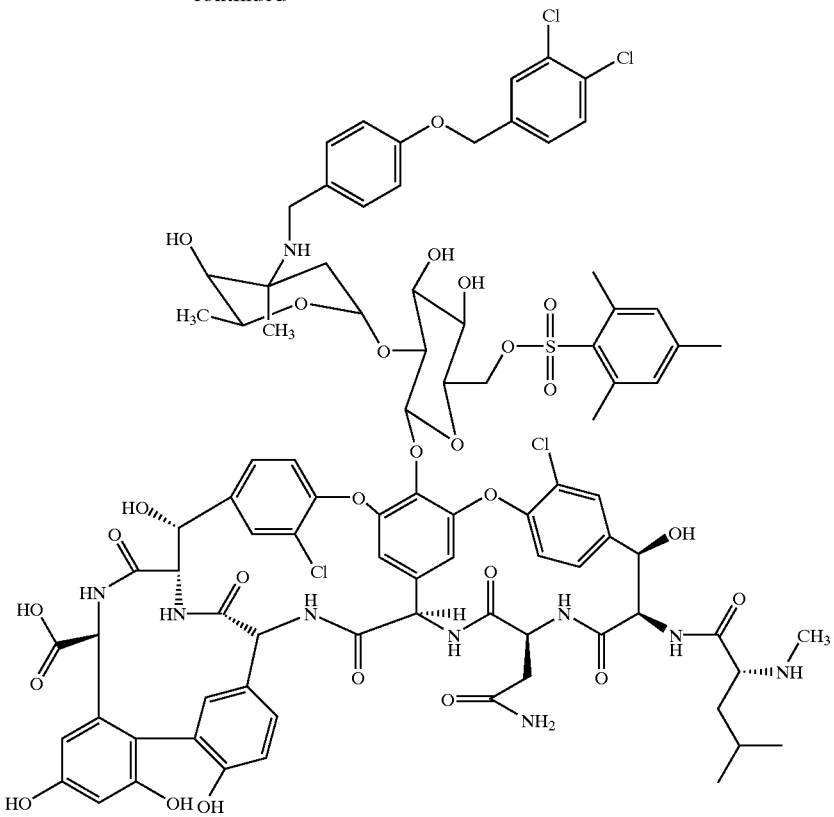
352-22
E. Displacement of Mesitylene Sulfonyl with Azido
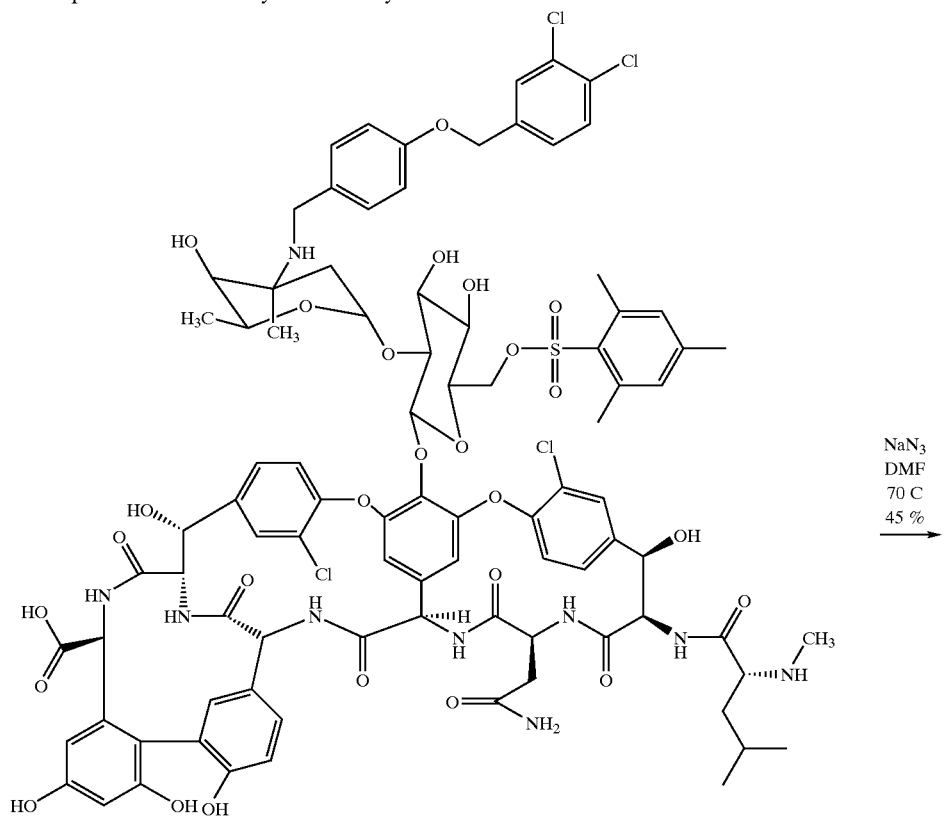
352-22
NaN₃
DMF
70 C
45 %

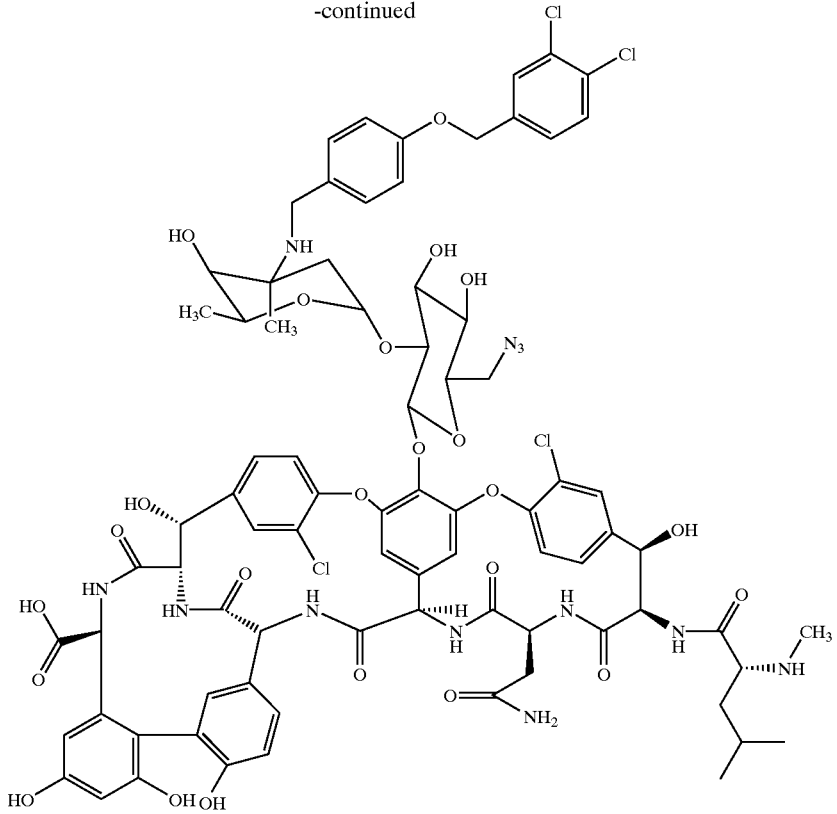
352-25
F. Functionalization of Terminal Carboxyl Group with Putrescine
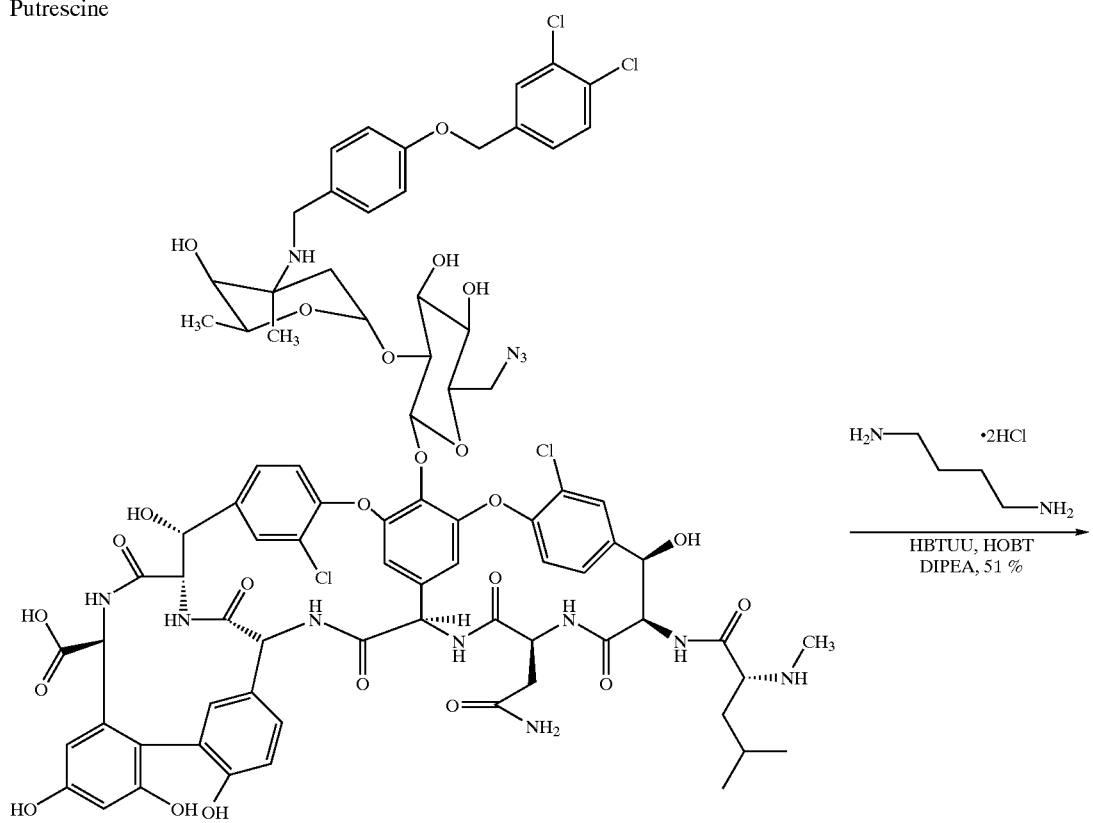
352-25

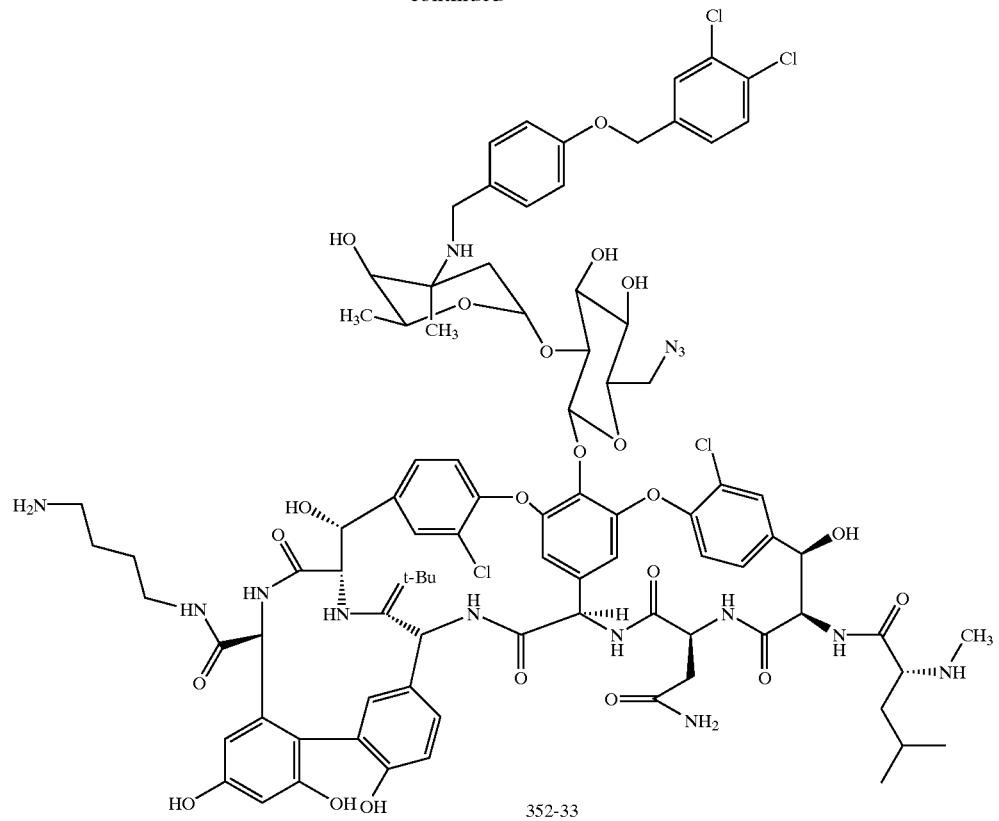
352-33
G. Reduction of Azido Group
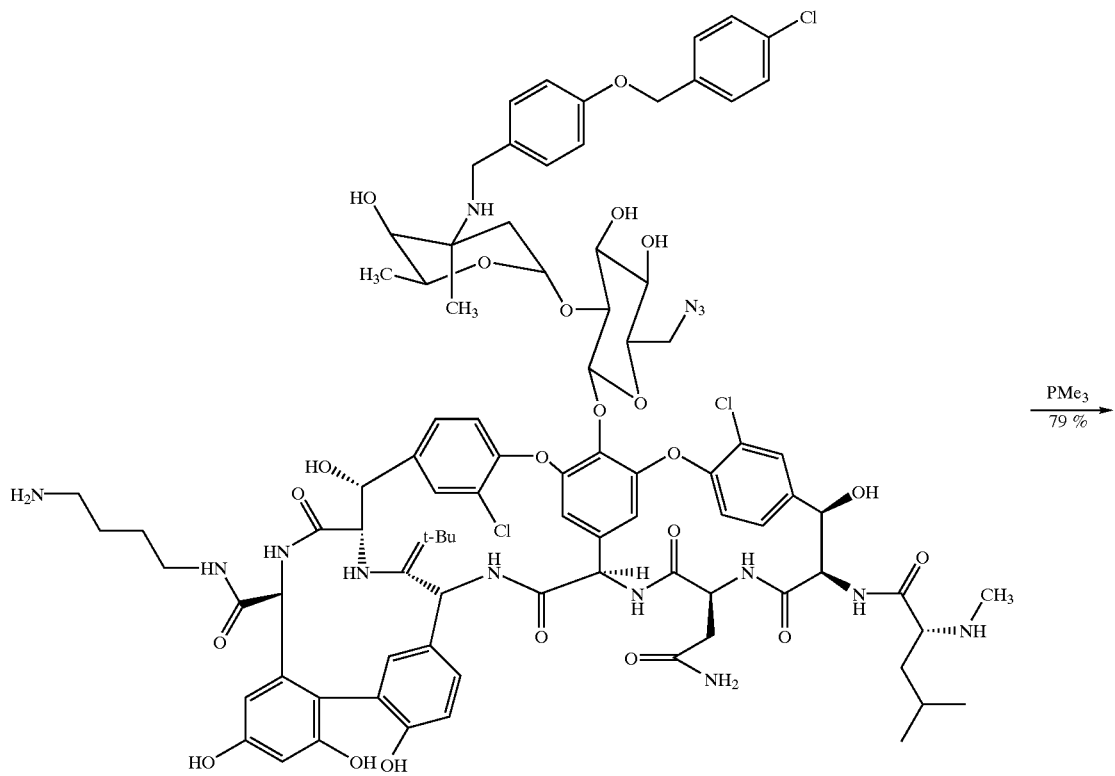
352-33

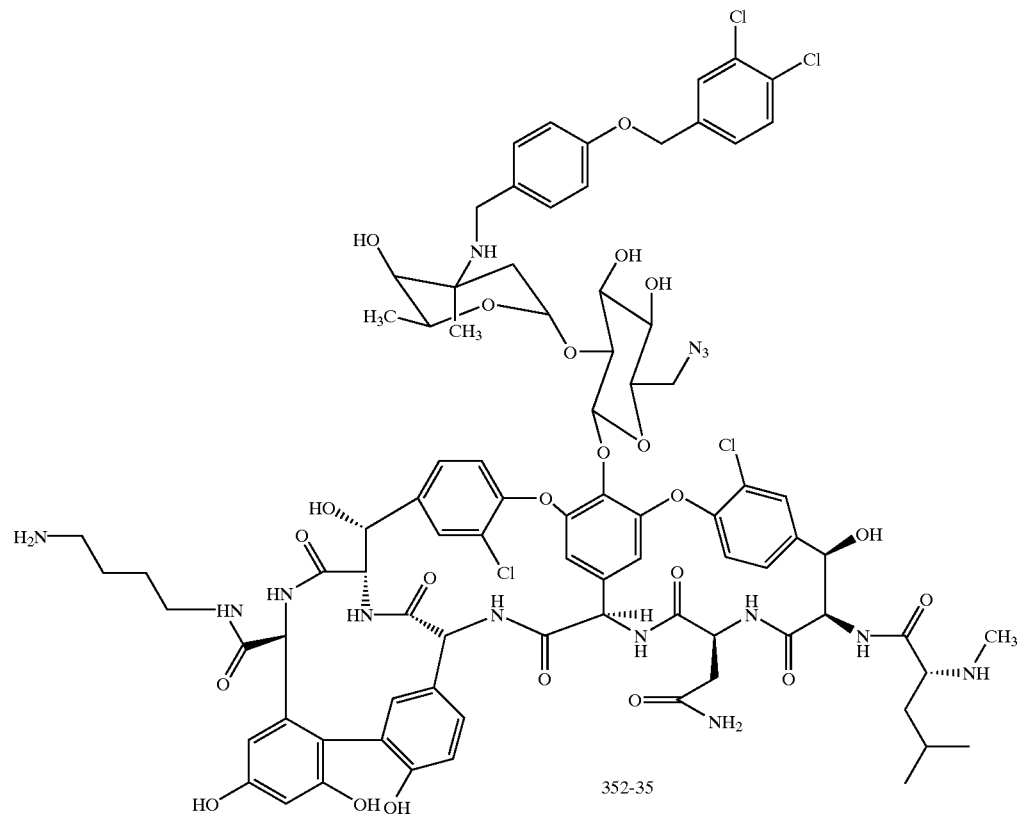
352-35
6-Amino-N-4-(4-chlorophenyl)benzyl vancosamino vancomycin putrescine amide:
A. Protection of Vancosamine Nitrogen, N-methyl leucine Nitrogen and Terminal Carboxyl Groups
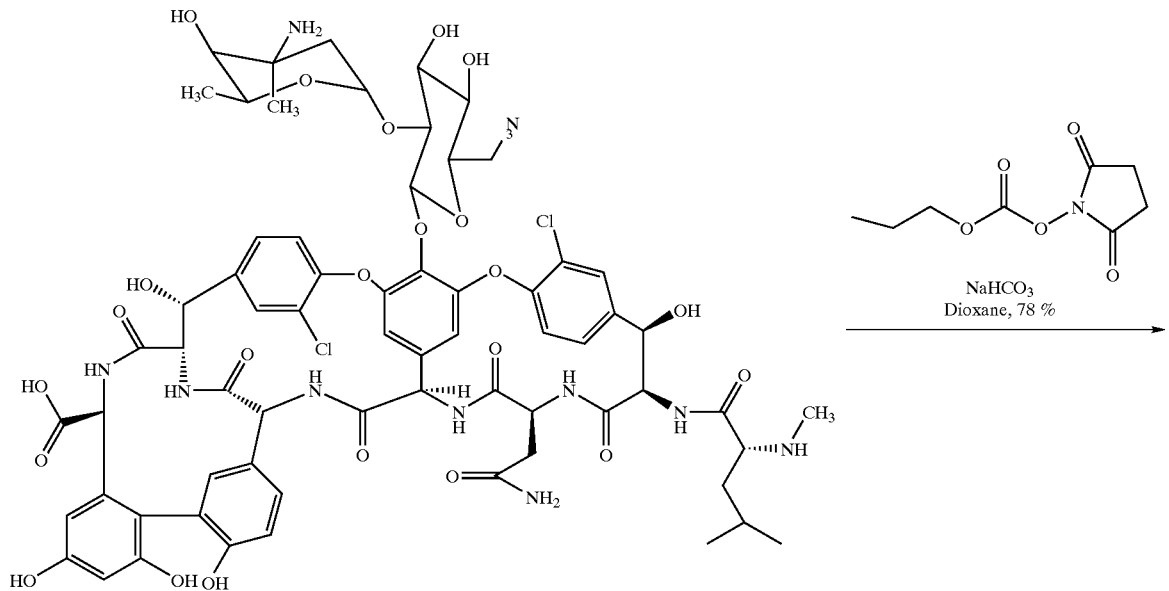

-continued
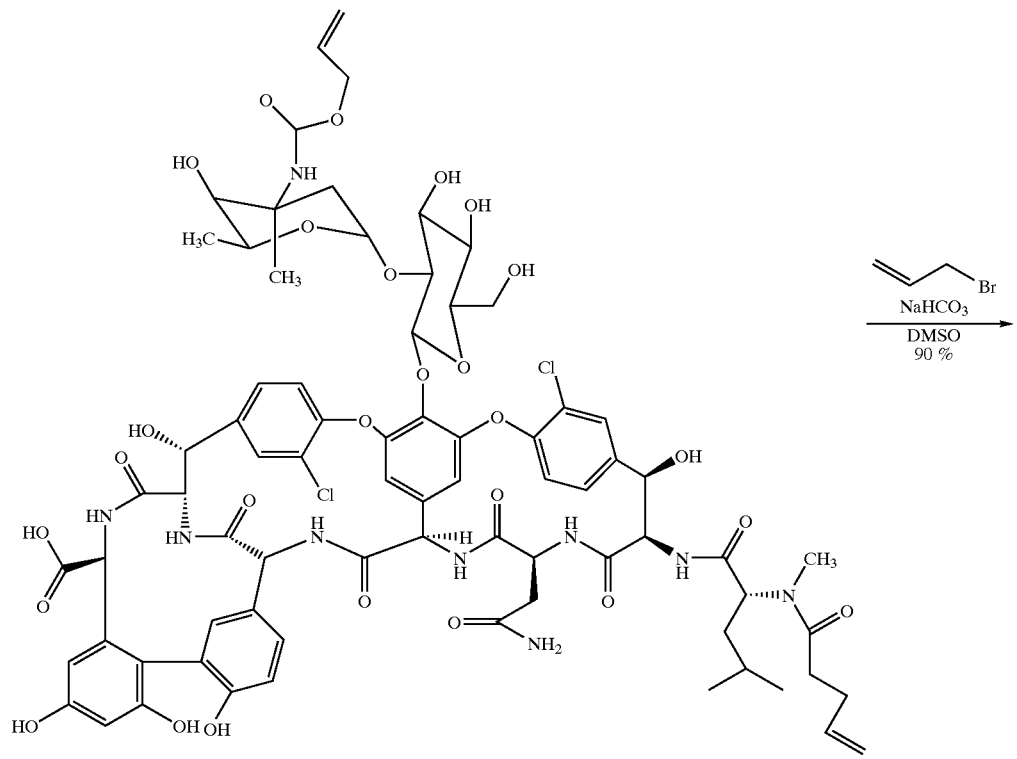
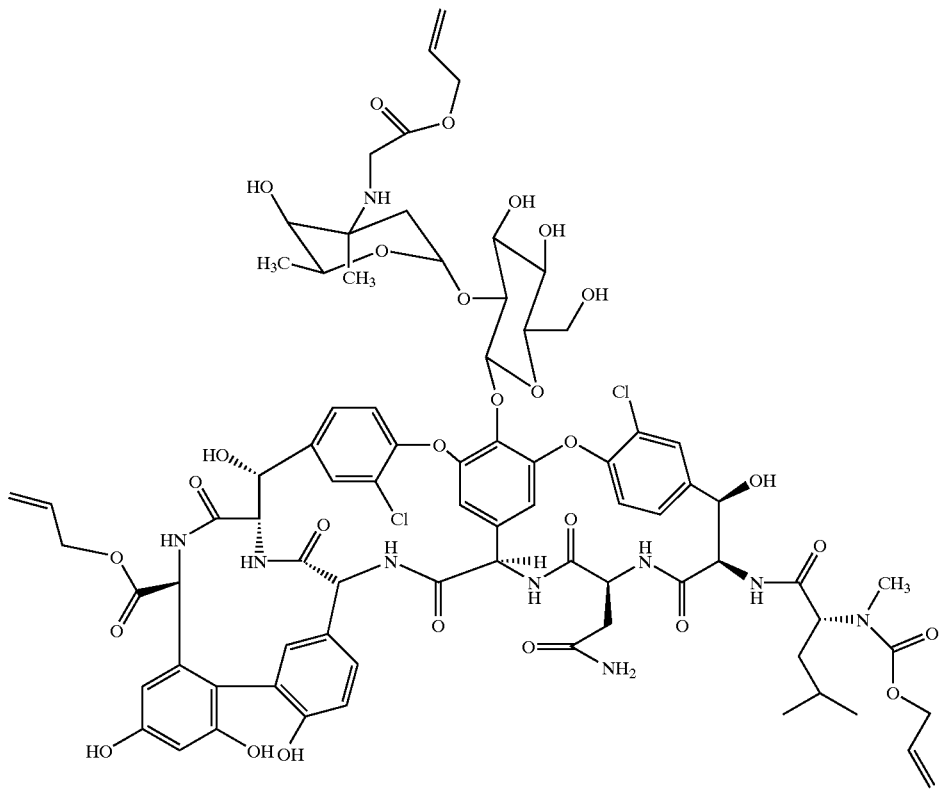

B. Functionalization of the C6 Position of the Glucose Residue with Mesitylene Sulfonyl
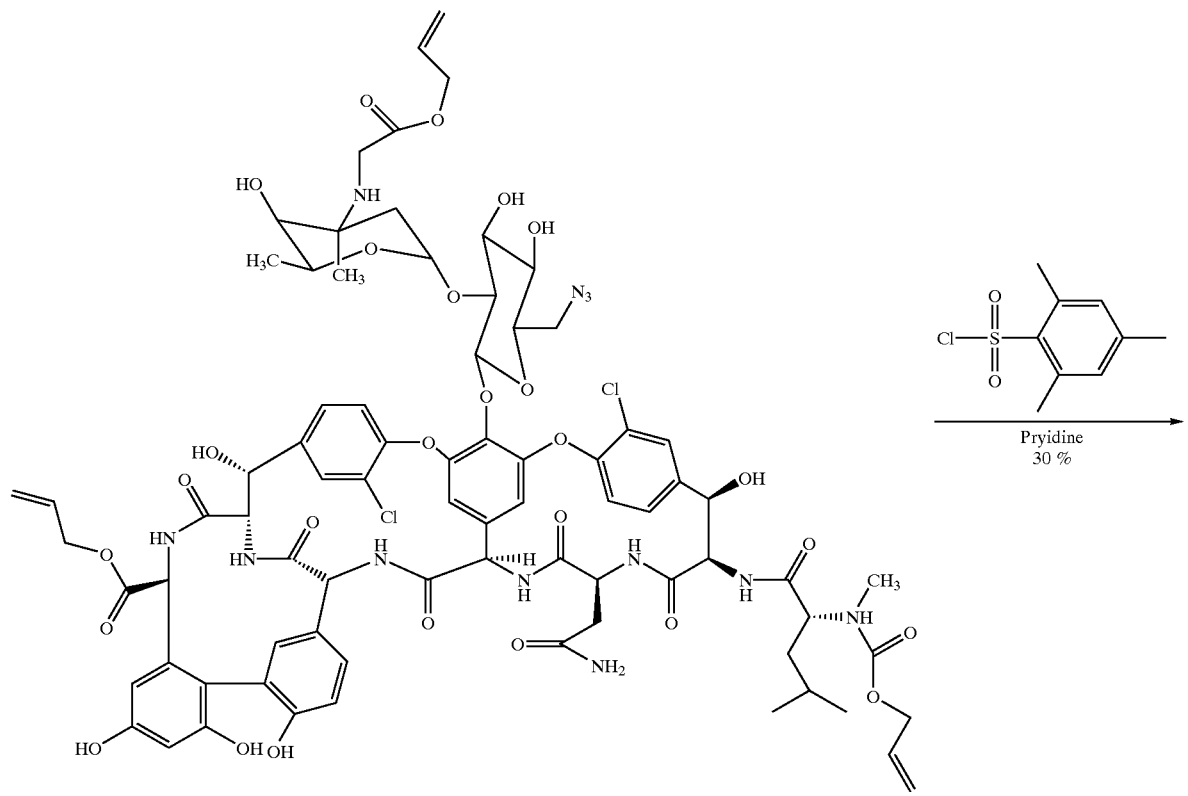
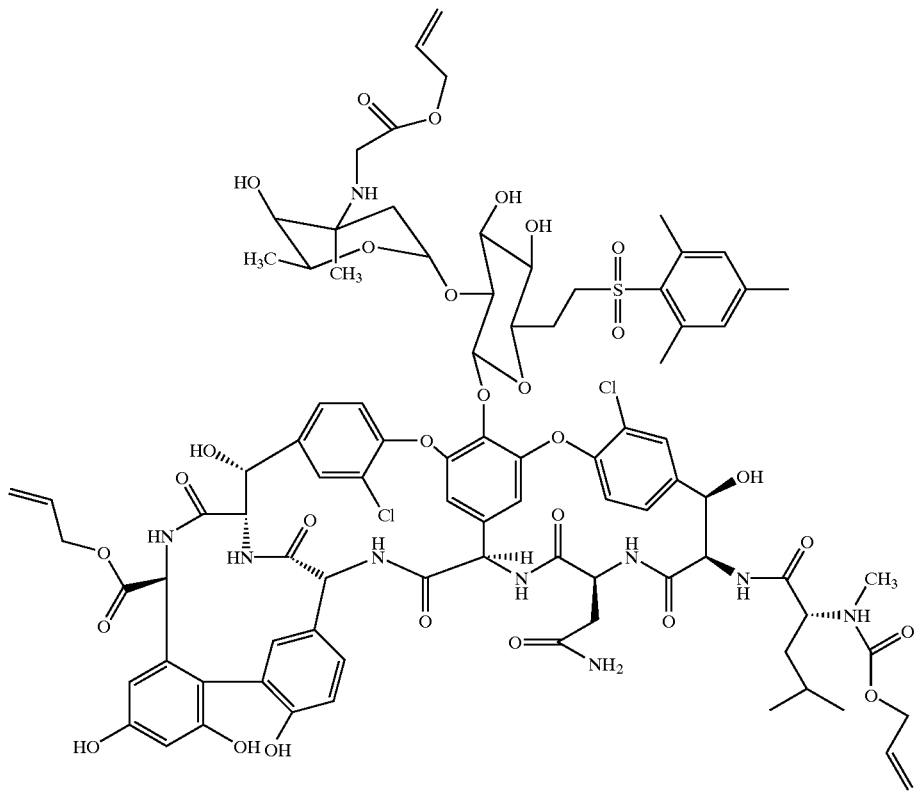

C. Deprotection of Vancosamine Nitrogen, N-methyl leucine Nitrogen and Terminal Carboxyl Group
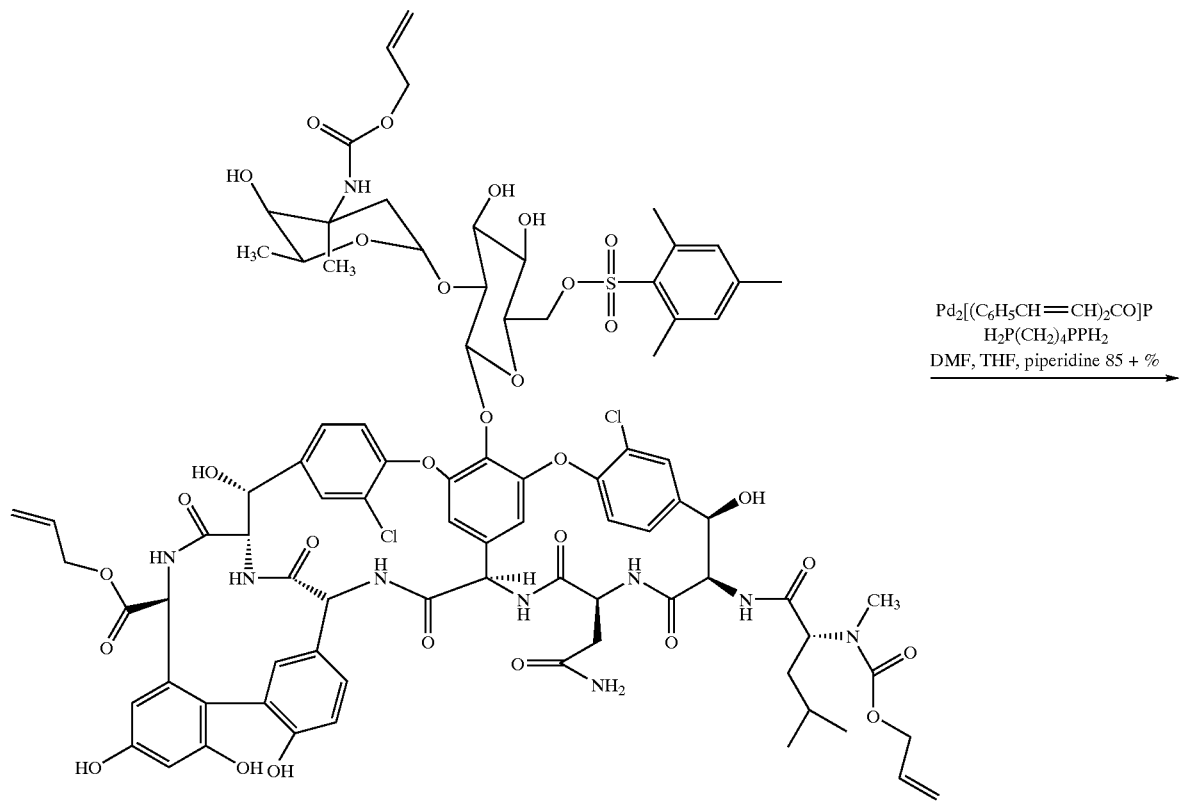
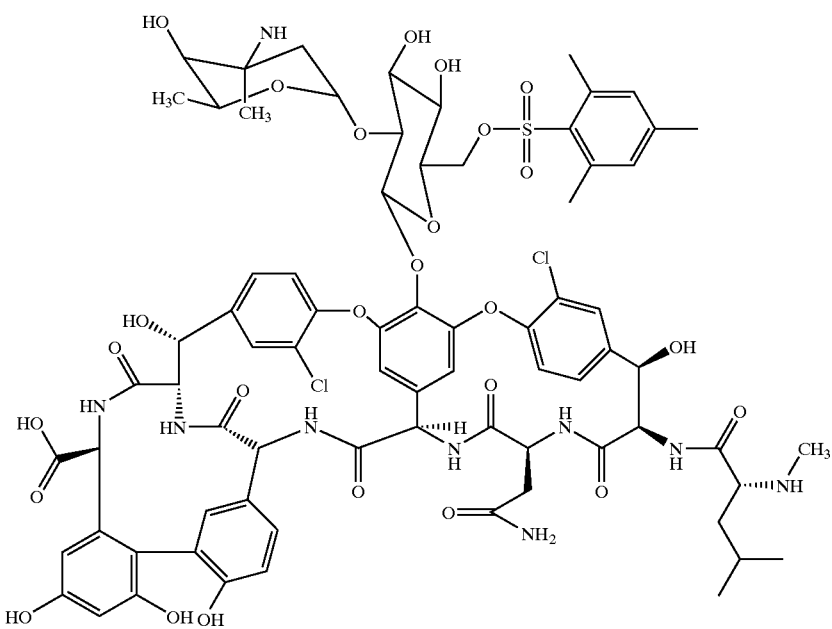

D. Reductive Alkylation of Vancosamine Nitrogen
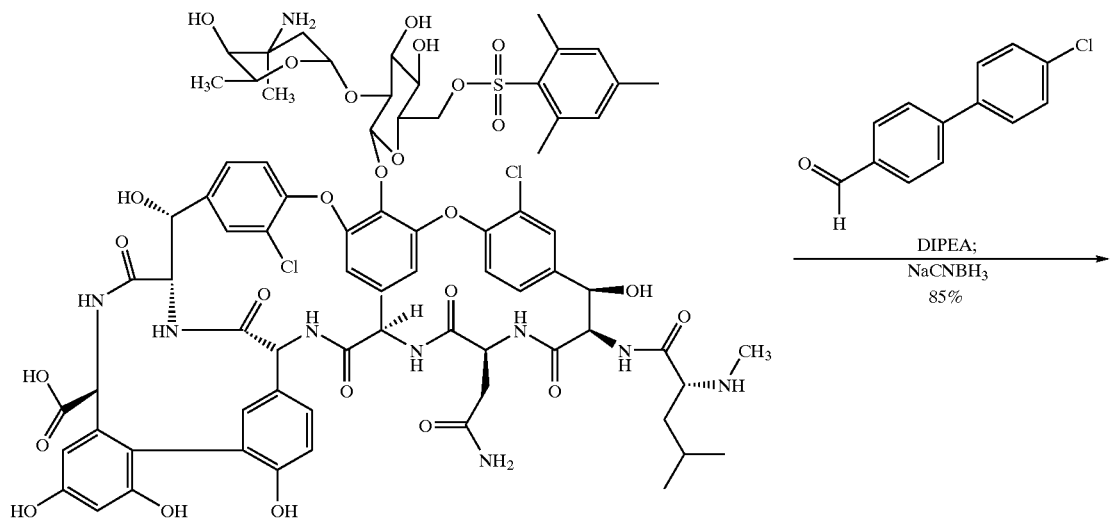
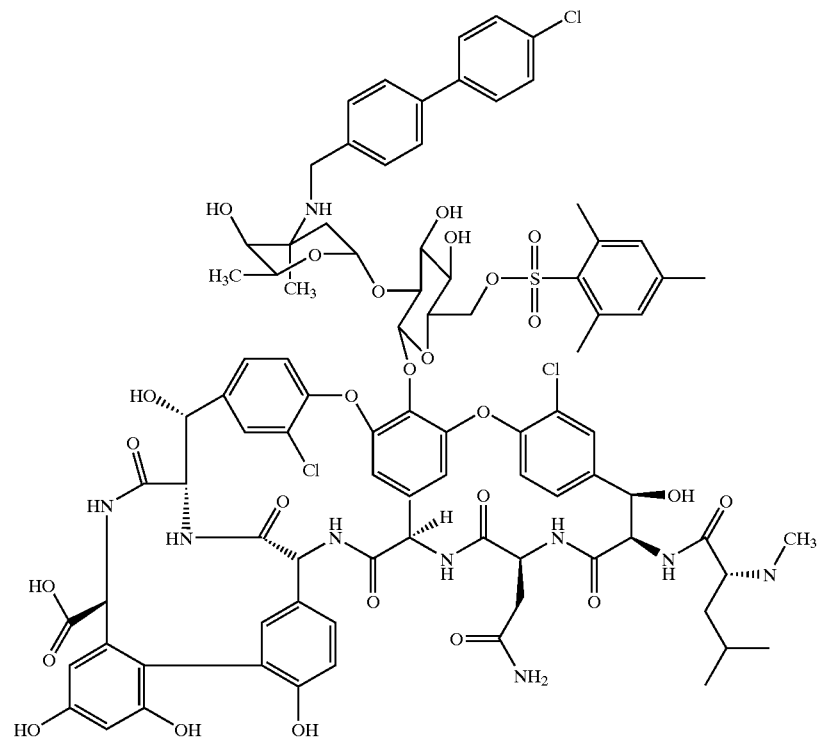

E. Displacement of Mesitylene Sulfonyl with Azido
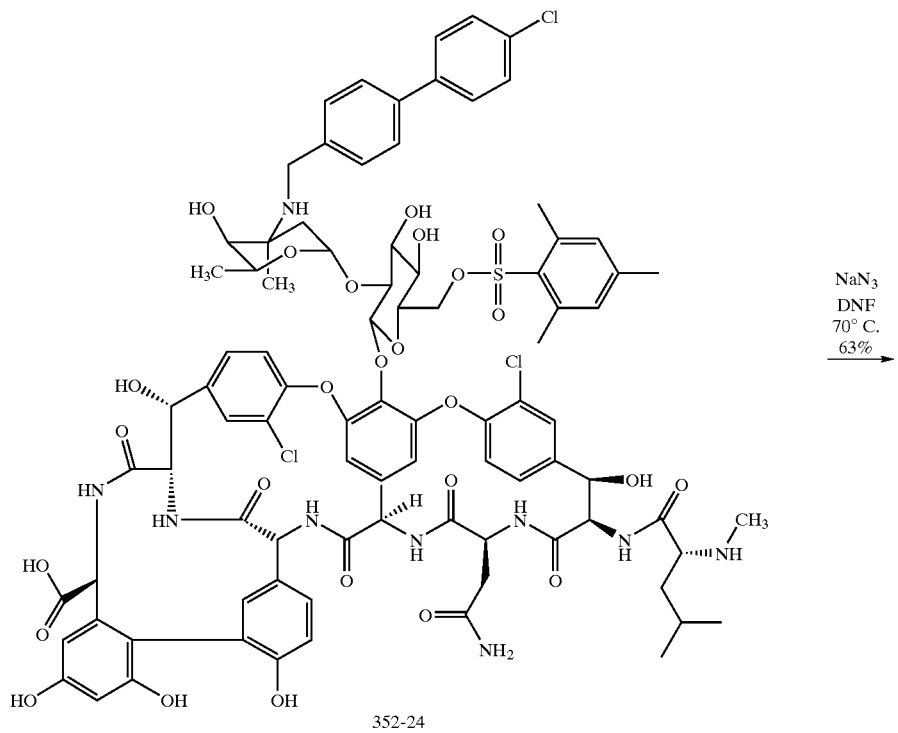
352-24
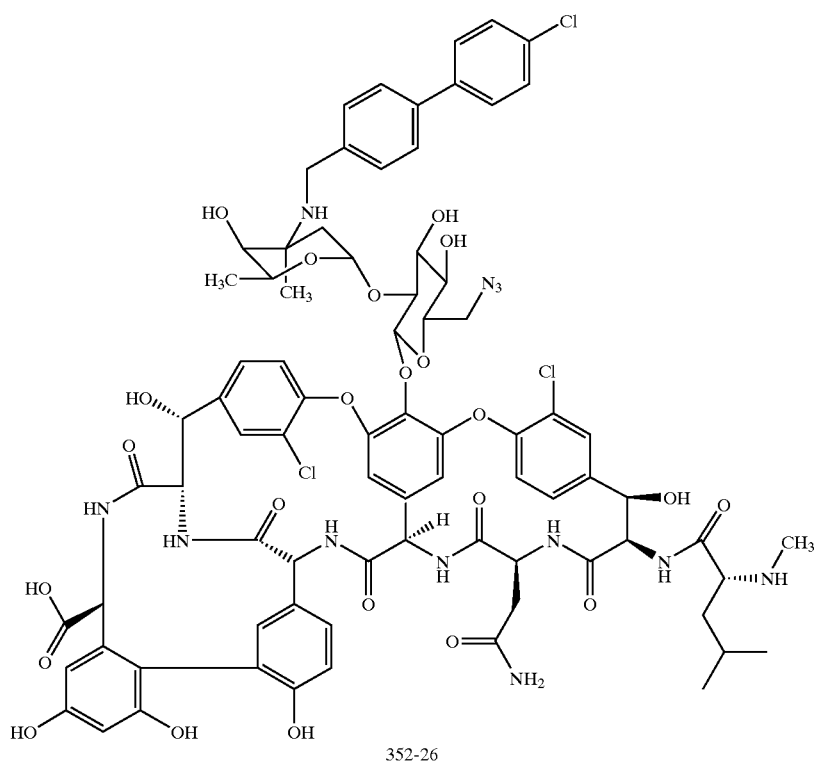
352-26

F. Functionalization of Terminal Carboxyl Group with Putrescine
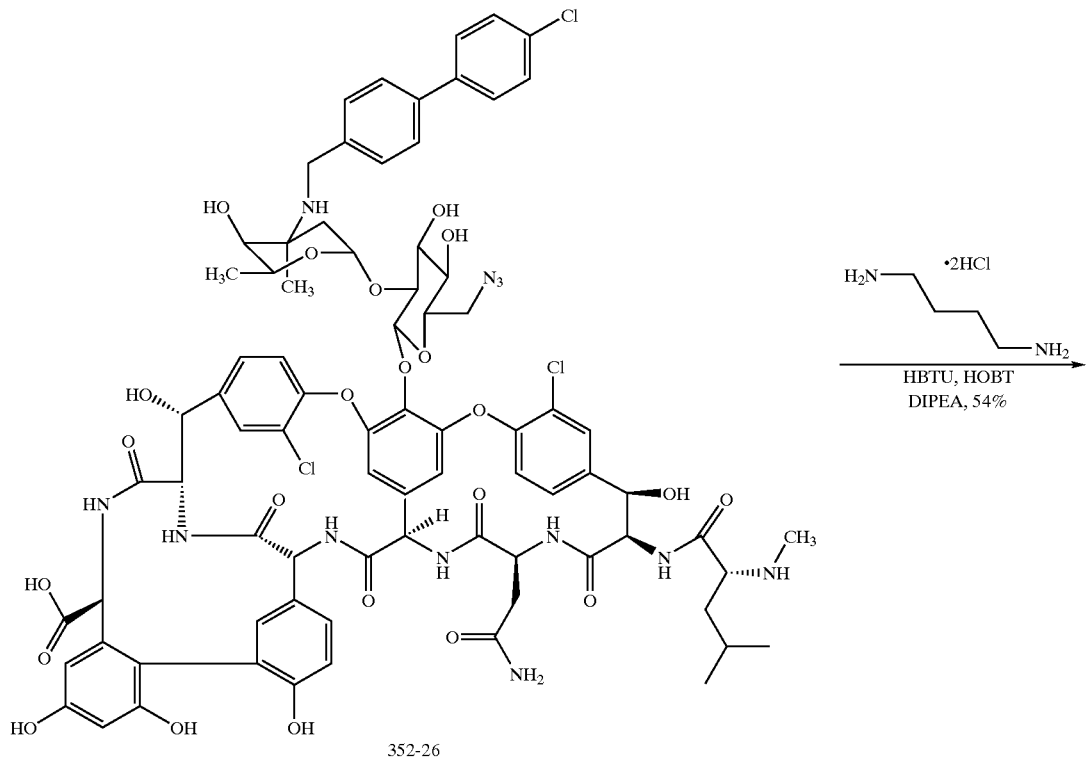
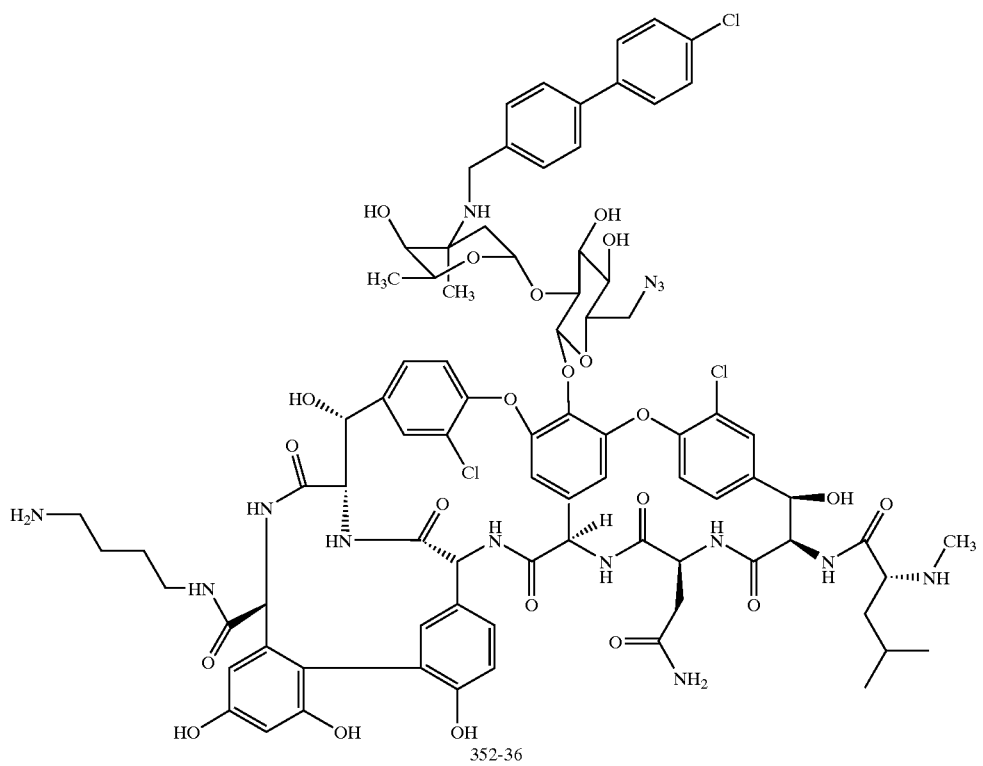

G. Reduction of Azido Group
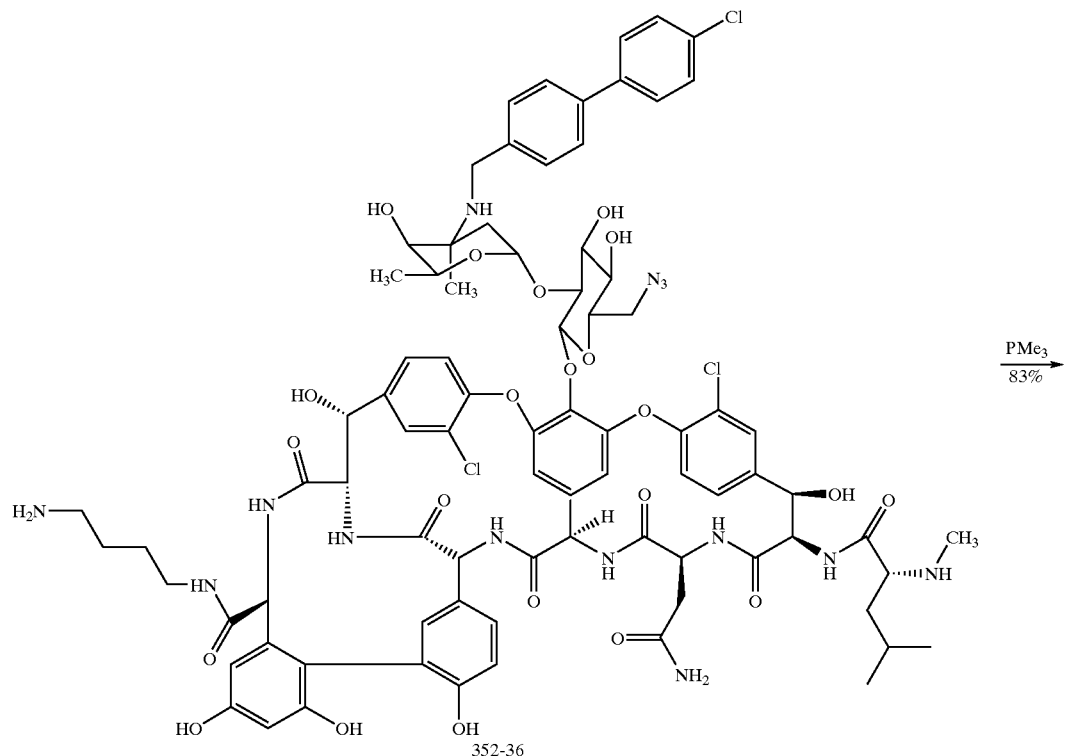
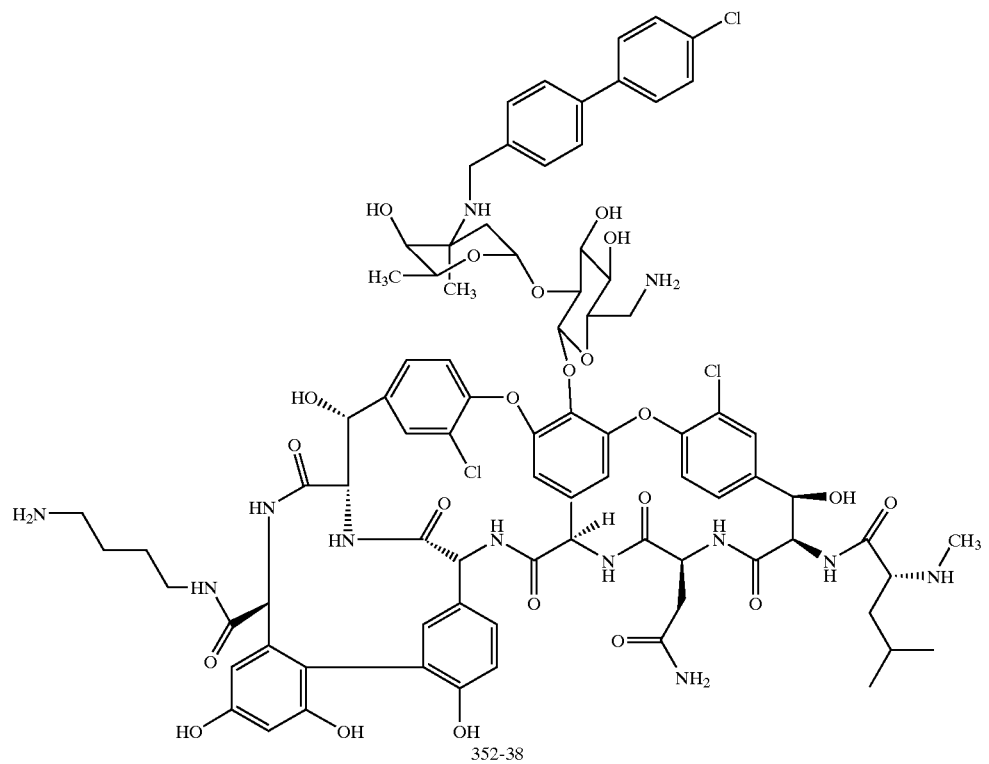

N-4-(4-chlorophenyl)benzyl vancosamino vancomycin putrescine amide

A. Reductive Alkylation of Vancosamine N

B. Functionalization of Terminal Carboxyl Group with Putrescine
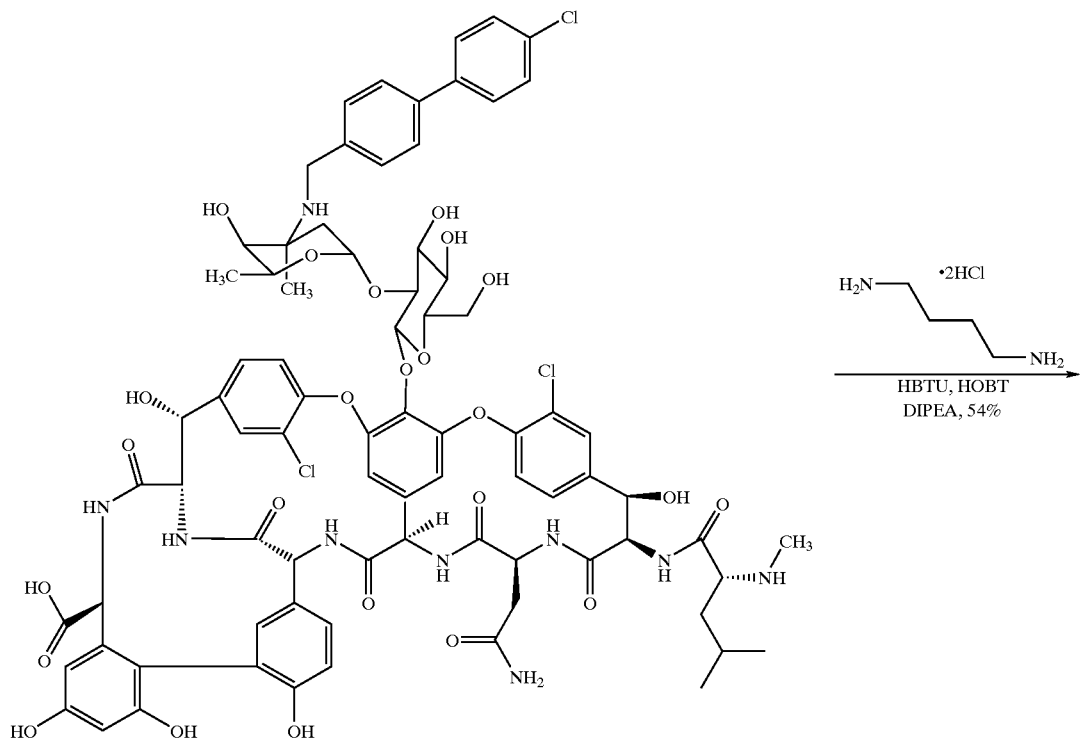
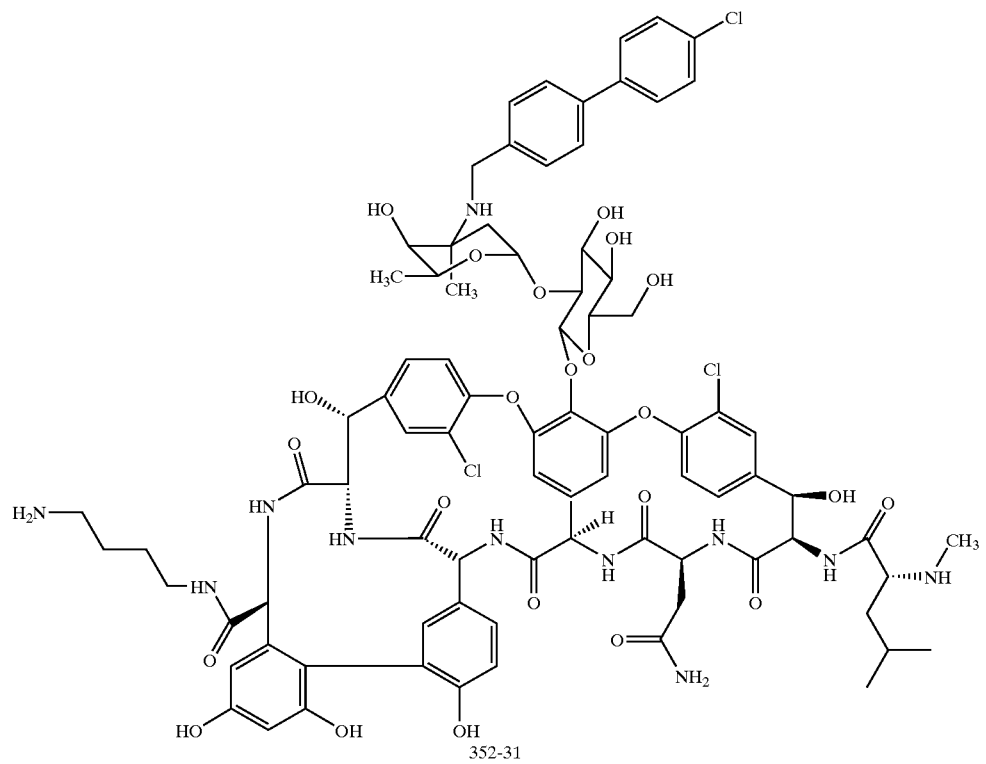

6-amino-N-4-(3,4-dichlorobenzyloxy)benzyl vancosamino vancomycin 2-aminoethylamide
A. Functionalization of Terminal Carboxyl Group with Ethylenediamine
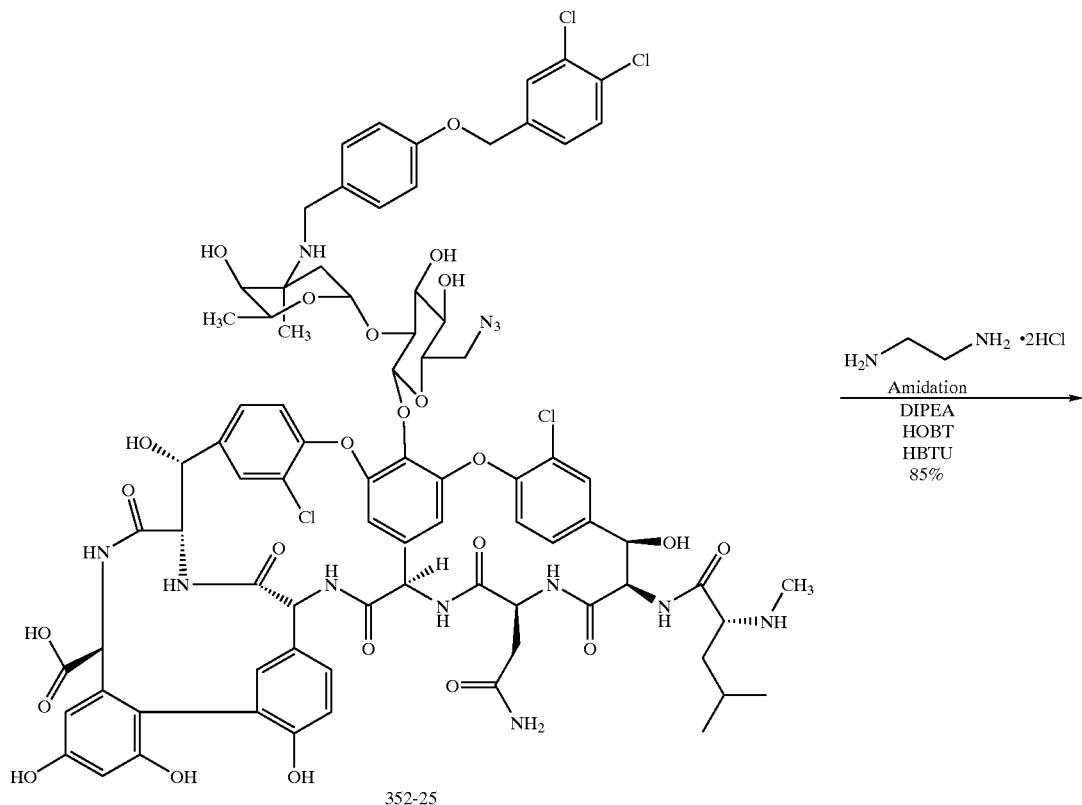
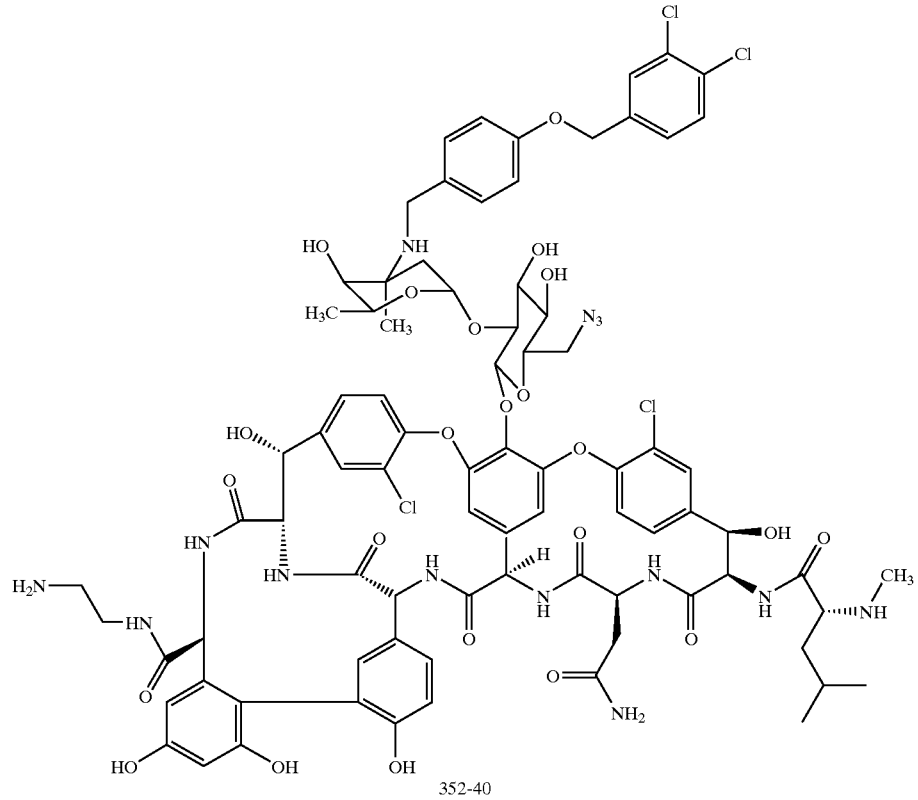

B. Reduction of Azido Group
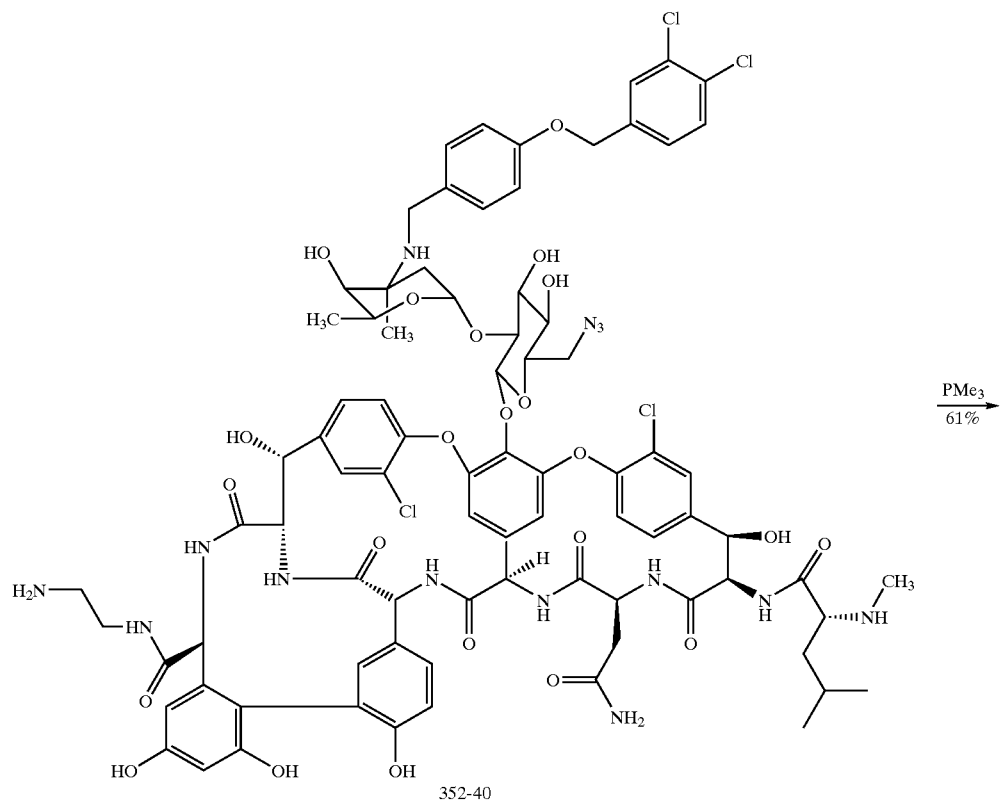
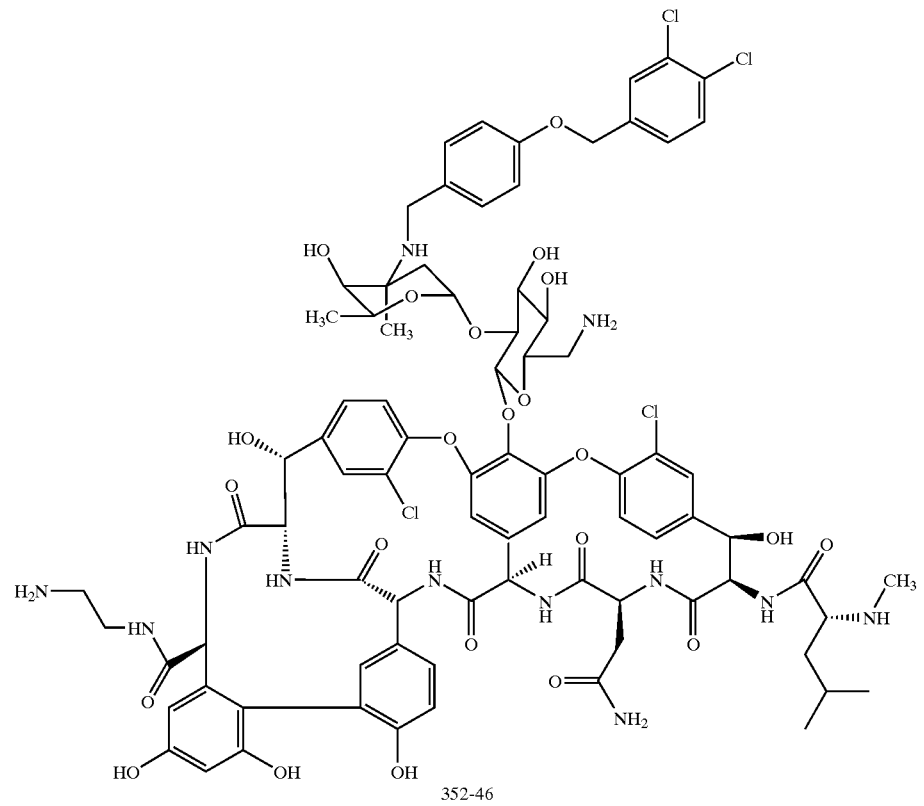

N-4-(3,4-dichlorobenzyloxy)benzyl vancosamino vancomycin putrescine amide
A. Reductive Alkylation of Vancosamine Nitrogen
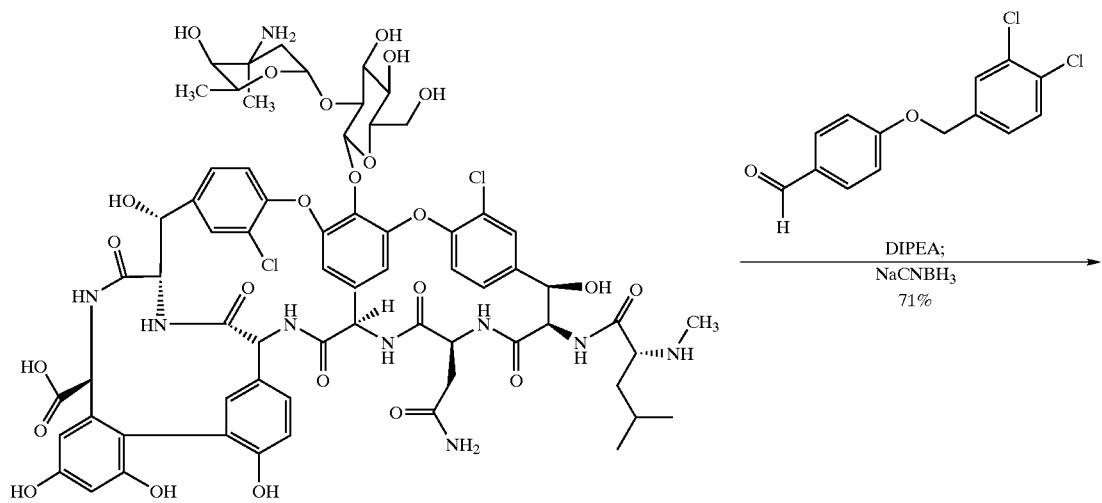
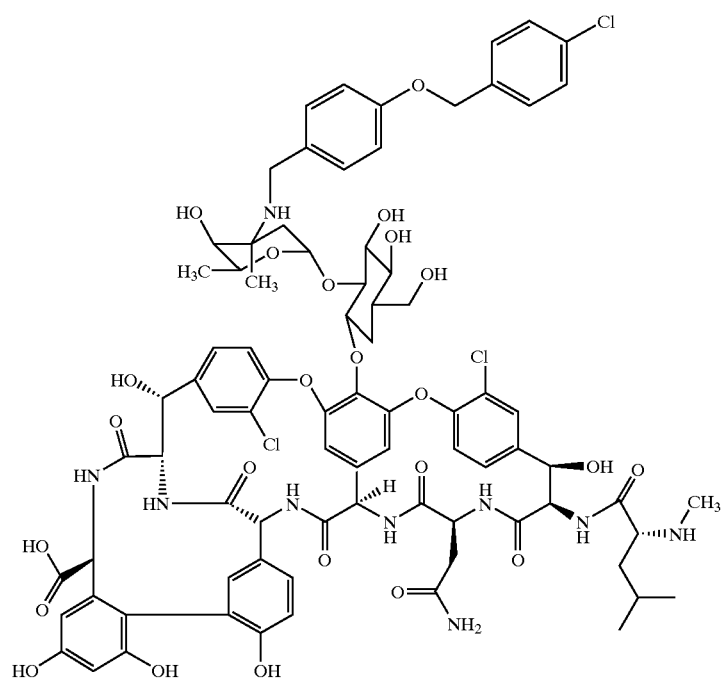

B. Functionalization of Terminal Carboxyl Group with Putrescine
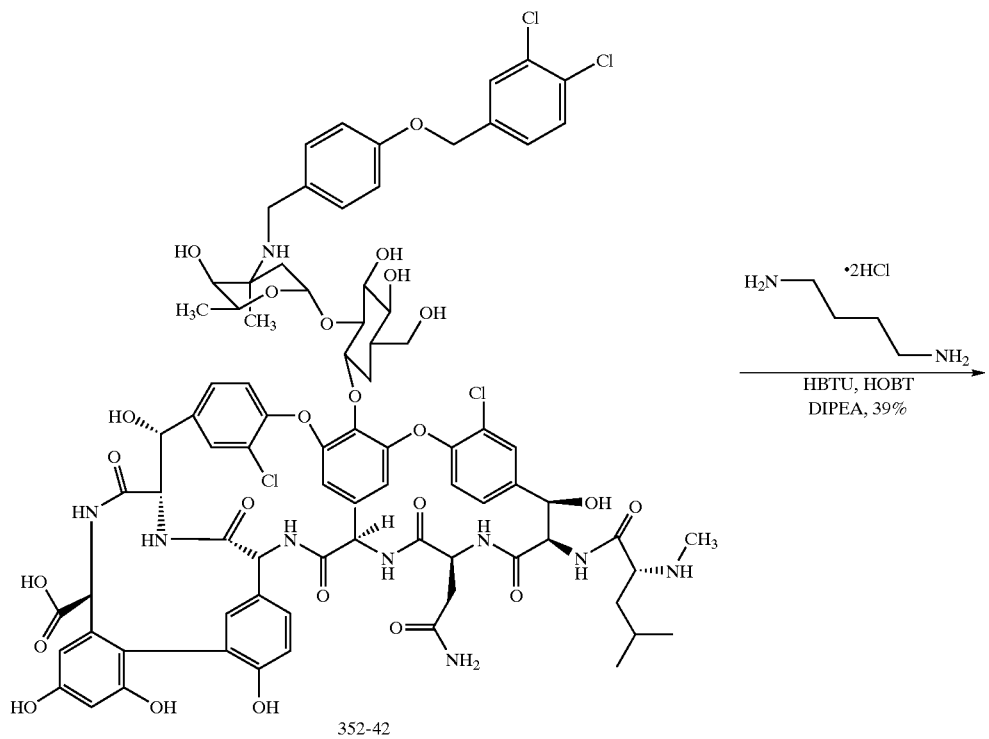
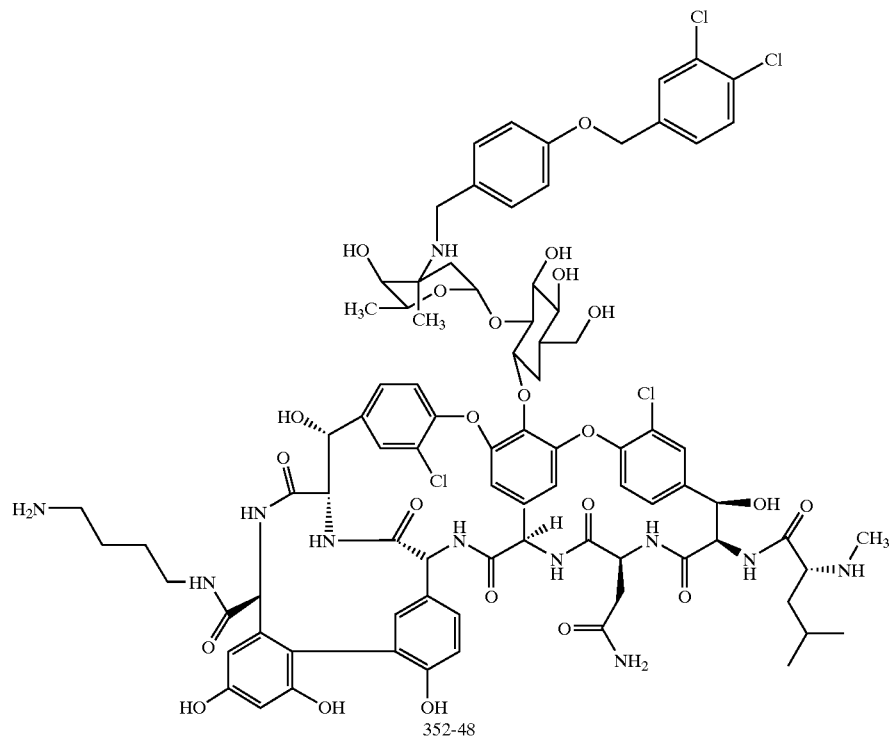

EXAMPLE 1

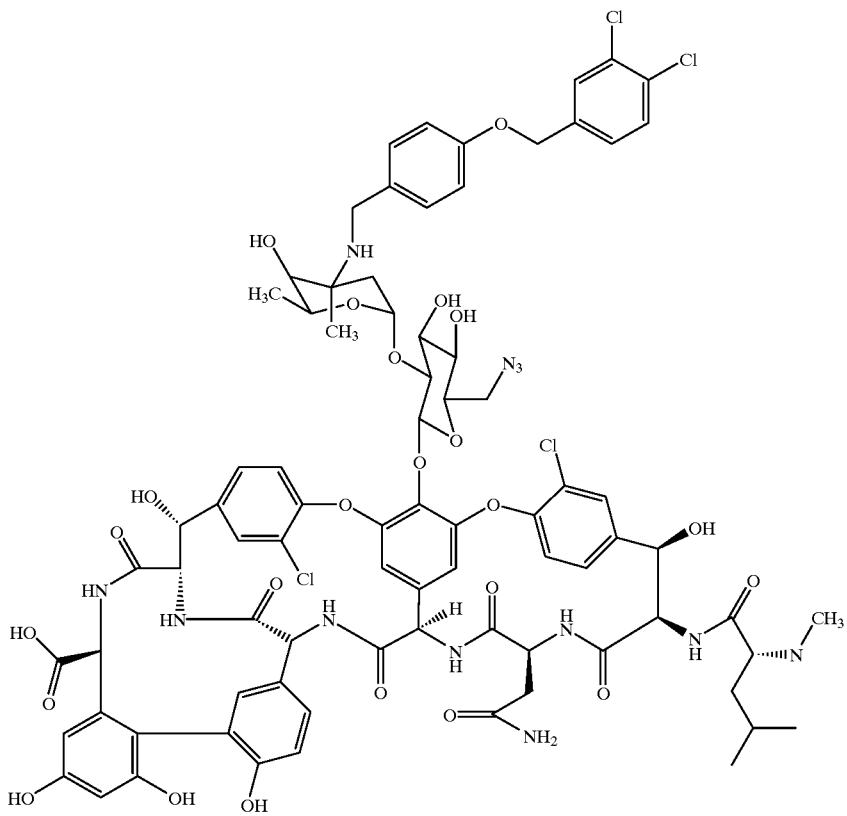

352-25

SI-352-25.

SI-352-22 (218 mg, 115 μmol) was dissolved in 5 mL of dry DMF. Sodium azide (1.15 mmol, 75 mg, 10 equiv.) was added and the mixture was heated at 70 C for 18 h. The reaction was monitored by LCMS. The reaction mixture was cooled to room temperature and poured into 100 mL of ether. The white precipitate was allowed to settle and the ether layer was decanted. The white precipitate was washed with 3×50 mL of ether and dried in vacuo. The light yellow solid was washed with water (2×5 mL). The resulting solid was suspended in water and lyophilized to yield 205 mg (102.5%) of a light yellow solid. The compound was further purified by HPLC to yield 89 mg (45%). An additional 41 mg has approximately 50% product.

LCMS shows M+1 (1741) and M/2+1 (870.5); M−1 (1737.8) and M/2−1 (868.8). Estimated Purity by LC-MS -95+%

EXAMPLE 2

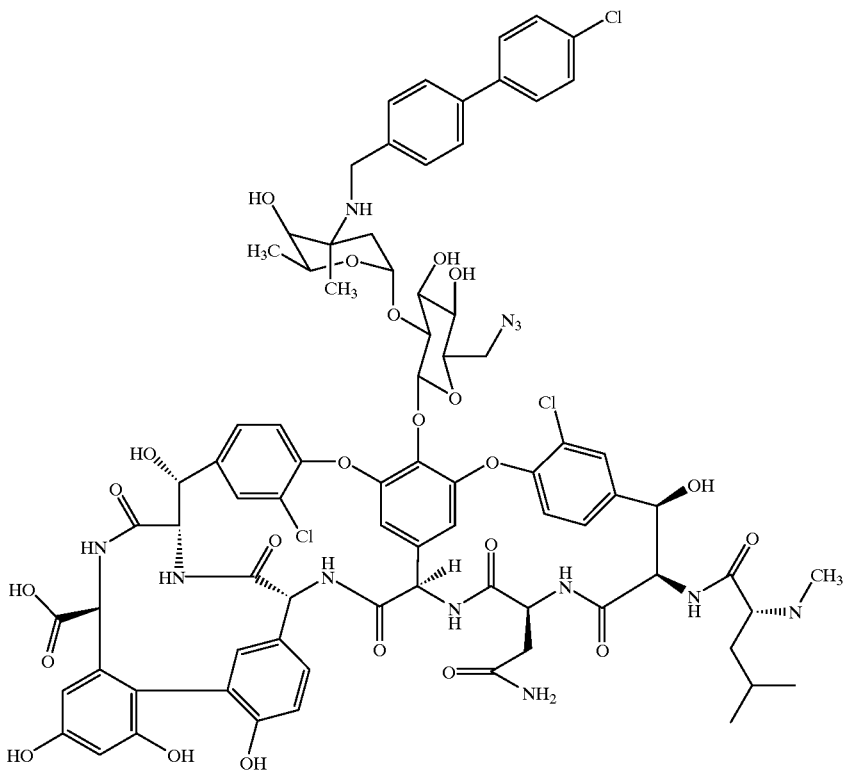

352-26

SI-352-26.

SI-352-24 (128 mg, 70 μmol) was dissolved in 4 mL of dry DMF. Sodium azide (0.7 mmol, 45 mg, 10 equiv.) was added and the mixture was heated at 70 C for 36 h. The reaction was monitored by LCMS. The reaction mixture was cooled to room temperature and poured into 100 mL of ether. The white precipitate was allowed to settle and the ether layer was decanted. The white precipitate was washed with 3×50 mL of ether and dried in vacuo. The light yellow solid was washed with water (2×5 mL). The resulting solid was suspended in water and lyophilized to yield 103 mg (88%) of a light yellow solid. The compound was further purified by HPLC to yield 57 mg (49%). An additional 46 mg. has approximately 25% product.

LCMS shows M+1 (1675.8) and M/2+1 (838.8); M−1 (1673) and M/2−1 (836.3). Estimated Purity by LC-MS-95+%

EXAMPLE 3

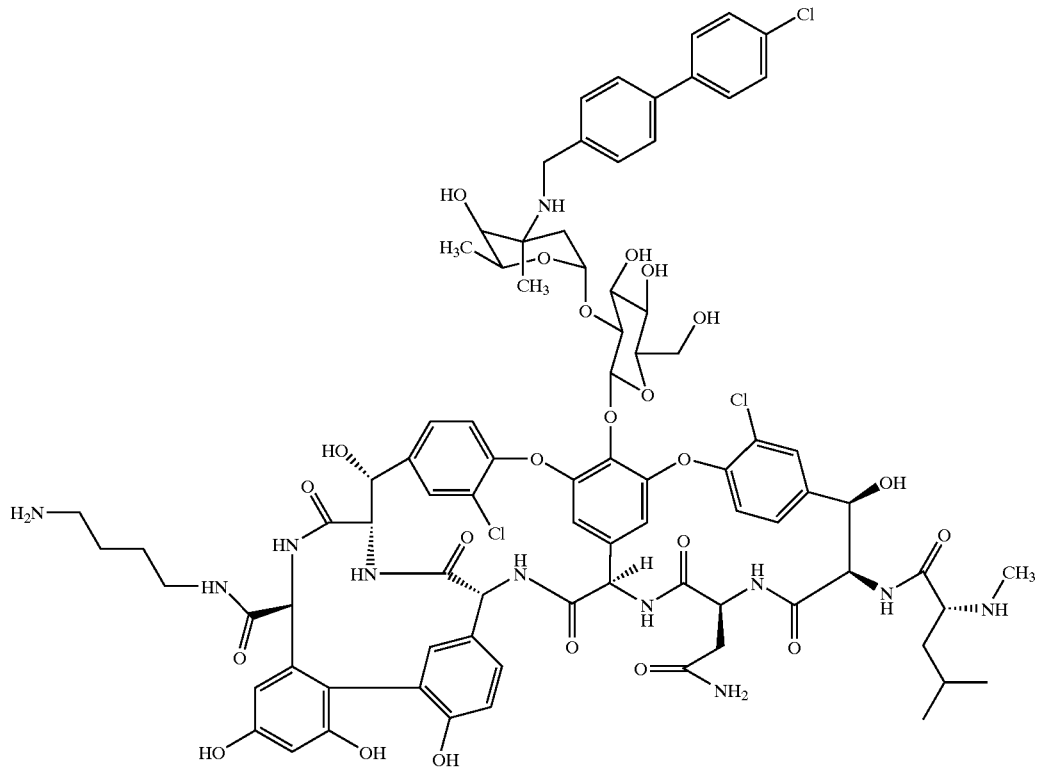

352-31

SI-352-31:

N-chlorobiphenylvancomycin (100 mg, 0.061 mmol) and putrescine (49 mg, 0.303 mmol, 5 equiv.) were azeotrophed with toluene (10 mL) three times. 1 mL of dry DMSO was added and the mixture was sonicated until a clear solution was obtained. 1 mL of dry DMF was added and the mixture was cooled to 0 C, and 0.40 mL (3 equiv.) of 0.45 M HBTU solution in DMF and 0.40 mL (3 equiv.) of 0.45 M HOBT solution in DMF were added, followed by diisopropylethylamine (105 μL 10 equiv.) The reaction was then allowed to warm to room temperature and stirred overnight. 20 mL of ether was added to the reaction mixture and the reaction was stirred until the turbid solution became clear. The ether layer was decanted and the sticky residue was dissolved in 2 mL of DMF. 20 mL of ether was added to the DMF solution and the ether layer was decanted. The white fluffy solid formed was washed with ether and lyophilized to yield 117 mg of an off-white solid. The product was dissolved in 10 mL of 40% aq. acetonitrile and purified by preparative HPLC and lyophilized to afford 50 mg (48%) of pure product.

LCMS shows M (1720.5) and M/2+1 (861); M−1 (1719.3) and M/2−1 (859). Estimated Purity by LC-MS—95+%

EXAMPLE 4

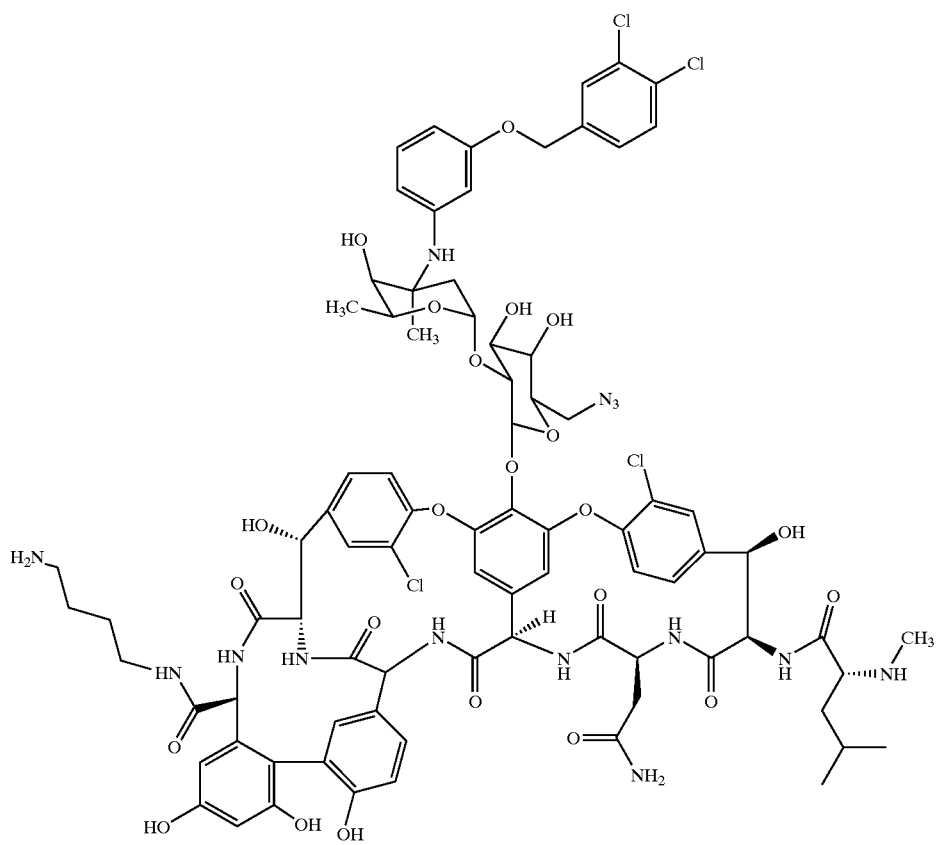

352-33

SI-352-33:

SI-352-25-4P (38 mg, 0.022 mmol) and putrescine (18 mg, 0.11 mmol, 5 equiv.) were azeotrophed with toluene (10 mL) three times. 1 mL of dry DMSO was added and 1 mL of dry DMF were added and the mixture was cooled to 0 C, and HBTU (34 mg, 0.066 mmol, 3 equiv.) and HOBT (12 mg, 0.066 mmol, 3 equiv.) were added, followed by diisopropylethylamine (40 µL, 10 equiv.) The reaction was then allowed to warm to room temperature. After 2 h, LC-MS showed near loss of SI-352-25-4P and appearance of a product with M/2+1 at 906. The reaction mixture was poured into ether and stirred until the turbid mixture became clear. The clear supernatant ether layer was decanted and 2 mL of DMF was added. To the DMF solution was added 50 mL of ether. The product precipitated as a white fluffy solid. The ether layer was decanted and the precipitate was washed with ether to remove traces of DMF. The white precipitate was dissolved in 3 mL of water and lyophilized to yield 58 mg of an off-white solid. The compound was purified by HPLC on a YMC-CYANO column to yield 20 mg (51%) of a white fluffy solid.

LCMS shows M+1 (1810) and M/2+1 (905.5); M−1 (1807) and M/2−1 (903.5). Estimated Purity by LC-MS-95+%.

EXAMPLE 5

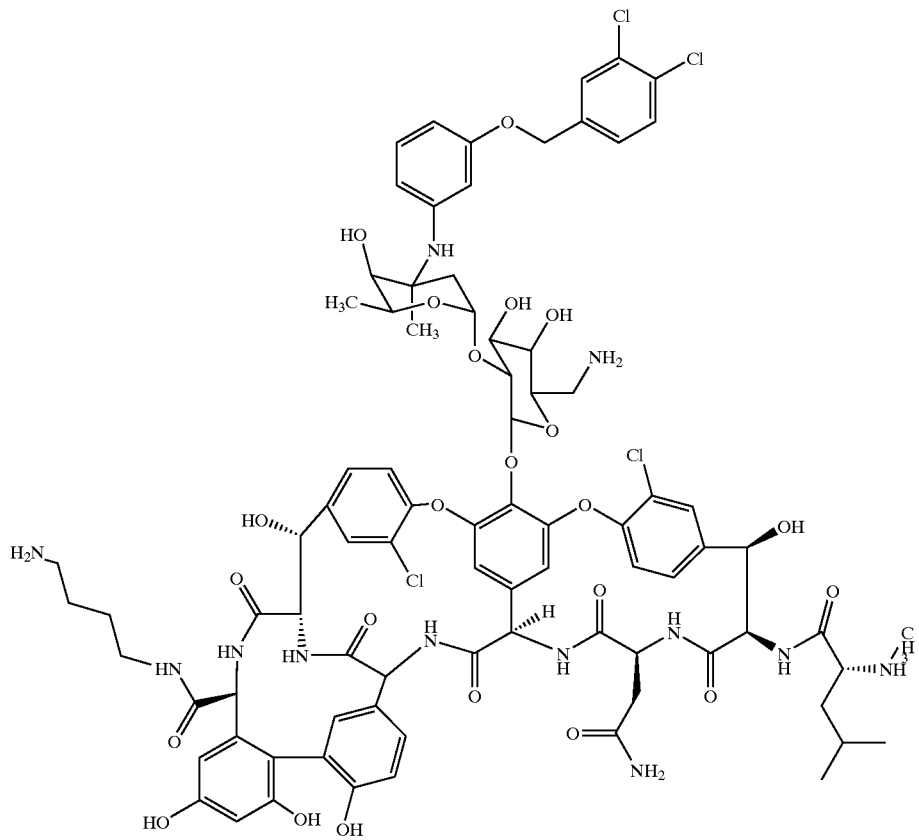

352-35

SI-352-35:

SI-352-33 (18 mg, 10 μmol) was dissolved in 0.1 mL of DMF and then 0.1 mL of EtOH, 0.1 mL of water and 0.4 mL of THF were added. Finally PMe$_3$ (80 μL, 80 μmol) was added and the reaction was stirred at room temperature overnight. The reaction was concentrated to dryness under reduced pressure and lyophilized to yield 17 mg (96%) of a white solid. The crude material was purified on the YMC-CYANO column to yield 14 mg (79%) of pure amine.

LCMS shows M(1782.3) and M/2+1 (893.5); M (1783) and M/2−1 (890.5). Estimated Purity by LC-MS-95+%

EXAMPLE 6

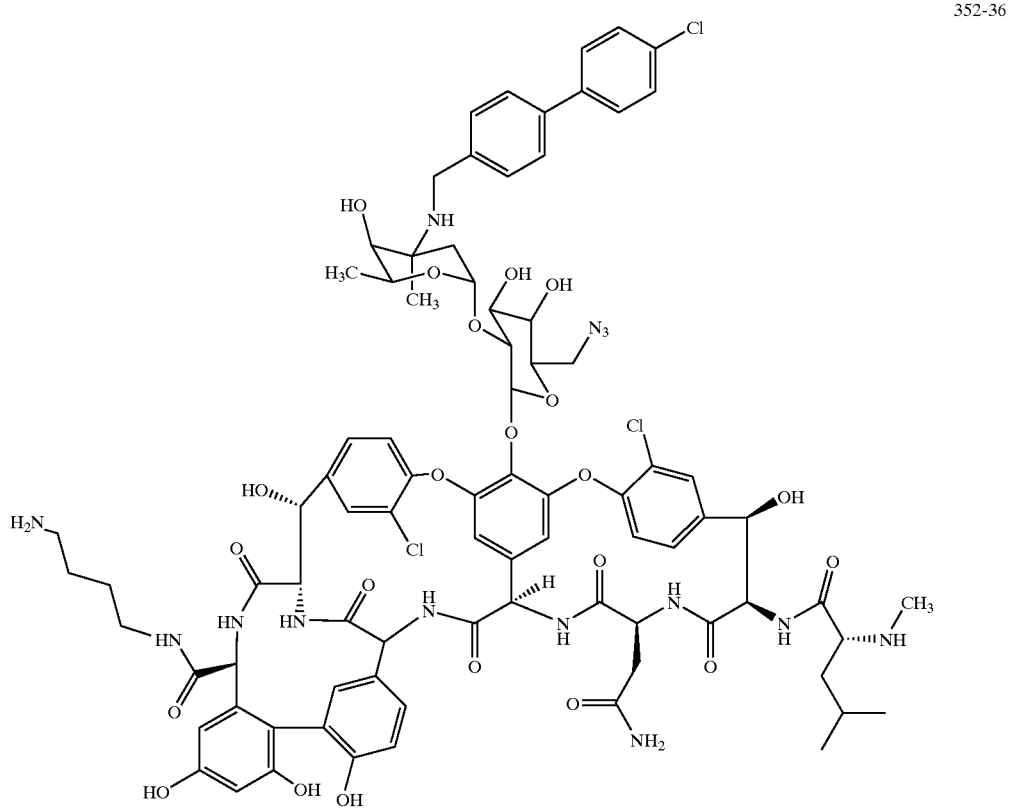

352-36

SI-352-36:

SI-352-26-PP (23 mg, 0.013 mmol) and putrescine (11 mg, 0.066 mmol, 5 equiv.) were azeotrophed with toluene (10 mL) three times. 0.5 mL of dry DMSO and 0.5 mL of dry DMF were added and the mixture was cooled to 0 C, and HBTU (15 mg, 0.039 mmol, 3 equiv.) and HOBT (5 mg, 0.039 mmol, 3 equiv.) were added, followed by diisopropylethylamine (25 µL, 10 equiv.) The reaction was then allowed to warm to room temperature. After 2 h, LC-MS showed near loss of SI-352-26-PP and appearance of a product with M/2+1 at 873. The reaction mixture was poured into ether and stirred until the turbid mixture became clear. The clear supernatant ether layer was decanted and 2 mL of DMF was added. To the DMF solution was added 50 mL of ether. The product precipitated as a white fluffy solid. The ether layer was decanted and the precipitate was washed with ether to remove traces of DMF. The white precipitate was dissolved in 3 mL of water and lyophilized to yield 58 mg of an off-white solid.

The product was purified by preparative HPLC (YMC-CYANO column) and lyophilized to afford 13 mg (54%) of a white solid.

LCMS shows M(1745.3) and M/2+1 (873.5); M (1744.8) and M/2-1 (871.3)

Estimated Purity by LC-MS-95+%

EXAMPLE 7

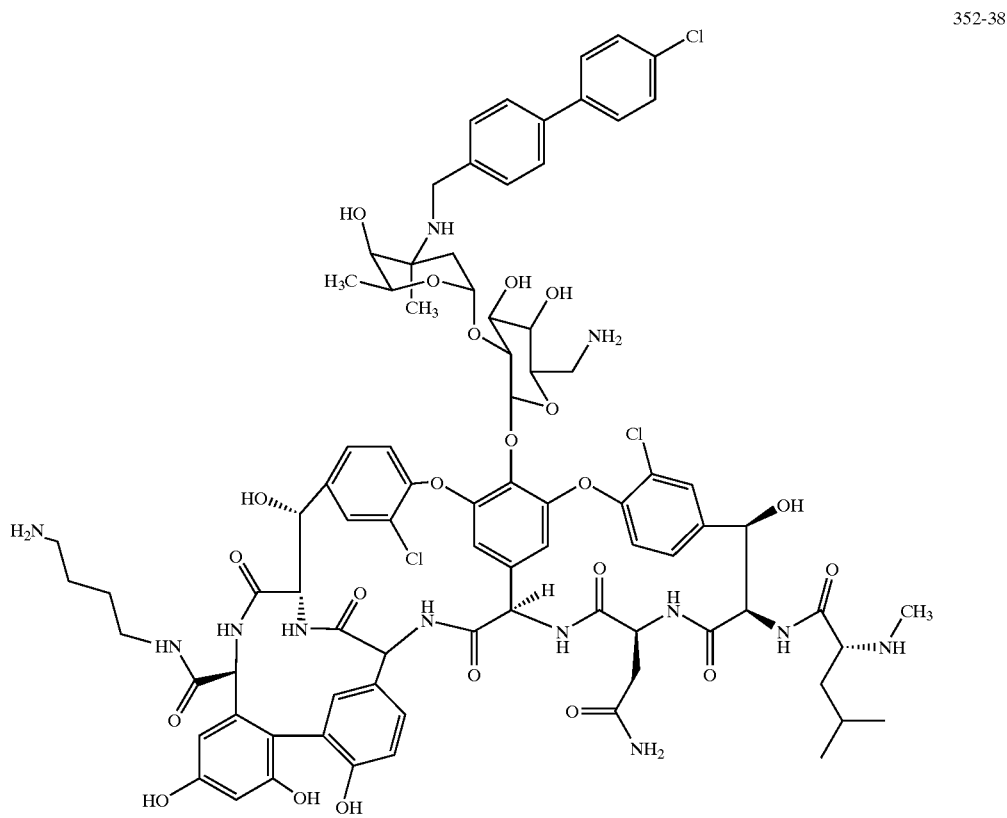

352-38

SI-352-38.

SI-352-36 (11 mg, 6.3 μmol) was dissolved in a mixture of 0.1 mL of EtOH, 0.2 mL of water and 0.4 mL of THF. Finally, PMe₃ (50 μL, 50 μmol) was added and the reaction was stirred at room temperature overnight. The reaction was concentrated to dryness under reduced pressure and lyophilized to yield 14 mg (133%) of a white solid. The crude material was purified on the YMC-CYANO column to yield 9 mg (83%) of pure amine.

LCMS shows M+2 (1721.3) and M/2+1 (861); M-2 (1716.8) and M/2-1 (858.5).

Estimated Purity by LC-MS -95+%.

EXAMPLE 8

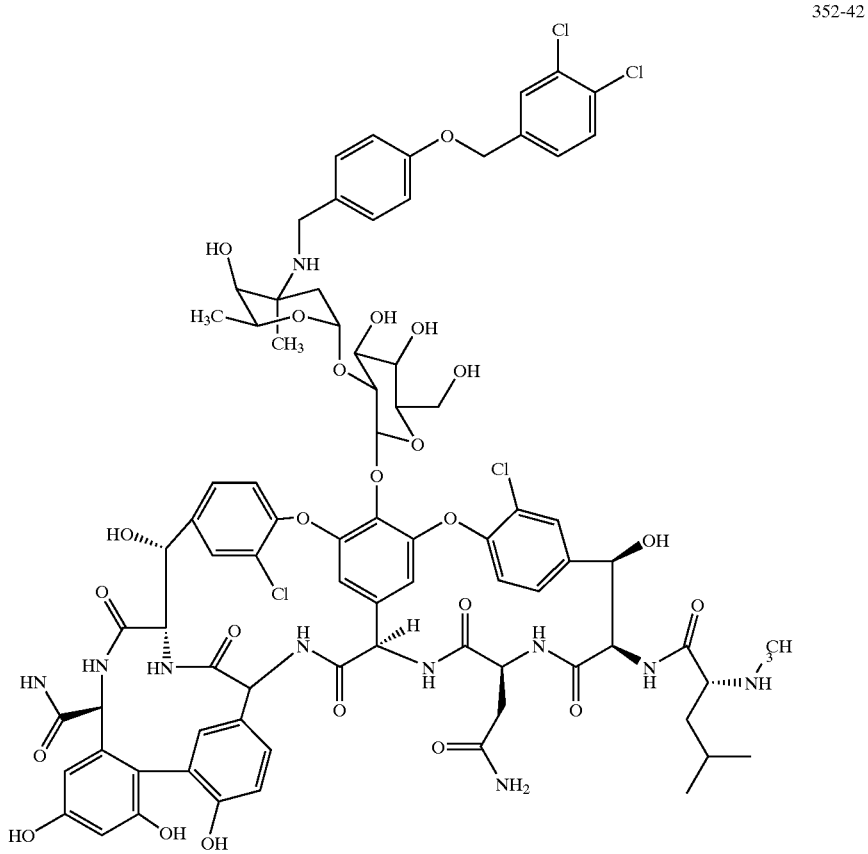

352-42

SI-352-42.

Vancomycin HCl (1 g, 0.69 mmol), DIPEA (270 μL) and 3',4'-dichlorobenzyloxybenzaldehyde (312 mg, 1.035 mmol) were dissolved in 20 mL of anhydrous DMF and heated to 70 C for 45 minutes. NaCNBH$_3$ solution (0.5 M solution in DMF; 7 mL, 3.45 mmol) was added and the reaction mixture was stirred at 70 C for 5 h. The reaction mixture was poured into 150 mL of ether, washed with 3×100 mL of ether; dried and then washed with 50 mL of water. The solid was re-suspended in water and lyophilized to afford a fluffy white solid which was re-subjected to the reaction conditions since the reaction was only 50% complete as per the LC-MS results. The white solid was dissolved in 20 mL of anhydrous DMF, and DIPEA (270 μL) and 3',4'-dichlorobenzyloxybenzaldehyde (208 mg, 0.69 mmol) were added. The mixture was heated at 70 C for 45 minutes. NaCNBH$_3$ solution (0.5 M solution in DMF; 7 mL, 3.45 mmol) was added and the reaction mixture was stirred at 70 C for 5 h. The reaction mixture was poured into 150 mL of ether, washed with 3×100 mL of ether; dried and then washed with 150 mL of water. The solid was re-suspended in water and lyophilized to afford a white solid. The solid was dissolved in 50 mL of 2:1 mixture of acetonitrile:water. The compound was purified by HPLC to yield 326 mg (28%; Corrected yield: 71%) of pure mono-alkylated product along with 388 mg (29%) of a 15:85 mixture of mono- and di-alkylated products and 507 mg (46%) of a 1:1 mixture of mono-alkylated product:starting material.

LCMS shows M+1 (1715) and M/2+1 (858); M−1 (1713.8) and M/2−1 (855.8) for product.

Estimated Purity by LC-MS95+%

EXAMPLE 9

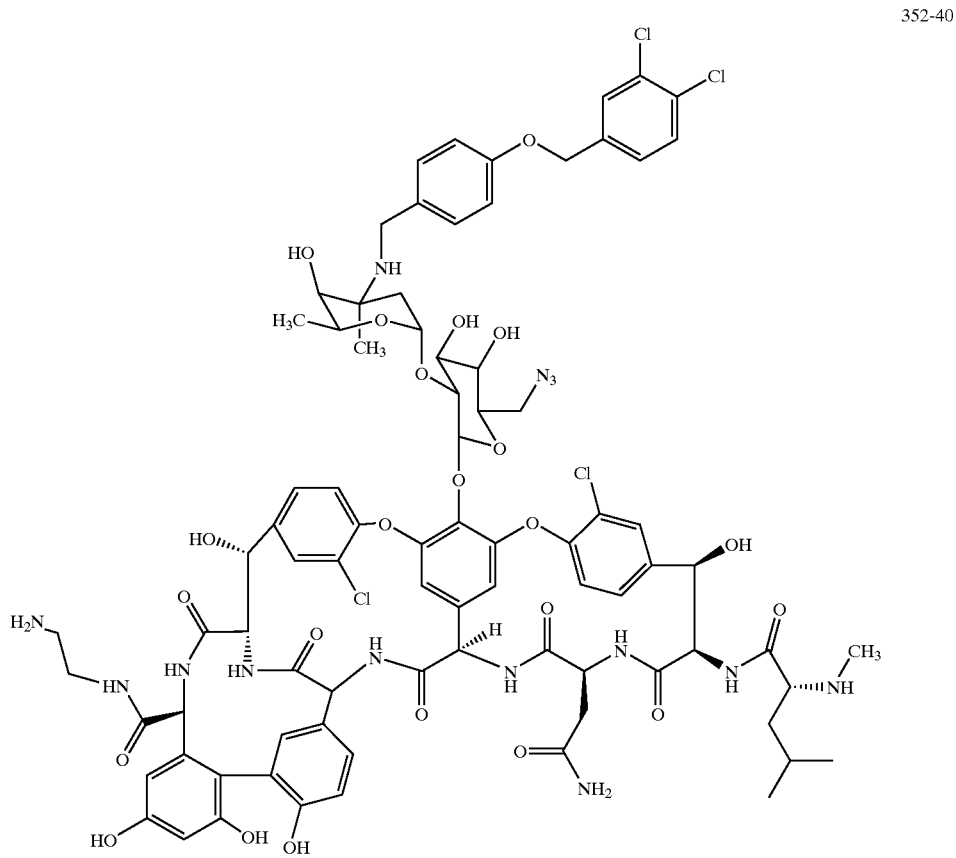

352-40

SI-352-40:

SI-352-25-5P (15 mg, 8.6 μmol) and ethylene diamine dihydrochloride (6 mg, 43 μmol, 5 equiv.) were dissolved in 0.5 mL of dry DMSO and 0.5 mL of dry DMF. The mixture was cooled to 0 C, and HBTU (10 mg, 0.026 mmol, 3 equiv.) and HOBT (4 mg, 0.026 mmol, 3 equiv.) were added, followed by diisopropylethylamine (16 μL, 10 equiv.). The reaction was then allowed to warm to room temperature. After 18 h, LC-MS showed near loss of SI-352-25-5P and appearance of a product with M/2−1 at 889.5. The reaction mixture was poured into ether and stirred until the turbid mixture became clear. The clear supernatant ether layer was decanted and 2 mL of DMF was added. To the DMF solution was added 50 mL of ether. The product precipitated as a white fluffy solid. The ether layer was decanted and the precipitate was washed with ether to remove traces of DMF. The white precipitate was dissolved in 3 mL and lyophilized to yield 23 mg of an off-white solid. The compound was purified by HPLC on a YMC-CYANO column to yield 13 mg (85%) of a white solid.

LCMS shows M+1 (1781.8) and M/2+1 (891); M−1 (1780.8) and M/2-1 (889.5). Estimated Purity by LC-MS-85+%.

EXAMPLE 10

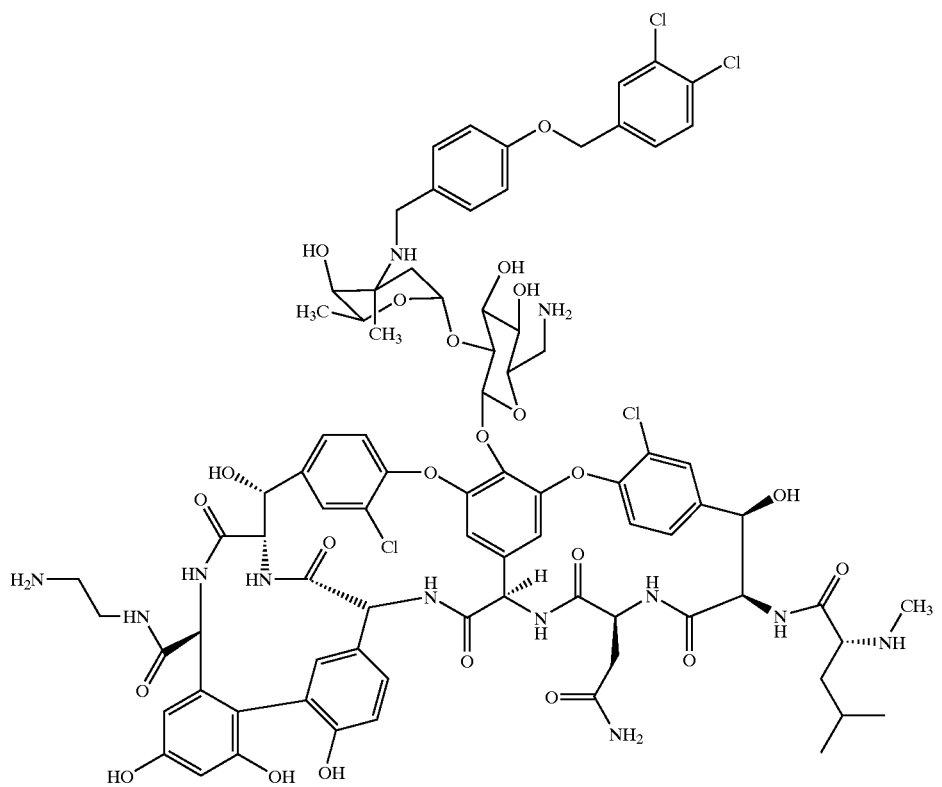

352-46

SI-352-46.

SI-352-40 (10 mg, 5.6 μmol) was dissolved in a mixture of 0.1 mL of EtOH, 0.2 mL of water and 0.4 mL of THF. Finally PMe₃ (45 μL, 45 μmol) was added and the reaction was stirred at room temperature overnight. The reaction was concentrated to dryness under reduced pressure and lyophilized to yield a white solid. The crude white solid was purified by HPLC (YMC-CYANO column) to yield 6 mg (61%) of a white solid.

LCMS shows M+1 (1757.3) and M/2+1 (878.8); M−1 (1753.8) and M/2−1 (876.5). Estimated Purity by LC-MS -90+%.

EXAMPLE 11

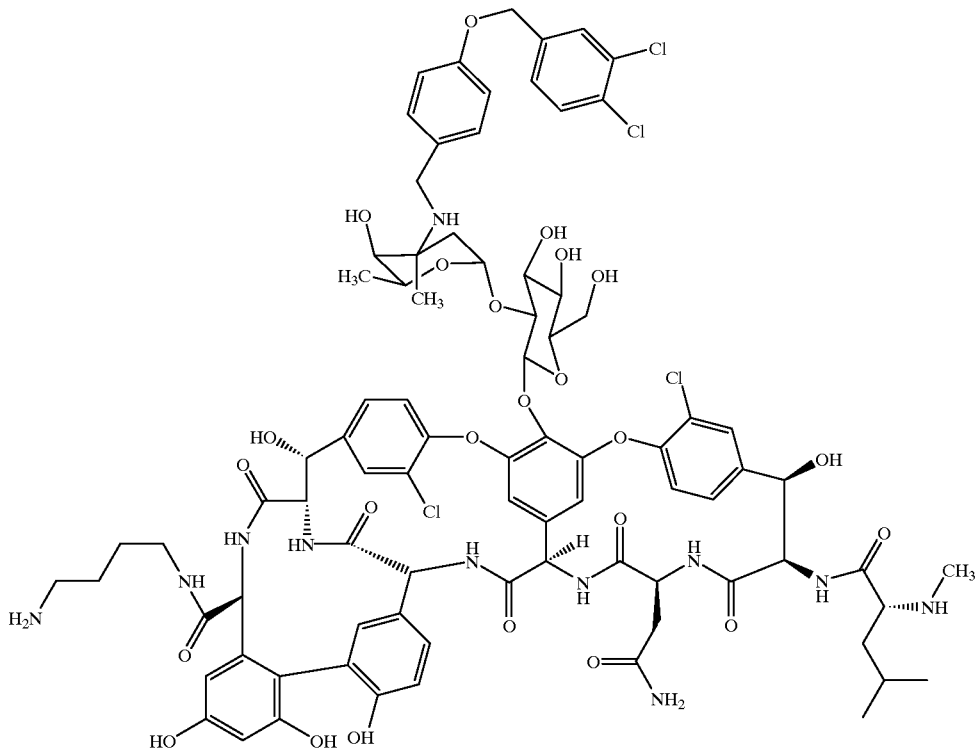

352-48

SI-352-48:

SI-352-42 (100 mg, 58.33 μmol) and putrescine (47 mg, 0.292 mmol, 5 equiv.) were azeotrophed with toluene (10 mL) three times. 1 mL of dry DMSO and 1 mL of dry DMF were added and the mixture was cooled to 0 C, and HBTU (66 mg, 0.175 mmol, 3 equiv.) and HOBT (24 mg, 0.175 mmol, 3 equiv.) were added, followed by diisopropylethylamine (110 μL, 10 equiv.) The reaction was then allowed to warm to room temperature. After 2 h, LC-MS showed near loss of SI-352-42 and appearance of a product with M/2+1 at 893. The reaction mixture was poured into ether and stirred until the turbid mixture became clear. The clear supernatant ether layer was decanted and 2 mL of DMF was added. The clear supernatant ether layer was decanted and 2 mL of DMF was added. To the DMF solution was added 50 mL of ether. The product precipitated as a white fluffy solid. The ether layer was decanted and the precipitate was washed with ether to remove traces of DMF. The white precipitate was dissolved in 3 mL of water and lyophilized to yield a white solid. The product was purified by semi-preparative HPLC (YMC-CYANO column) and lyophilized to afford 24 mg (23%; corrected yield based on reacted starting material—39%) of the desired product as a fluffy white solid. 41 mg of the starting material (41%) and 32 mg of an impurity (M=1827; M/2=913.5) were also recovered.

LCMS shows M/2+1 (894); M−1 (1783) and M/2 (892.3). Estimated Purity by LC-MS -95%.

In the Table below, MIC (minimum inhibitory concentration) values of certain compounds of the present invention are provided for the bacterial strains *E. faecalis* ATCC 29212; *E. faecalis* CL4877; *E. faecium* ATCC 49624; *E. faecium* CL4931; *S. aures* ATCC 29213; *S. aureus* ATCC 33591; and *E. coli* BAS 849. The MICs of the test compounds were determined using bacteria grown in brain heart infusion media (BHI) supplemented with 0.1% casamino acids. Logarithmically growing cells were diluted to approximately $5 \times 10^5$ CFU/ml and subjected to test compounds solubilized and serially diluted with DMSO. A 5% final DMSO concentration had no effect on cell viability or killing. After 18 hours at 37° C., the $OD_{600}$ was determined by reading the ninety-six well microtiter plates on a microplate reader. For a given concentration, an MIC determination was made if:

$$[OD_{600} \text{ Control} - OD_{600} \text{ Test Conc.}]/[OD_{600} - OD_{600} \text{ Media}] \times 100 \geq 90\%.$$

| Object Id | Structure | Bacteria | MIC μg/ml |
|---|---|---|---|
| EXT0002 (vancomycin) | 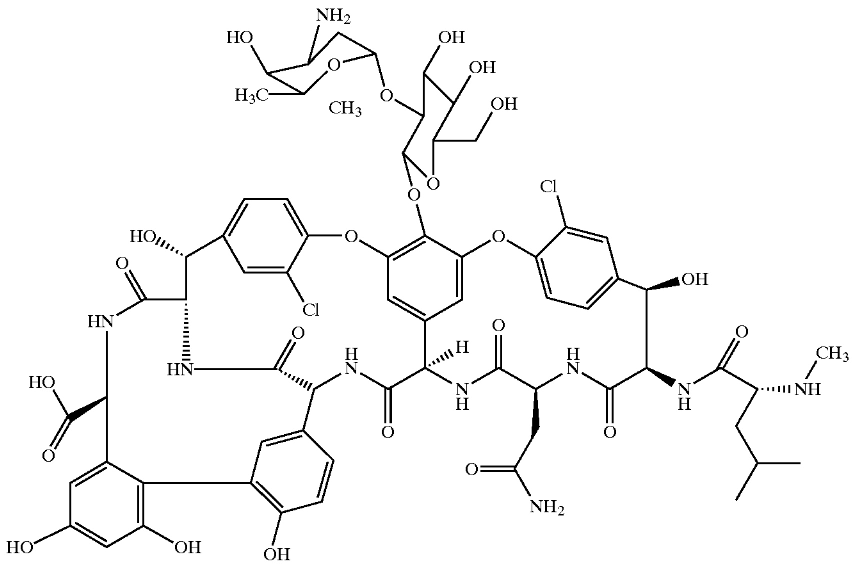 | E. faecalis ATCC29212 | 1.56–3.12 |
| | | E. faecalis CL4877 | >25 |
| | | E. faecium ATCC49624 | 0.25–0.39 |
| | | E. faecium CL4931 | >25 |
| | | S. aureus ATCC29213 | 1.56 |
| | | S. aureus ATCC33591 | 0.78–3.12 |
| | | E. coli BAS849 | 0.78 |

-continued
| Object Id | Structure | Bacteria | MIC µg/ml |
|---|---|---|---|
| TS0220 SI-352-33 (6'-azido-3,4-dichloro-benzyloxybenzyl-vancomycin putrescine amide) | 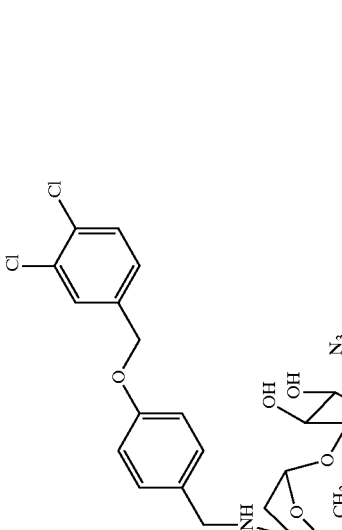 | E. faecalis ATCC29212 | 1.5625 |
| | | E. faecalis CL4877 | 1.5625 |
| | | E. faecium ATCC49624 | 0.7813 |
| | | E. faecium CL4931 | 3.1250 |
| | | S. aureus ATCC29213 | 1.5625 |
| | | S. aureus ATCC33591 | 3.1250 |

-continued
| Object Id | Structure | Bacteria | MIC µg/ml |
|---|---|---|---|
| TS0222 SI-352-36 (6'-azido-chlorobiphenyl methyl-vancomycin) putrescine amide | 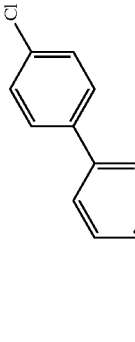 | E. faecalis ATCC29212<br>E. faecalis CL4877<br>E. faecium ATCC49624<br>E. faecium CL4931<br>S. aureus ATCC29213<br>S. aureus ATCC33591 | 0.7813<br>3.1250<br>0.2500<br>3.1250<br>1.5625<br>3.1250 |

-continued

| Object Id | Structure | Bacteria | MIC µg/ml |
|---|---|---|---|
| TS0216 SI-352-35 (6'-amino-3,4-dichloro-benzyloxylbenzyl-vancomycin putrescine amide) | 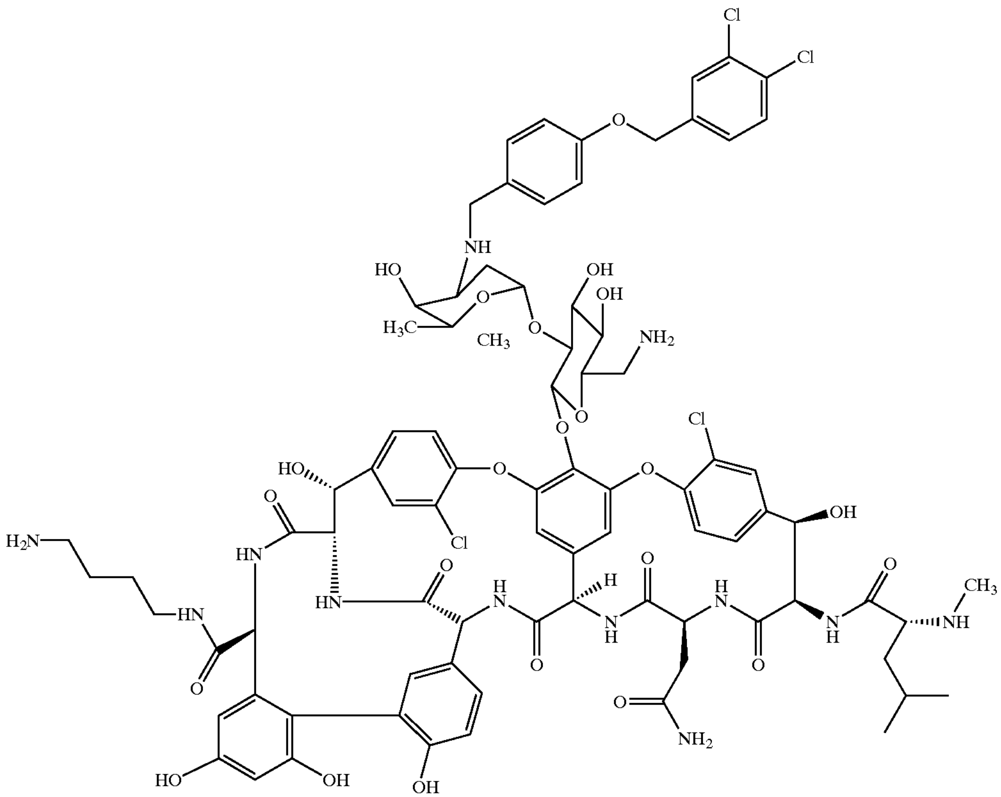 | E. faecalis ATCC29212 | 1.56 |
| | | E. faecalis CL4877 | 3.12 |
| | | E. faecium ATCC49624 | 3.12 |
| | | E. faecium CL4931 | 6.25 |
| | | S. aureus ATCC29213 | 3.12 |
| | | S. aureus ATCC33591 | 3.12 |
| | | E. coli BAS849 | 3.12 |

-continued

| Object Id | Structure | Bacteria | MIC μg/ml |
|---|---|---|---|
| TS0217 SI-352-38 (6'-amino-chlorobiphenyl methyl-vancomycin putrescine amide) | 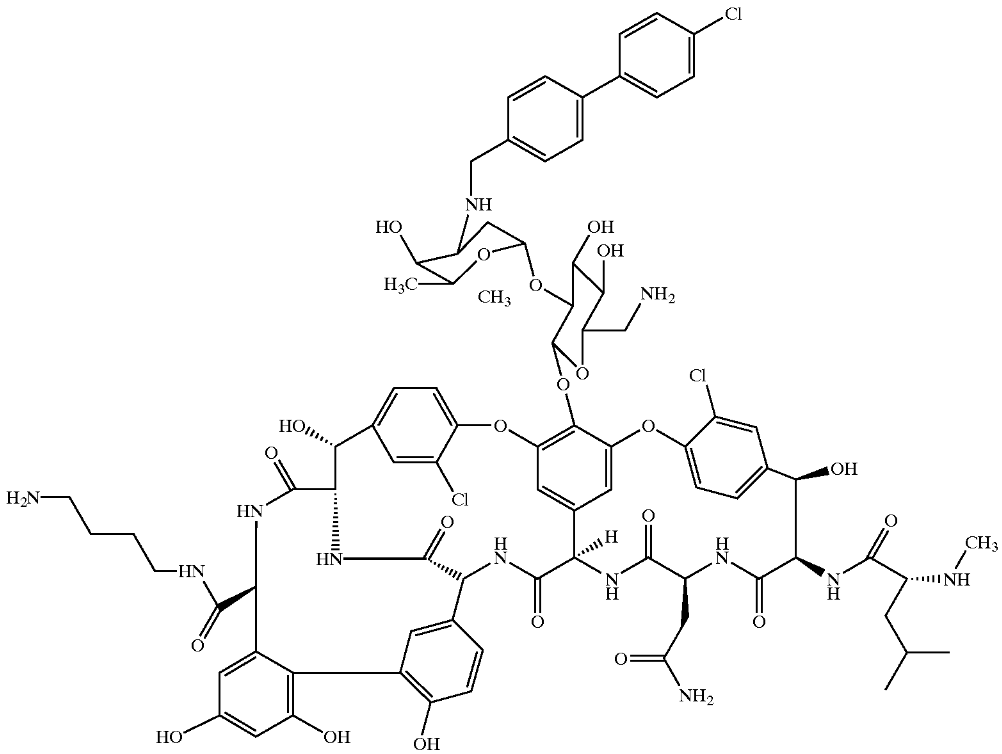 | E. faecalis ATCC29212 | 1.56 |
| | | E. faecalis CL4877 | 6.25 |
| | | E. faecium ATCC49624 | 1.56 |
| | | E. faecium CL4931 | 12.5 |
| | | S. aureus ATCC29213 | 1.56 |
| | | S. aureus ATCC33591 | 3.12 |
| | | E. coli BAS849 | 3.12 |

-continued

| Object Id | Structure | Bacteria | MIC µg/ml |
|---|---|---|---|
| TS0221 SI-352-31 (chlorobiphenylmethyl-vancomycin putrescine amide) | 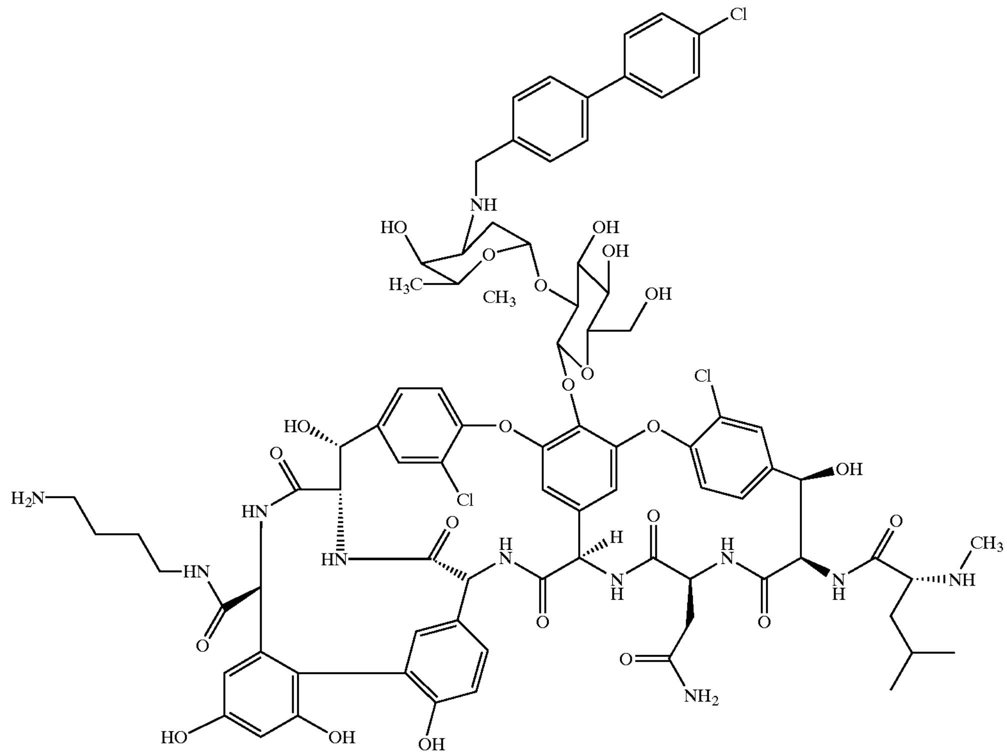 | E. faecalis ATCC29212 | 1.5625 |
| | | E. faecalis CL4877 | 12.5000 |
| | | E. faecium ATCC49624 | 0.2500 |
| | | E. faecium CL4931 | 6.2500 |
| | | S. aureus ATCC29213 | 1.5625 |
| | | S. aureus ATCC33591 | 0.7813 |

-continued

| Object Id | Structure | Bacteria | MIC µg/ml |
|---|---|---|---|
| TS0259 SI-352-56-10 (N-methyl, N-chlorobiphenyl methyl-D-leucyl-6'-azido-chlorobiphenyl methyl vancomycin putrescine amide) | 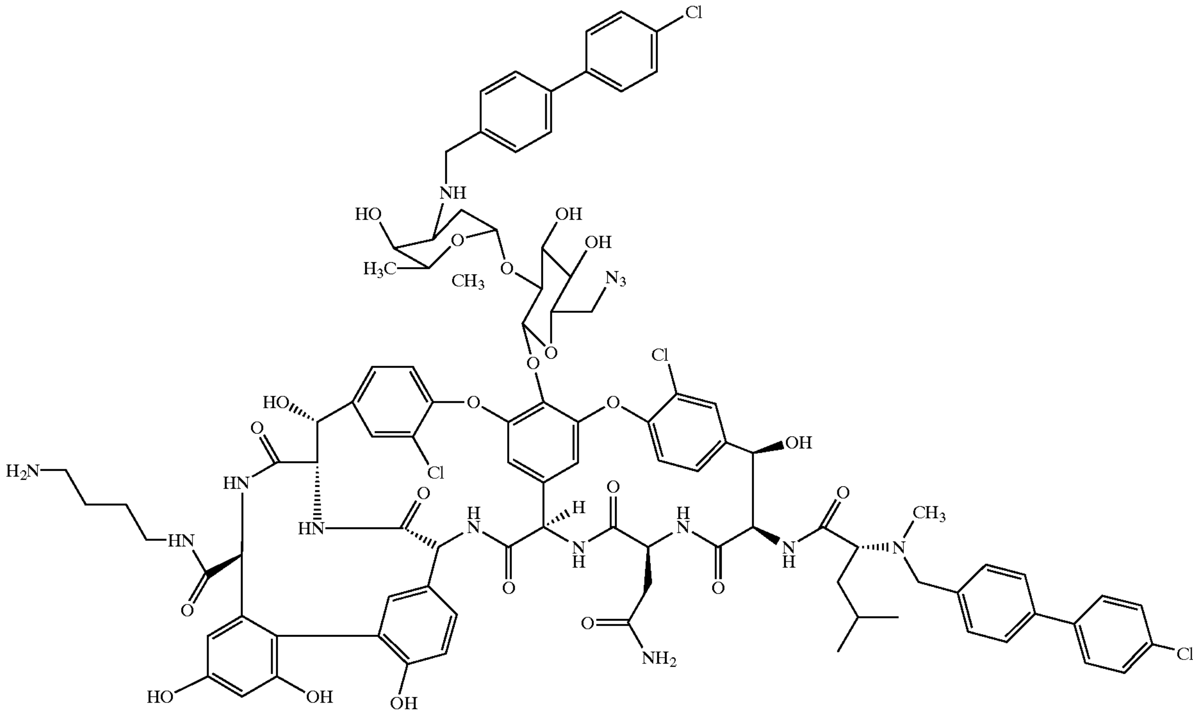 | E. faecalis ATCC29212<br>E. faecalis CL4877<br>E. faecium ATCC29624<br>E. faecium CL4931<br>E. aureus ATCC29213<br>S. aureus ATCC33591 | 3.12<br>12.5<br>1.56<br>6.25<br>3.12<br>1.56 |

-continued

| Object Id | Structure | Bacteria | MIC µg/ml |
|---|---|---|---|
| TS0256 SI-352-40 (6'-azido-3,4-dichlorobenzyl oxylbenzyl-vancomycin 2-aminoethyl amide) | 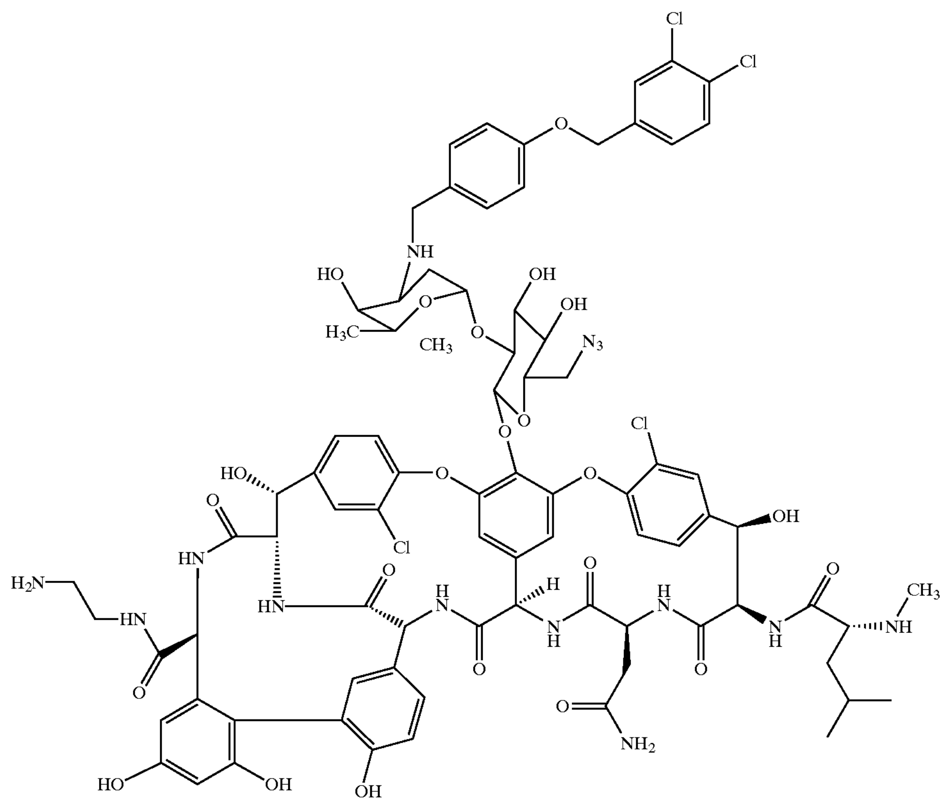 | E. faecalis ATCC29212 | 3.12 |
| | | E. faecalis CL4877 | 1.56 |
| | | E. faecium ATCC49624 | 0.39 |
| | | E. faecium CL4931 | 6.25 |
| | | S. aureus ATCC29213 | 1.56 |
| | | S. aureus ATCC33591 | 1.56 |
| | | E. coli BAS849 | |

-continued

| Object Id | Structure | Bacteria | MIC µg/ml |
|---|---|---|---|
| TS0258 SI-352-46 (6′-amino-3,4-dichlorobenzyl oxylbenzyl-vancomycin 2-aminoethyl amide) | | E. faecalis ATCC29212 | 12.5 |
| | | E. faecalis CL4877 | 25 |
| | | E. faecium ATCC49624 | 3.12 |
| | | E. faecium CL4931 | 25 |
| | | S. aureus ATCC29213 | 25 |
| | | S. aureus ATCC33591 | 12.5 |
| | | E. coli BAS849 | |

What is claimed is:

1. A compound of the formula:

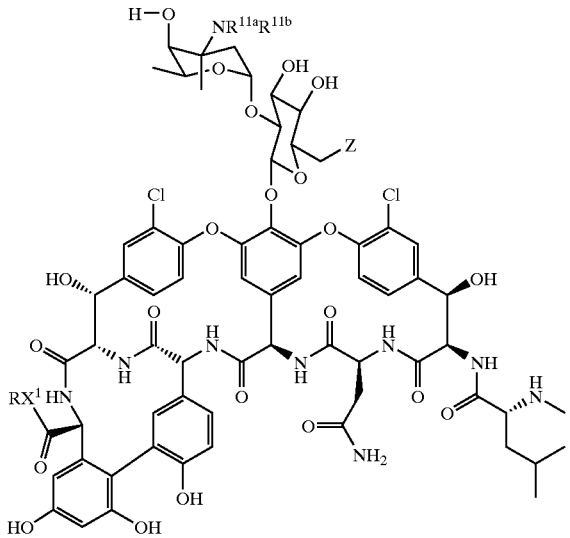

wherein $X^1$ is O, S, NR, $NR^1$, $NR^2$, with the proviso that $RX^1$ is not OH;

wherein R is hydrogen, substituted or unsubstituted alkyl, aryl, aralkyl, alkanoyl, aroyl, aralkanoyl, heterocyclic, heterocyclic-carbonyl, heterocyclic-alkyl-carbonyl, alkylsulfonyl or arylsulfonyl; $R^1$; or $R^2$;

wherein $R^1$ is a radical of the formula
—[$(CH_2)_m NR^3$]$_n$—Q—[$(CH)_k NR^4$]$_h$—$(CH_2)_p$—$NR^5 R^6$
wherein: any of $R^3$, $R^4$, $R^5$ and $R^6$ is hydrogen or linear or branched ($C_1$–$C_8$)alkyl that may optionally be substituted with one or more substituents each of which is independently selected from the group consisting of halo, nitro, cyano, loweralkoxy of $C_1$–$C_4$, haloloweralkyl of $C_1$–$C_4$, haloloweralkoxy of $C_1$–$C_4$, $NH_2$, OH or SH; or $R^5$ and $R^6$ taken together with the adjacent nitrogen atom, form a 5 to 7 membered saturated heterocyclic ring which may contain a further heteroatom selected from —S—, —O—, and $NR^7$ wherein $R^7$ is hydrogen, ($C_1$–$C_4$)alkyl, phenyl, or phenyl-($C_1$–$C_4$)alkyl; m, k and p, each independently represent and integer from 2 to 8; n and h, each independently, represent an integer from 0 to 4; Q represents a single bond, or when n is 1, taken together with the adjacent group $NR^3$, it may represent a bifunctional radical of the formula:

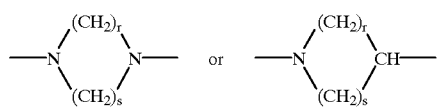

wherein r and s each independently represent an integer from 1 to 6 with the proviso that their sum is an integer from 3 to 8; and their addition salts with acids;

wherein $R^2$ is —$CH_2 R^8$ or $C(O)R_8$; wherein $R^8$ is hydrogen, alkyl of $C_1$–$C_{15}$, alkenyl of $C_2$–$C_{15}$, alkynyl of $C_2$–$C_{15}$, haloalkyl of $C_1$–$C_{10}$, $R^9$, alkyl of $C_1$–$C_{15}$-$R^9$, alkenyl of $C_2$–$C_{15}$-$R^9$, alkynyl of $C_2$–$C_{15}$-$R^9$, or alkyl of $C_1$–$C_{15}$-O-$R^9$; wherein $R^9$ is aryl, heteroaryl, cycloalkyl, or heterocyclic any of which may be substituted or unsubstituted, or a radical of the formula —$R^{10}$—[linker$_{(0\ or\ 1)}$—$R^{10}$]$_{(0\ or\ 1)}$ wherein each $R^{10}$ independently represents phenyl, heteroaryl, cycloalkyl or heterocyclic, each of which is unsubstituted or optionally substituted with one or two substituents, each of which is independently alkyl of $C_1$–$C_{10}$, haloalkyl of $C_1$–$C_{10}$, haloalkoxy of $C_1$–$C_{10}$, alkoxy of $C_1$–$C_{10}$, halo, cyano, or nitro; and "linker" is: -alkylene of $C_1$–$C_3$-, -alkylene of $C_1$–$C_6$-, -alkylene of $C_1$–$C_6$O—, —O—, —N(H or lower alkyl of $C_1$–$C_6$)—, —S—, —SO—, —$SO_2$—, —O—$SO_2$—O—, —$SO_2$—O—, —NHC(O)—, —C(O)—, —C(O)NH—, —CH=CH—, —C≡C—, —N=N—, —OC(O)—, or —C(O)O—;

wherein $R^{11a}$ and $R^{11b}$ are independently selected from R, $R^1$ and $R^2$ with the proviso that $R^{11a}$ and $R^{11b}$ cannot both be hydrogen;

wherein Z is a substituent of the formula $YX^2 R^{12}$, $N_3$, $N^+(R^{13})=CR^{14}R^{15}$, N=$PR^{13}R^{14}R^{15}$, $N^+R^{13}R^{14}R_{15}$ or $P^+R^{13}R^{14}R^{15}$ in which the group Y is a single bond, O, $NR^{12}$ or S; the group $X^2$ is O, $NR^{12}$, S, $SO_2$, C(O)O, C(O)S, C(S)O, C(S)S, C($NR^{12}$), C(O)$NR^{12}$, or halo (in which case and $R^{12}$ are absent); $R^{12}$, $R^{13}$, $R^{14}$ and $R^{15}$ are independently R, $R^1$ or $R^2$ as defined above, provided that X and Y are not both O; X and Y are not S and O, or O and S, respectively; or a pharmaceutically acceptable salt or ester of said compound.

2. The compound of claim 1 wherein $R^{11a}$ or $R^{11b}$ is a hydrophobic substituent.

3. The compound of claim 2 wherein at least one of $R^{11a}$ or $R^{11b}$ is selected from the group consisting of 4-phenylbenzyl, 4-phenoxybenzyl, 4-benzyloxybenzyl, 4-(4-chlorophenyl)benzyl, 4-(4-chlorophenoxy)benzyl, 4-(4-chlorobenzyloxy)benzyl, 4-(3,4-dichlorophenyl)benzyl, 4-(3,4-dichlorophenoxy)benzyl and 4-(3,4-dichlorobenzyloxy)benzyl.

4. The compound of claim 1 wherein $R^1$ is selected from the group consisting of —$(CH_2)_{1-9} NH_2$ and R is hydrogen.

5. The compound of claim 4 wherein $R^1$ is —$(CH_2)_4 NH_2$ or —$(CH_2)_2 NH_2$.

6. The compound of claim 5 wherein $R^1$ is —$(CH_2)_4 NH_2$.

7. The compound of claim 5 wherein $R^1$ is —$(CH_2)_2 NH_2$.

8. The compound of claim 5 wherein at least one of $R^{11a}$ or $R^{11b}$ is selected from the group consisting of 4-phenylbenzyl, 4-phenoxybenzyl, 4-benzyloxybenzyl, 4-(4-chlorophenyl)benzyl, 4-(4-chlorophenoxy)benzyl, 4-(4-chlorobenzyloxy)benzyl, 4-(3,4-dichlorophenyl)benzyl, 4-(3,4-dichlorophenoxy)benzyl and 4-(3,4-dichlorobenzyloxy)benzyl.

9. The compound of claim 1 wherein Z is selected from the group consisting of hydroxyl, amino, azido, halo and hydrazino.

10. The compound of claim 8 wherein Z is selected from the group consisting of hydroxyl, amino, azido, halo and hydrazino.

11. A composition comprising the compound of claim 1, or a pharmaceutically acceptable salt or ester thereof in combination with a pharmaceutically acceptable carrier or diluent.

12. A method of treating a bacterial infection in a host comprising administering to said host a therapeutically effective amount of the compound of claim 1.

13. The method of claim 12 wherein the host is an animal.

14. The method of claim 13 wherein the animal is a human.

15. A method of treating a bacterial infection in a host comprising administering to said host a therapeutically effective amount of the composition of claim 11.

16. The method of claim 15 wherein the host is an animal.

17. The method of claim 16 wherein the animal is a human.

18. A process for the preparation of a compound of claim 1 wherein $X^1$ is $NR_1$ comprising reaction a compound of the formula

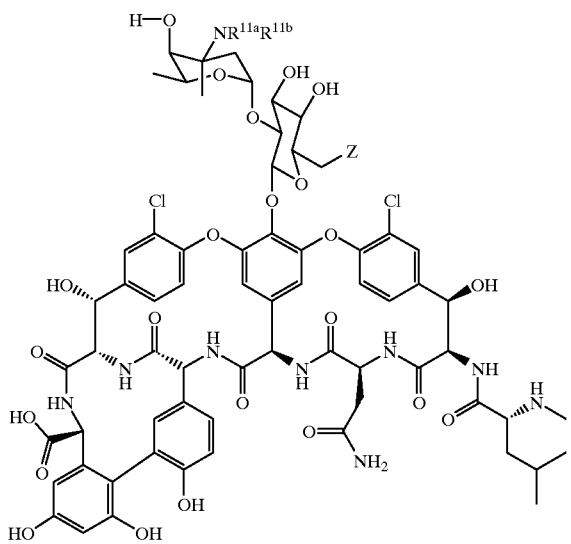

with a compound of the formula NHR—[(CH$_2$)$_m$NR$^3$]$_n$-Q-[(CH)$_k$NR$^4$]$_h$-(CH$_2$)$_p$-NR$^5$R$^6$ and optionally forming a salt thereof.

19. The compound of claim 1 wherein $R^1$ is —(CH$_2$)$_4$NH$_2$; $R^{11a}$ is hydrogen; $R^{11b}$ is 4-(3,4-dichlorobenzyloxy)benzyl; $X^1$ is NH and Z is amino.

* * * * *

UNITED STATES PATENT AND TRADEMARK OFFICE
CERTIFICATE OF CORRECTION

PATENT NO. : 6,699,836 B2
APPLICATION NO. : 09/818787
DATED : March 2, 2004
INVENTOR(S) : Kahne et al.

It is certified that error appears in the above-identified patent and that said Letters Patent is hereby corrected as shown below:

In column 6, line 33, please change the line to read as follows.

Q—[(CH$_\underline{2}$)$_k$NR$^4$]$_h$—(CH$_2$)$_p$—NR$^5$R$^6$ wherein: any of R$^3$, In Column 8, line 16, please change the line to read as follows:

—[(CH$_2$)$_m$NR$^3$]$_n$—Q—[(CH$_\underline{2}$)$_k$NR$^4$]$^h$—(CH$_2$)$_p$—NR$^5$R$^6$ In Column 104, line 25, please change the line to read as follows:

[(CH$_\underline{2}$)$_k$NR$^4$]$_h$—(CH$_2$)$_p$—NR$^5$R$^6$ and optionally forming a salt In column 101, line 41, please change the line as follows:

—[(CH$_2$)$_m$NR$^3$]$_n$—Q—[(CH$_\underline{2}$)$_k$NR$^4$]$_h$—(CH$_2$)$_p$—NR$^5$R$^6$ Also in column 101, line 55, please change the line as follows:

Pendently represent ~~and~~ an integer from 2 to 8; n and h, each

Signed and Sealed this

Fourth Day of September, 2007

JON W. DUDAS
*Director of the United States Patent and Trademark Office*